(12) United States Patent
Smith et al.

(10) Patent No.: US 7,759,376 B2
(45) Date of Patent: Jul. 20, 2010

(54) PREPARATION AND USE OF BIPHENYL-4-YL-CARBONYLAMINO ACID DERIVATIVES FOR THE TREATMENT OF OBESITY

(75) Inventors: Roger Smith, Madison, CT (US); Stephen J. O'Connor, Guilford, CT (US); Philip Coish, North Haven, CT (US); Derek Lowe, Hamden, CT (US); Roger B. Clark, Lexington, MA (US); Jeffrey Stebbins, San Diego, CA (US); Ann-Marie Campbell, Monroe, CT (US); Christiana Akuche, Hamden, CT (US); Tatiana Shelekhin, Ridgefield, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 607 days.

(21) Appl. No.: 11/665,317

(22) PCT Filed: Oct. 14, 2005

(86) PCT No.: PCT/US2005/037215

§ 371 (c)(1),
(2), (4) Date: Apr. 13, 2007

(87) PCT Pub. No.: WO2006/044775

PCT Pub. Date: Apr. 27, 2006

(65) Prior Publication Data

US 2007/0265298 A1    Nov. 15, 2007

Related U.S. Application Data

(60) Provisional application No. 60/618,975, filed on Oct. 15, 2004.

(51) Int. Cl.
*A61K 31/425* (2006.01)
*C07D 277/82* (2006.01)
(52) U.S. Cl. ........................ 514/367; 548/161
(58) Field of Classification Search ................ 548/161; 514/367

See application file for complete search history.

(56) References Cited

OTHER PUBLICATIONS

Zhao et al., J. Med. Chem. 2008, 51, 380-383.*
Database CAS Online on STN, Chem. Abstr., Accession No. 2004:964835, US2004224997, Preparation of benzazolyaminobiphenyloxoalkanoates; Smith et al., Nov. 11, 2004, abstract.

* cited by examiner

*Primary Examiner*—Rebecca L Anderson
(74) *Attorney, Agent, or Firm*—Barry Kramer; Ralph A. Loren; Edwards Angell Palmer & Dodge LLP

(57) ABSTRACT

This invention relates to certain biphenyl-4-yl carbonylamino acid compounds, compositions, and methods for treating or preventing obesity and related diseases.

9 Claims, No Drawings

PREPARATION AND USE OF BIPHENYL-4-YL-CARBONYLAMINO ACID DERIVATIVES FOR THE TREATMENT OF OBESITY

This application claims benefit of U.S. Provisional Application Ser. No. 60/618,975; filed on Oct. 15, 2004, the contents of which are incorporated herein by reference in their entirety.

FIELD OF THE INVENTION

This invention relates to certain biphenyl-4-yl carbonylamino acid compounds, compositions, and methods for treating or preventing obesity and related diseases.

BACKGROUND OF THE INVENTION

Obesity, which is an excess of body fat relative to lean body mass, is a chronic disease that is highly prevalent in modern society. It is associated not only with a social stigma, but also with decreased life span and numerous medical problems, including adverse psychological development, coronary artery disease, hypertension, stroke, diabetes, hyperlipidemia, and some cancers (see, e.g., Nishina, et al., Metab. 43:554-558, 1994; Grundy and Barnett, Dis. Mon. 36:641-731, 1990; Rissanen, et al., British Medical Journal, 301:835-837, 1990).

Obesity remains a problem, and treatment has been limited. There is, therefore, a need to develop pharmaceuticals and treatment regimes effective in the alleviation of obesity.

A hallmark characteristic of obesity is an increase in white adipose tissue (WAT) mass that is largely due to accumulation of triacylglycerol. This increase in WAT mass is a key contributor to obesity-associated complications. Diacylglycerol O-acyltransferases (DGATs, EC 2.3.1.2) are membrane-bound enzymes that catalyze the terminal step of triacylglycerol biosynthesis. Two enzymes that display DGAT activity have been characterized: DGAT-1 (diacylglycerol O-acyltransferase type 1) (see, e.g., U.S. Pat. No. 6,100,077; Cases, et al., Proc. Nat. Acad. Sci. 95:13018-13023, 1998) and DGAT-2 (diacylglycerol O-acyltransferase type 2) (Cases, et al., J. Biol. Chem. 276:38870-38876, 2001). DGAT-1 and DGAT-2 do not exhibit significant protein sequence identity. Importantly, DGAT-1 null mice do not become obese when challenged with a high fat diet in contrast to wild-type littermates (Smith, et al., Nature Genetics 25:87-90, 2000). DGAT-1 null mice display reduced postprandial plasma glucose levels and exhibit increased energy expenditure, but have normal levels of serum triglycerides (Smith, et al., 2000), possibly due to the preserved DGAT-2 activity. Since DGAT-1 is expressed in the intestine and adipose tissue (Cases, et al., 1998), there are at least two possible mechanisms to explain the resistance of DGAT-1 null mice to diet-induced obesity. First, abolishing DGAT-1 activity in the intestine may block the reformation and export of triacylglycerol from intestinal cells into the circulation via chylomicron particles. Second, knocking out DGAT-1 activity in the adipocyte may decrease deposition of triacylglycerol in WAT. The phenotype of the DGAT-1 null mouse, along with the results of our studies with DGAT-1 inhibitors in diet-induced obese (DIO) mice, indicate that a DGAT-1 inhibitor has utility for the treatment of obesity and obesity-associated complications.

SUMMARY OF THE INVENTION

The present invention relates to biphenyl-4-yl carbonylamino acid compounds, compositions, and methods for the treatment and prevention of obesity and related diseases.

Accordingly, one embodiment of the present invention is to provide compounds as depicted in the Tables and in the Examples.

Another embodiment of the invention is to provide a method of treating or preventing obesity and related diseases in a subject comprising administering to a subject in need thereof an effective amount of at least one compound of the invention.

A further embodiment of the present invention is to provide compositions for treating or preventing obesity and related diseases in a subject comprising an effective amount of at least one compound of the invention.

These and other objects of the invention will be clear in light of the detailed description below.

DETAILED DESCRIPTION OF THE INVENTION

The invention relates to biphenyl-4-yl carbonylamino acid derivatives, and pharmaceutical salts and esters thereof, that have utility in the inhibition of DGAT-1 (diacylglycerol O-acyltransferase type 1) and in the treatment of obesity and related diseases.

One embodiment of the invention is a compound of Formula (I)

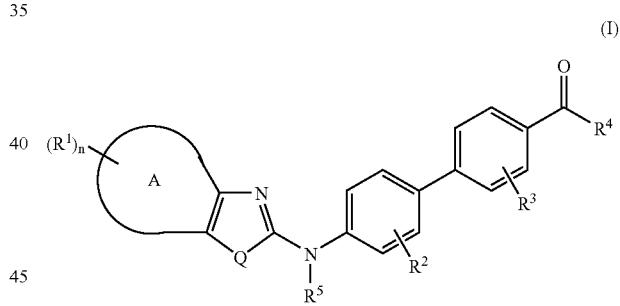

wherein
Q is O, $NR^{11}$, or S;

is a fused ring selected from
an aromatic 6-membered ring containing 0 or 1 N atoms;
$R^1$ is independently selected from
halo, $(C_1-C_6)$alkyl, $(C_1-C_6)$alkoxy, nitro, cyano, $(C_1-C_6)$haloalkyl, $(C_1-C_6)$haloalkoxy, aminocarbonyl, $(C_1-C_6)$alkylaminocarbonyl, bis[$(C_1-C_6)$alkyl]aminocarbonyl, aminosulfonyl, $(C_1-C_6)$alkylaminosulfonyl, bis[$(C_1-C_6)$alkyl]aminosulfonyl, $(C_1-C_6)$alkylcarbonylamino, $(C_1-C_6)$alkylsulfonyl, $(C_1-C_6)$alkylsulfonylamino, hydroxy-$(C_2-C_6)$alkylaminocarbonyl, 1-morpholinylcarbonyl, and 1-piperidinylcarbonyl, and
when two of said $R^1$ substituents are $(C_1-C_6)$alkyl and are attached to adjacent carbon atoms of the Ring A, they may be joined together to form a 5-7-membered carbocyclic ring;

n is 0, 1, or 2;

$R^2$ and $R^3$ are independently selected from hydrogen, halo, hydroxy, $(C_1-C_6)$alkyl, trifluoromethyl, $(C_1-C_6)$alkoxy, and trifluoromethoxy;

$R^4$ is selected from

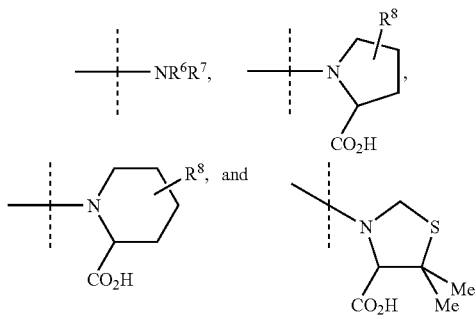

wherein
$R^6$ is H or $CH_3$;
and
$R^7$

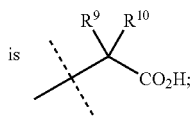

wherein
$R^9$ is selected from
$(C_1-C_6)$alkyl optionally substituted with one or two groups selected from vinyl, $CF_3$, OH, methoxy, $SCH_3$, $NH_2$, $-CO_2H$, and $-CONH_2$,
$(CH_2)_m$phenyl wherein m is 0 to 3, and where the phenyl ring is optionally substituted with one or two groups selected from halo, $(C_1-C_6)$alkyl, $(C_1-C_6)$alkoxy, OH, nitro, and cyano,
piperidinyl optionally substituted on C with halo and optionally substituted on C or N with $(C_1-C_6)$alkyl, $(C_1-C_6)$alkoxy, nitro, or cyano,
tetrahydropyran-4-yl;
$R^{10}$ is H or methyl;
or
$R^9$ and $R^{10}$ may form, together with the carbon to which they are attached, a 3- to 6-membered carbocyclic ring,
$R^8$ is hydrogen, $(C_1-C_4)$alkyl, hydroxy, or methoxy;
$R^5$ is selected from H, $(C_1-C_6)$alkyl, and hydroxy-$(C_2-C_6)$alkyl;
$R^{11}$ is selected from H, $(C_1-C_6)$alkyl, and hydroxy-$(C_2-C_6)$alkyl;

and the pharmaceutically acceptable salts and esters thereof.

The terms identified above have the following meaning throughout:

The term "halo" means F, Br, Cl, and I.

The terms "$(C_1-C_4)$alkyl," "$(C_1-C_6)$alkyl," and "$(C_2-C_6)$alkyl" mean a linear or branched saturated hydrocarbon groups having from 1 to about 4 carbon atoms, from 1 to about 6 carbon atoms, or from 2 to about 6 carbon atoms, respectively. The hydrocarbon group may also include a cyclic alkyl fragment as part of the alkyl group. Such groups include, but are not limited to, methyl, ethyl, n-propyl, isopropyl, butyl, isobutyl, pentyl, hexyl, cyclopropyl, cyclohexyl, cyclopropyl-methyl, and cyclopentyl-methyl groups.

The term "$(C_1-C_6)$alkoxy" means a linear or branched saturated hydrocarbon group having from 1 to about 6 carbon atoms, said group being attached to an oxygen atom. The oxygen atom is the atom through which the alkoxy substituent is attached to the rest of the molecule. The hydrocarbon group may also include a cyclic alkyl fragment as part of the alkyl group. Such groups include, but are not limited to, methoxy, ethoxy, n-propoxy, isopropoxy, n-butoxy, n-hexyloxy, 3,3-dimethylpropoxy, cyclopropoxy, cyclopropylmethoxy, cyclopentyloxy, and the like.

The term "$(C_1-C_6)$haloalkoxy" means a $(C_1-C_6)$alkoxy group substituted on carbon with a halogen atom. Such groups include, for example, trifluoromethoxy, difluoromethoxy, 2,2-difluoroethoxy, 2,2,2-trifluoroethoxy, 3-fluoropropoxy, 2-chloroethoxy, 3-chloropropoxy, 1-fluoro-2,2,-dichloroethoxy, and the like.

The term "$(C_1-C_6)$haloalkyl" means a $(C_1-C_6)$alkyl group substituted on carbon with a halogen atom. Such groups include, for example, trifluoromethyl, difluoromethyl, 2,2,2-trifluoroethyl, 3-fluoropropyl, difluoroethyl, 1-fluoro-2,2-dichloroethyl, 3-chloropropyl, 4-bromohexyl, and the like.

The terms "aminocarbonyl," "$(C_1-C_6)$alkylaminocarbonyl," and "bis[$(C_1-C_6)$alkyl]aminocarbonyl" mean a carbonyl [C(=O)] group substituted by nitrogen atom in which the nitrogen atom is unsubstituted, substituted by a single $(C_1-C_6)$alkyl group, or by two $(C_1-C_6)$alkyl groups, respectively. The carbonyl group is the point of attachment of the substituent to the rest of the molecule. Such groups include, for example, carboxamido [$NH_2C$(=O)—], N-methylcarboxamido [$CH_3NHC$(=O)], N-methyl-N-propylcarboxamido [$CH_3CH_2CH_2N(CH_3)C$(=O)—], N,N-diethylcarboxamido [$(CH_3CH_2)_2NC$(=O)—], and the like.

The terms "3- to 6-membered carbocyclic ring" and "5- to 7-membered carbocyclic ring" mean a saturated or partially unsaturated ring containing from about 3 to about 6 carbon atoms, and from about 5 to about 7 carbon atoms, respectively. Such groups include, but are not limited to, cyclopropyl, cyclobutyl, cyclopentyl cyclohexyl, cycloheptyl, cyclopentenyl, cyclohexenyl, and the like.

The term "hydroxy-$(C_2-C_6)$alkyl" means a $(C_2-C_6)$alkyl group, said alkyl being further substituted by a hydroxy group at any available carbon atom. Such groups include, but are not limited to, hydroxymethyl, 2-hydroxyethyl, 2 hydroxypropyl, 3 hydroxypropyl, 4-hydroxybutyl, 2-hydroxy-1-methylethyl, 5-hydroxypentyl, 3-hydroxybutyl, 3-hydroxy-2-ethylpropyl, 6-hydroxyhexyl, and the like.

The term "hydroxy-$(C_2-C_6)$alkylaminocarbonyl" means a carbonyl [C(=O)] group substituted by nitrogen atom in which the nitrogen atom is substituted by a single $(C_2-C_6)$ alkyl group, and said alkyl is further substituted by a hydroxy group. Such groups include, for example, 2-hydroxyethylamido-, 3-hydroxypropylamido, 4-hydroxyhexylamido, and the like.

The terms "aminosulfonyl," "$(C_1-C_6)$alkylaminosulfonyl," and "bis[$(C_1-C_6)$alkyl]aminosulfonyl" mean a $S$(=O)$_2$ group substituted by nitrogen atom in which the nitrogen atom is unsubstituted, substituted by a single $(C_1-C_6)$alkyl group, or by two $(C_1-C_6)$alkyl groups, respectively. The $S$(=O)$_2$ group is the point of attachment of the substituent to the rest of the molecule. Such groups include, for example, aminosulfonyl [$NH_2S(=O)_2$—], N-methylaminosulfonyl-[$CH_3NHS(=O)_2$], N-methyl-N-propylaminosulfonyl [$CH_3CH_2CH_2N(CH_3)S(=O)_2$—], N,N,-diethylaminosulfonyl [$(CH_3CH_2)_2NS(=O)_2$—], and the like.

The term "($C_1$-$C_6$)alkylcarbonylamino" means an amino group in which the nitrogen atom is substituted by a carbonyl group, and said carbonyl group is further substituted by a ($C_1$-$C_6$)alkyl group. The nitrogen atom is the point of attachment of the substituent to the rest of the molecule. Such groups include, for example, acetylamino [$CH_3C(=O)NH$—], propanoylamino [$CH_3CH_2C(=O)NH$—], i-butanoylamino [$(CH_3)_2CHC(=O)NH$—] groups, and the like.

The term "($C_1$-$C_6$)alkylsulfonylamino" means an amino group in which the nitrogen atom is substituted by a sulfonyl [$S(=O)_2$] group, and said sulfonyl group is further substituted by a ($C_1$-$C_6$)alkyl group. The nitrogen atom is the point of attachment of the substituent to the rest of the molecule. Such groups include, for example, methylsulfonylamino [$CH_3S(=O)_2NH$—], propylsulfonylamino [$CH_3CH_2CH_2S(=O)_2NH$—], i-propylsulfonylamino [$(CH_3)_2CHS(=O)_2NH$—] groups, and the like.

The terms "1-morpholinylcarbonyl" and "1-pipenidinylcarbonyl" mean

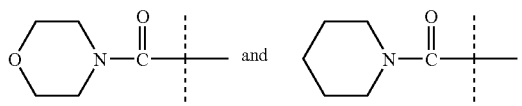

,respectively.

The term "piperidinyl" means

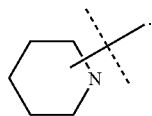

The point of attachment of this substituent may be either the N or any C atom in the ring.

The term "optionally substituted" means that the moiety so modified may have from none to up to at least the highest number of substituents indicated. Each substituent may replace any hydrogen atom on the moiety so modified as long as the replacement is chemically possible and chemically stable. When there are two or more substituents on any moiety, each substituent is chosen independently of any other substituent and can, accordingly, be the same or different.

Standard amino acid fragment abbreviations (e.g., Val, Leu, Ile, Pro, and the like) are used in the Tables below to describe a bivalent amino acid fragment. It is to be understood that the attachment points of the bivalent fragment are through the nitrogen atom of the fragment and the carbon atom of the carbonyl group. For example, in Table 1a, the fragment is attached to the molecule through the nitrogen atom and is substituted on the C(=O) with an OH group. As entered into the Table, the attachment point to the rest of the molecule is on the left, and the OH group is on the right. It also to be understood that when the fragment is designated as "L," its absolute configuration is that of the naturally occurring amino acids; whereas the designation "D" is of the opposite absolute configuration.

The compounds described in the Examples are intended to be representative of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Representative salts of the compounds of Formula (I) include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate and diamyl sulfates; long chain halides such as decyl, lauryl, myristyl and strearyl chlorides, bromides, and iodides; aralkyl halides like benzyl and phenethyl bromides and others.

The esters in the present invention are non-toxic, pharmaceutically acceptable ester derivatives of the compounds of Formula (I). This may include, for example, ester derivatives prepared from acetic, benzoic, mandelic, stearic, lactic, salicylic, hydroxynaphthoic, glucoheptonic, and gluconic acid. The compounds of Formula (I) may be esterified by a variety of conventional procedures well known by those skilled in the art. For example, esterification may be reached using the appropriate carboxylic acid in the presence of trifluoroacetic anhydride and optionally, pyridine, or in the presence of N,N-carbonyldiimidazole with pyridine. One skilled in the art would readily know how to successfully carry out these as well as other methods of esterification. Sensitive or reactive groups on the compound of Formula (I) may need to be protected during any of the above methods for forming esters, and protecting groups may be added and removed by conventional methods well known in the art.

It will be appreciated that diastereomers and enantiomers of the exemplified structures will often be possible, and that pure isomers represent one embodiment of the invention. It is intended that pure stereoisomers, and mixtures thereof, are within the scope of the invention.

The compounds of this invention may, either by nature of asymmetric centers or by restricted rotation, be present in the form of isomers. Any isomer may be present in the (R)-, (S)-, or (R,S) configuration, preferably in the (R)- or (S)-configuration, whichever is most active.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art.

Geometric isomers by nature of substituents about a double bond or a ring may be present in cis (=Z) or trans (=E-) form, and both isomeric forms are encompassed within the scope of this invention.

The particular process to be utilized in the preparation of the compounds of this invention depends upon the specific compound desired. Such factors as the selection of the specific moieties and the specific substituents on the various moieties, all play a role in the path to be followed in the preparation of the specific compounds of this invention. These factors are readily recognized by one of ordinary skill in the art.

For synthesis of any particular compound, one skilled in the art will recognize that the use of protecting groups may be required for the synthesis of compounds containing certain substituents. A description of suitable protecting groups and appropriate methods of adding and removing such groups may be found in the art (see, e.g., T. W. Greene and P. G. M. Wuts, *Protective Groups in Organic Synthesis*; Wiley: New York, (1999)).

In the reaction schemes below, one skilled in the art will recognize that reagents and solvents actually used may be selected from several reagents and solvents well known in the art to be effective equivalents. When specific reagents or solvents are shown in a reaction scheme, therefore, they are meant to be illustrative examples of conditions desirable for the execution of that particular reaction scheme. Abbreviations not identified in accompanying text are listed later in this disclosure under "Abbreviations and Acronyms."

Another object of this invention is to provide methods of making the compounds of the invention. The compounds may be prepared from readily available materials by the methods outlined in the Reaction Schemes and Examples below, and by obvious modifications thereto.

General Preparation of Compounds of the Invention

Preparation of the biphenyl-4-yl-carbonylamino acid derivatives of the present invention, having Formula (I), may be accomplished by the Methods and Reaction Schemes described below. Methods for the preparation of specific compounds having Formula (II), (III), (IV), (VI), (XI), (XII), and (XIII) are also described in the experimental procedures that follow below.

Compounds of Formula (V) wherein 'A' is a benzo moiety may be prepared by the methods described in PCT/US04/14036 and by other methods known in the art, such as the following: (a) 2-chloro-5-cyanobenzothiazole and 2-chloro-6-cyanobenzothiazole (WO 2002/000633); (b) 5-acetamido-2-chlorobenzothiazole (Sharpe, et al., J. Med. Chem. 15:523-529, 1972); (c) 6-acetamido-2-chlorobenzothiazole (Katz, J. Am. Chem. Soc. 73:4007-4010, 1951); (d) 2-chloro-5-benzothiazole-carboxamide, 2-chloro-N-methyl-6-benzothiazolecarboxamide, 2-chloro-N-ethyl-5-benzothiazolecarboxamide, 2-chloro-N,N-dimethyl-5-benzothiazolecarboxamide, 2-chloro-N,N-dimethyl-6-benzothiazolecarboxamide, 2-chloro-N-(2-hydroxyethyl)-5-benzothiazolecarboxamide, 2-chloro-N-(2-hydroxyethyl)-6-benzothiazolecarboxamide, and 2-chloro-7-morpholinocarbonyl-benzothiazole (U.S. Pat. No. 3,654,296); (e) 6-butoxy-2-chloro-benzothiazole (Bordi, et al., Farmaco 49:153-166, 1994); (f) 2-chloro-6-isopropoxy-benzothiazole, 2-chloro-5-cyano-benzoxazole, and 5-cyano-2-methylthiobenzothiazole (Eur. Patent Appl. EP1308439A1); (g) 2-chloro-5-methylsulfonylbenzoxazole (Lok, et al., J. Org. Chem. 61:3289-3297, 1996); (h) 2-chloro-5-cyanobenzoxazole (Eur. Pat. Appl. EP1308439A1). Compounds of Formula (V) wherein 'A' is a heteroaryl moiety such as a pyrido or pyrimido moiety may be prepared by methods known in the art, such as described for the following compounds and intermediates related to Formula (V): (a) 2-chloro[1,3]thiazolo[4,5-b]pyridine (Viviani, et al., Bull. Soc. Chim. Fr. 130:395-404, 1993); (b) 2-chloro-5-methyl[1,3]thiazolo[4,5-b]pyridine (U.S. Pat. No. 5,496,816); (c) [1,3]thiazolo[5,4-b]pyridine-2-thiol (U.S. Pat. No. 5,077,287); (d) [1,3]thiazolo[5,4-c]pyridine-2-thiol and [1,3]thiazolo[4,5-c]pyridine-2-thiol (WO 2003/039258); and (e) 6-chloro[1,3]thiazolo[4,5-b]pyridine-2-thiol (WO 2003/006470).

Unless otherwise specified, Q, A, and $R^1$-$R^{11}$ have the identical meanings as described above.

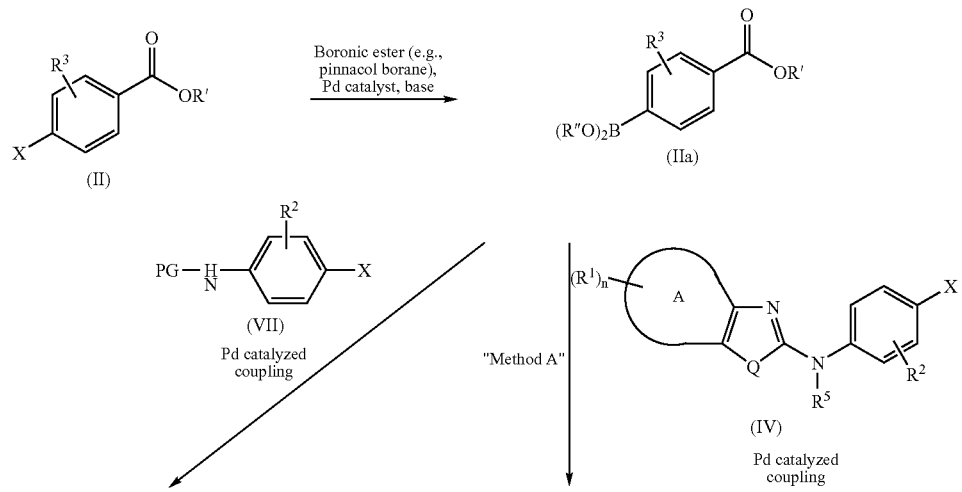

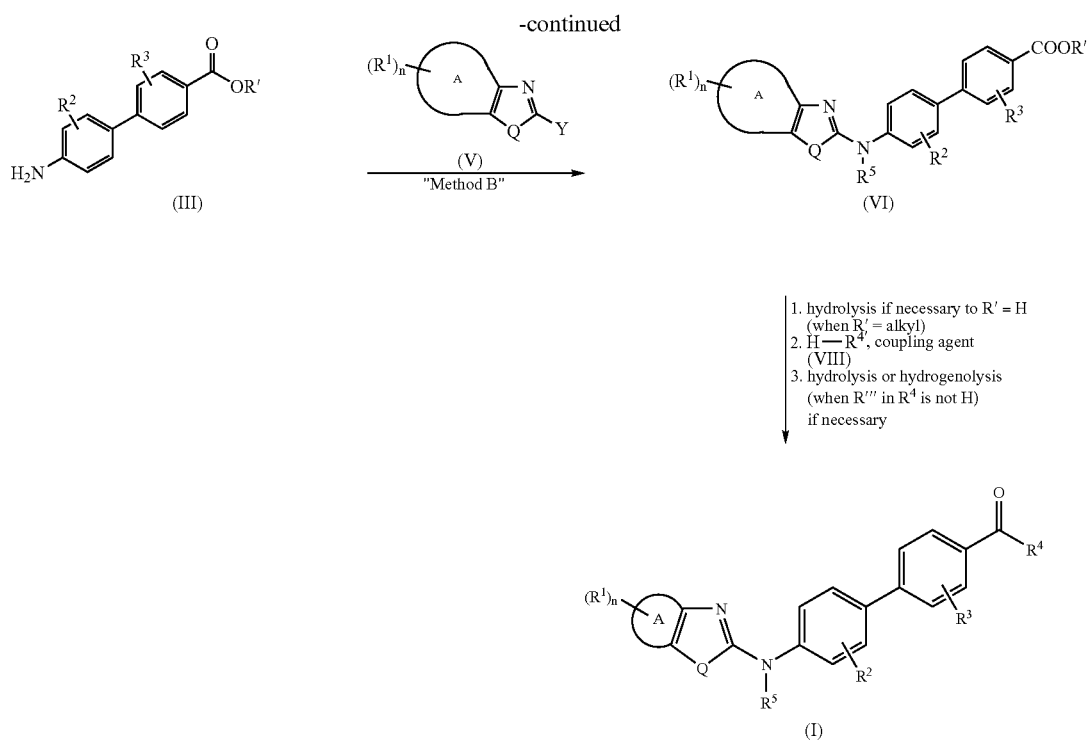

R' = H or alkyl
X = Cl, Br, or I
Y = Cl, Br, I, or SO$_2$alkyl
R'' = H or alkyl, or the two R'' may be linked together such that (R''O)$_2$B forms a ring fragment
PG = an optional protecting group

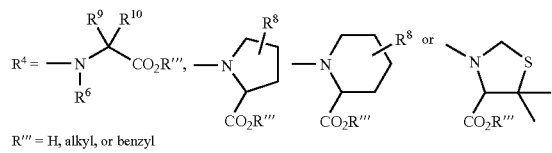

R''' = H, alkyl, or benzyl

In Reaction Scheme 1, a boronic ester derivative of Formula (IIa) is prepared by reaction of the compound of Formula (II), where X=halo, a Pd catalyst, and a boronic ester (e.g., pinnacol borane). The compound of Formula (VI) may then be prepared by "Method A" by coupling the compound of Formula (Ia), with the compound of Formula (IV) in the presence of a palladium catalyst and a base such as potassium carbonate (Suzuki conditions).

Alternatively, the Formula (IIa) compound may be coupled with an aniline of Formula (VII), also under Suzuki conditions, to provide the biphenyl compound of Formula (III). The compound of Formula (VI) may then be prepared by Method B, by reaction of the Formula (III) compound with the compound of Formula (V), in the optional presence of a acid catalyst (e.g., HCl).

Further reaction of the compound of Formula (VI), where R' is H, with an amino acid derivative of Formula (VI), where R$^{4'}$ is

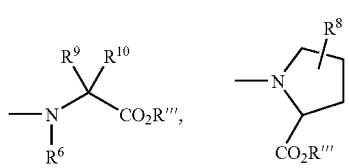

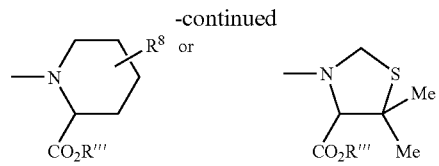

in the optional presence of a coupling agent such as N,N'-diisopropylcarbodiimide, provides an intermediate that is either hydrolyzed (where R''' is alkyl) under basic conditions such as LiOH, THF, and water, or hydrogenated (where R''' is benzyl) using H$_2$ and a suitable catalyst, to give the invention compound of Formula (I).

The intermediate of Formula (III), used in Method B, may also be prepared by the alternative methods outlined in Reaction Scheme 2.

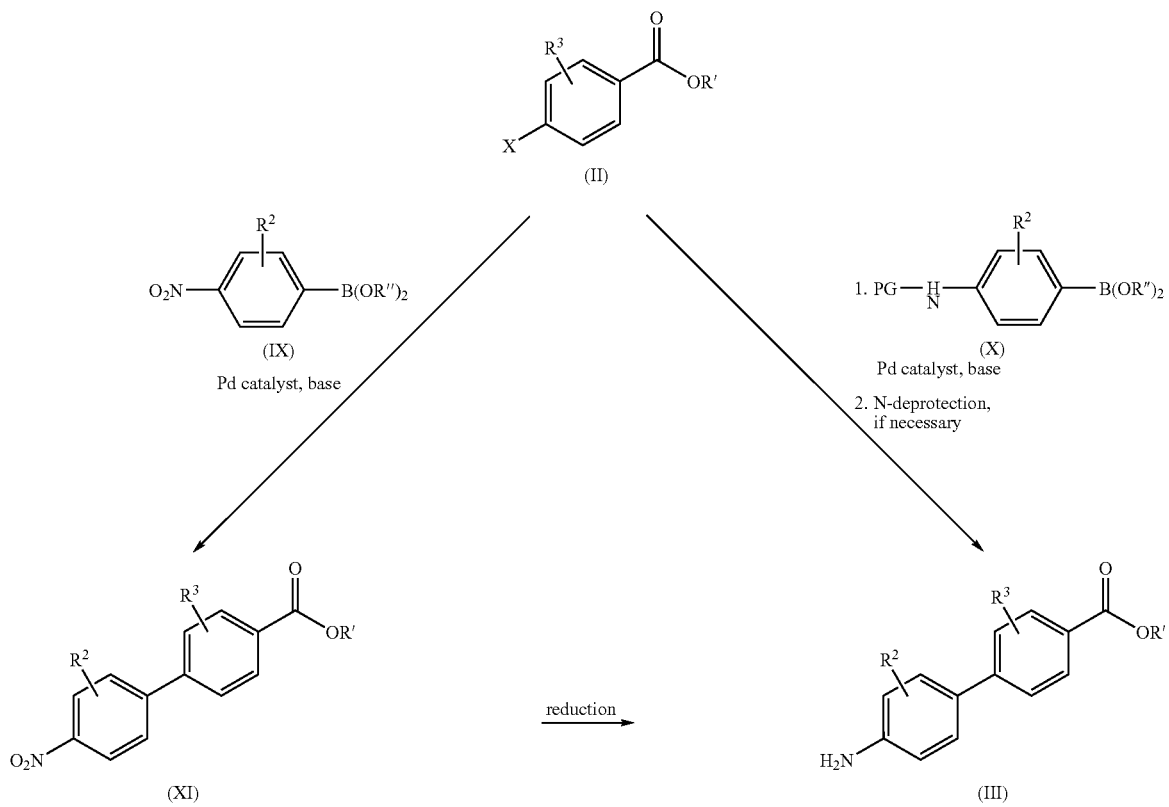

R' = H or alkyl
X = Cl, Br, or I
R" = H or alkyl, or the two R" may be linked together such that (R"O)₂B forms a ring fragment
PG = an optional protecting group For example, the compound of Formula (II) may be coupled with a nitrophenylboronic acid derivative of Formula (IX) under Suzuki conditions (Pd catalyst and base) to give the compound of Formula (XI). Reduction of the Formula (XI) intermediate (e.g., $H_2$ Pd/C or Fe/HCl) gives the aminobiphenyl compound Formula (II). Alternatively, the Formula (II) compound may be coupled with a protected aminoboronic acid derivative of Formula (X), to give, following removal of the protecting group, the intermediate of Formula (III).

Preparation of the Formula (I) Compounds May Also be Accomplished by Method C, as illustrated in Reaction Scheme 3.

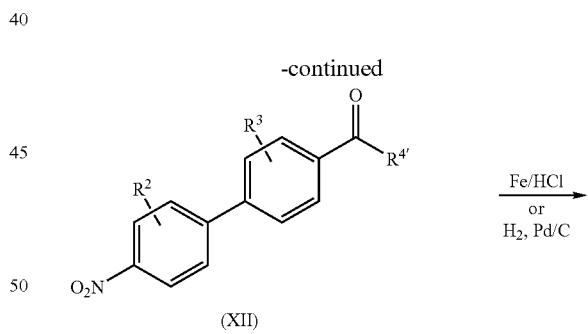

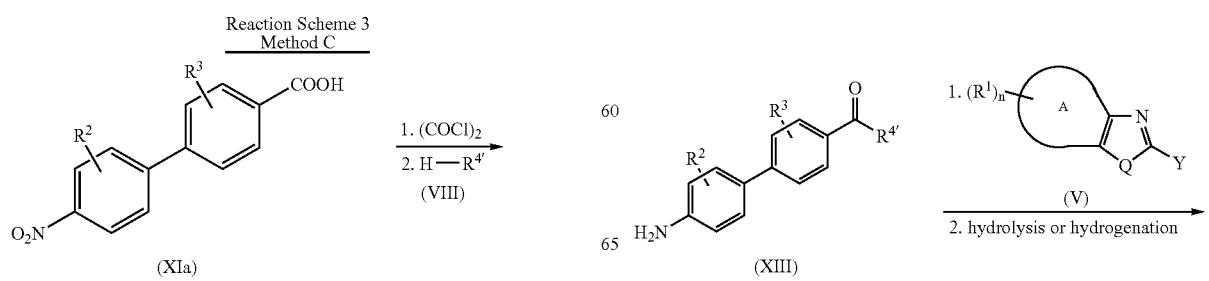

-continued

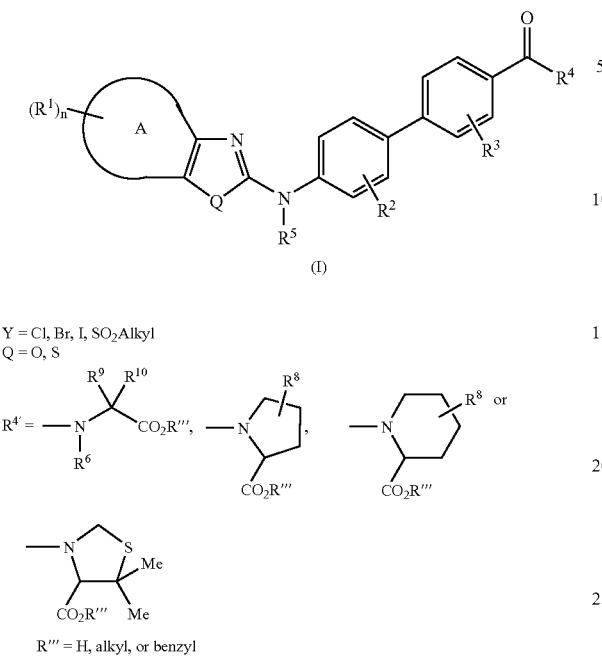

(I)

Y = Cl, Br, I, SO₂Alkyl
Q = O, S

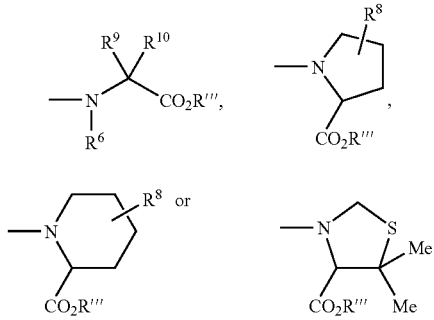

R''' = H, alkyl, or benzyl

In this route, a nitrobiphenyl compound of Formula (XIa) is converted to the Formula (XII) compound by conversion of (XIa) to the corresponding acid chloride (e.g., using $(COCl)_2$) followed by coupling with the amino acid derivative of Formula (VIII), where $R^{4'}$ is

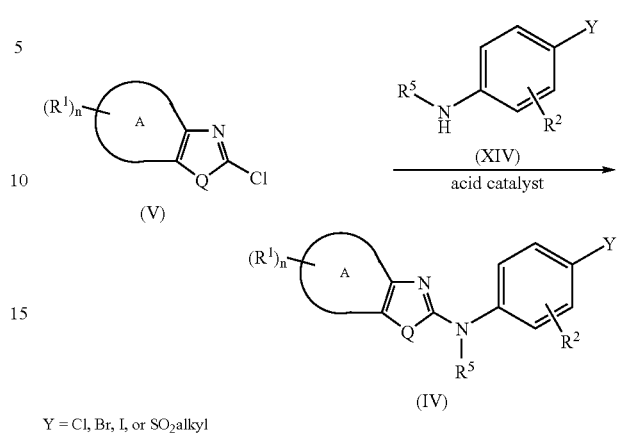

Reaction Scheme 4

(V)

(XIV)

acid catalyst (IV)

Y = Cl, Br, I, or SO₂alkyl in the optional presence of a base. Alternatively, the compound of Formula (XII) can be prepared by reacting (XIa) and (VIII) in the presence of a coupling agent such as dicyclohexylcarbodiimide or other standard coupling agents. The nitro group in the compound of Formula (XII) is then reduced with, for example, $H_2$ and Pd/C or Fe/HCl, to produce the intermediate compound of Formula (XIII). Reaction of (XIII) with the compound of Formula (V) in the presence of an acid catalyst (e.g., HCl) followed by hydrolysis or hydrogenation as in Reaction Scheme 1, gives the invention compound of Formula (I).

Compounds of Formula (IV) are prepared as illustrated in Reaction Scheme 4, by reaction of an aniline of Formula (XIV) with the intermediate of Formula (V), for example, under acid conditions (e.g., HCl in n-butanol) at 90° C.

Specific embodiments of the invention may be found in the Examples described below and in Tables 1-7. The compounds described in these Examples and Tables are intended to be representative of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Preparation of Compounds of the Invention

Mass Spectra

Chemical ionization mass spectra (CI-MS) were obtained with a Hewlett Packard 5989A mass spectrometer equipped with a Hewlett Packard 5890 Gas Chromatograph with a J & W DB-5 column (0.25 uM coating; 30 m×0.25 mm). The ion source was maintained at 250° C. and spectra were scanned from 50-800 amu at 2 sec per scan.

Liquid chromatography—electrospray mass spectra (LC-MS) data were obtained by using a Hewlett-Packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluants were A: 2% acetonitrile in water with 0.02% TFA, and B: 2% water in acetonitrile with 0.018% TFA. Gradient elution from 10% B to 95% B over 3.5 minutes at a flow rate of 1.0 mL/min was used with an initial hold of 0.5 minutes and a final hold of 0.5 minutes at 95% B. Total run time was 6.5 minutes. In the Examples and Tables provided below, the LC-MS data are given with HPLC retention times (ret. time).

NMR Spectra

Routine one-dimensional NMR spectroscopy was performed on 300 MHz or 400 MHz Varian Mercury-plus spectrometers. The samples were dissolved in deuterated solvents obtained from Cambridge Isotope Labs, and transferred to 5 mm ID Wilmad NMR tubes. The spectra were acquired at 293° K. The chemical shifts were recorded on the ppm scale and were referenced to the appropriate solvent signals, such as 2.49 ppm for DMSO-$d_6$, 1.93 ppm for $CD_3CN$, 3.30 ppm for $CD_3OD$, 5.32 ppm for $CD_2Cl_2$, and 7.26 ppm for $CDCl_3$ for $^1$H spectra; and 39.5 ppm for DMSO-$d_6$, 1.3 ppm for CD$_3$CN, 49.0 ppm for CD$_3$OD, 53.8 ppm for CD$_2$Cl$_2$ and 77.0 ppm for CDCl$_3$ for $^{13}$C spectra.

Abbreviations and Acronyms

When the following abbreviations are used throughout this disclosure, they have the following meaning:

| | |
|---|---|
| Ala | alanine |
| Biotage ® | medium-pressure silica gel chromatography, using apparatus from Biotage Inc./Dyax Corp. |
| CDCl$_3$ | deuterated chloroform |
| Celite ® | diatomaceous earth filter agent, obtained from Celite Corp. |
| DCE | dichloroethane |
| DCM | dichloromethane |
| DMF | N,N-dimethylformamide |
| DMSO | dimethyl sulfoxide |
| ee | enantiomeric excess |
| EI-MS | electron impact - mass spectroscopy |
| h | hour(s) |
| HPLC | high pressure liquid chromatography |
| Ile | isoleucine |
| LC-MS | liquid chromatography - mass spectroscopy |
| Leu | leucine |
| min | minutes |
| MS | mass spectroscopy |
| NMR | nuclear magnetic resonance |
| Phe | phenylalanine |
| p.o. | orally |
| Pro | proline |
| rt | room temperature |
| THF | tetrahydrofuran |
| TLC | thin layer chromatography |
| TFA | trifluoroacetic acid |
| Val | valine |

By using the described methods herein, the compounds of the invention may be prepared. The following examples are presented to further illustrate the invention described herein, but they should not be construed as limiting the scope of the invention in any way.

Preparation of Intermediates

Compounds of Formula (II)

Intermediate II-1: Methyl 4-bromo-2-methoxybenzoate

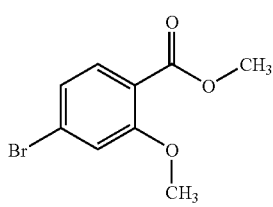

Step 1. Preparation of 4-bromo-2-hydroxybenzoic Acid

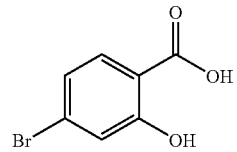

t-Butyl nitrite (5.10 g, 49.5 mmol) was added to a suspension of copper(II) bromide (8.80 g, 39.4 mmol) in CH$_3$CN (50 mL), and the reaction mixture was cooled to 0° C. in an ice bath. 4-Aminosalicylic acid (5.00 g, 32.7 mmol) was added in small portions over 30 min. Additional CH$_3$CN (20 mL) was added, and the reaction mixture was allowed to stir at 0° C. for 2 h. The reaction mixture was poured into 20% HCl (200 mL) and extracted with Et$_2$O (2×200 mL). The combined organic phases were washed with 20% HCl (2×100 mL), dried over MgSO$_4$, filtered, and concentrated in vacuo. The residue was dissolved in Et$_2$O (300 mL) and extracted with 15% NaOH (2×150 mL). The combined aqueous layers were washed with Et$_2$O (100 mL), brought to pH 1 with 20% HCl, and extracted with Et$_2$O (3×200 mL). The combined organic phases were dried over MgSO$_4$, filtered, and concentrated in vacuo. The resulting solid was triturated with CHCl$_3$ and collected by filtration, yielding 2.5 g (35%) of the title compound as a crystalline solid. The material was used without further characterization or purification.

Step 2. Preparation of methyl 4-bromo-2-methoxybenzoate

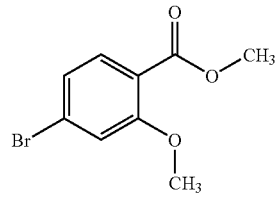

4-Bromo-2-hydroxybenzoic acid (1.00 g, 4.61 mmol) was dissolved in acetone (25 mL), and iodomethane (1.15 mL, 18.4 mmol) and K$_2$CO$_3$ (2.55 g, 18.4 mmol) were added. The reaction was heated at reflux overnight. Upon cooling to it, the reaction mixture was filtered, and the filtrate was concentrated in vacuo. The crude material was purified by flash chromatography (Biotage® column; 10% EtOAc/Hexanes), yielding 0.955 g (85%) of the desired product as a yellow oil. LC/MS m/z 245.0 (MH$^+$); retention time 3.13 min. $^1$H NMR (400 MHz, CD$_2$Cl$_2$) δ 3.84 (s, 3H), 3.90 (s, 3H), 7.12-7.20 (m, 2H), 7.62 (d, 1H).

Intermediate II-2: Methyl 4-bromo-2-methylbenzoate

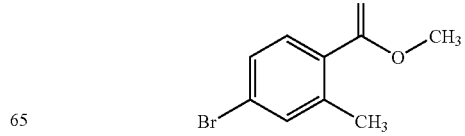

4-Bromo-2-methylbenzoic acid (2.00 g, 9.30 mmol) was added to a solution of acetyl chloride (1.70 mL, 23.9 mmol) in methanol (30 mL). The mixture was allowed to stir at rt for 3 days and was then concentrated in vacuo. This gave 1.96 g (92%) of the title compound as a light brown oil. $^1$H NMR (400 MHz, CD$_2$Cl$_2$) δ2.61 (s, 3H), 3.90 (s, 3H), 7.38-7.42 (m, 2H), 7.78 (d, 1H).

Intermediate II-3: Methyl 4-bromo-2-chlorobenzoate

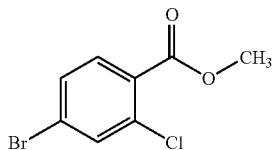

4-Bromo-2-chlorobenzoic acid (1.00 g, 4.25 mmol) was added to a solution of acetyl chloride (1.70 mL, 23.9 mmol) in methanol (30 mL). The mixture was allowed to stir at rt for 3 days, and was then concentrated in vacuo. This gave 0.84 g (80%) of the title compound. $^1$H NMR (400 MHz, CD$_2$Cl$_2$) δ 3.85 (s, 3H), 7.51 (d, 1H), 7.45 (d, 1H), 7.78 (d, 1H).

Preparation of Intermediate Compounds of Formula (III)

Intermediate III-1: Methyl 4'-amino-3-methylbiphenyl-4-carboxylate

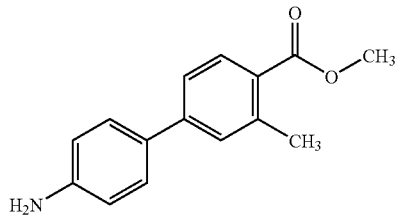

Step 1. Preparation of methyl 3-methyl-4'-nitrobiphenyl-4-carboxylate

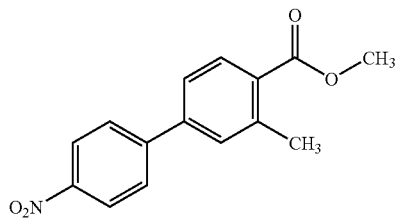

To a solution of methyl 4-bromo-2-methylbenzoate (1.00 g, 4.37 mmol) and 4-nitrophenylboronic acid (2.91 g, 17.5 mmol) in toluene (12 mL) was added Na$_2$CO$_3$ (3.70 g, 34.9 mmol), 1,1'-bis(diphenylphosphino)ferrocenepalladium(II) chloride complex with dichloromethane (0.71 g, 0.87 mmol), 1,4-dioxane (6 mL), and water (6 mL). The mixture was heated at reflux for 3 h and then allowed to cool to rt. The mixture was diluted with EtOAc and water, and the organic layer was isolated, dried over MgSO$_4$, and concentrated in vacuo. The material was purified by column chromatography (25% EtOAc in hexanes), yielding 1.32 g (89%) of the title compound. GC/MS m/z 271 (M$^+$); retention time 13.00 min. $^1$H NMR (400 MHz, CD$_2$Cl$_2$) δ2.65 (s, 3H), 3.95 (s, 3H), 7.52 (d, 2H), 7.78 (d, 2H), 8.11 (d, 1H), 8.30-8.39 (m, 2H).

Step 2. Preparation of methyl 4'-amino-3-methylbiphenyl-4-carboxylate

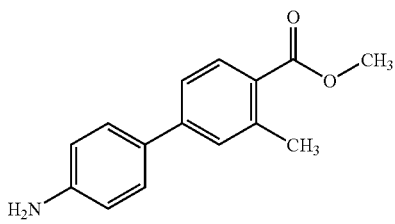

Iron powder (1.04 g, 18.6 mmol) was added to a solution of methyl 3-methyl-4'-nitrobiphenyl-4-carboxylate (0.63 g, 1.9 mmol) in ethanol (20 mL). Concentrated HCl (0.93 mL, 1.9 mmol) was added, and the mixture was heated at reflux for 3 h. Upon cooling to rt, the mixture was filtered through a pad of Celite®, and the filtrate was concentrated in vacuo. The material was purified by column chromatography (33% EtOAc in hexanes), yielding 0.338 g (75%) of the title compound. LC/MS m/z 242.3 (MH$^+$); retention time 2.27 min. $^1$H NMR (400 MHz, CD$_2$Cl$_2$) δ2.81 (s, 3H), 3.95 (s, 3H), 6.83 (d, 2H), 7.41-7.51 (m, 4H), 7.85 (d, 1H).

Intermediate III-2: Methyl 4'-amino-3-chlorobiphenyl-4-carboxylate

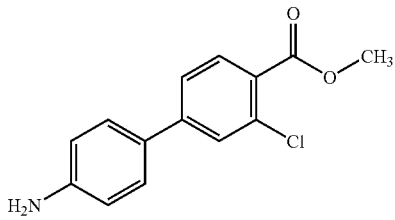

Step 1. Preparation of methyl 3-chloro-4'-nitrobiphenyl-4-carboxylate

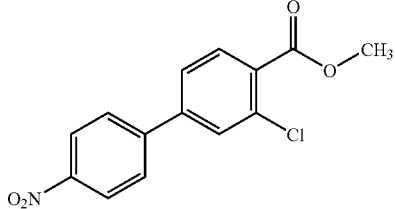

To a solution of methyl 4-bromo-2-chlorobenzoate (0.40 g, 1.6 mmol) and 4-nitrophenylboronic acid (0.67 g, 4.0 mmol) in toluene (8 mL) was added Na$_2$CO$_3$ (1.02 g, 9.62 mmol), 1,1'-bis(diphenylphosphino)ferrocenepalladium(II) chloride complex with dichloromethane (0.03 g, 0.03 mmol), 1,4-dioxane (4 mL), and water (4 mL). The mixture was heated at reflux for 3 h and then allowed to cool to rt. The mixture was diluted with EtOAc and water, and the organic layer was isolated, dried over MgSO$_4$, and concentrated in vacuo. The material was purified by column chromatography (25% EtOAc in hexanes), yielding 0.275 g (59%) of the title compound. $^1$H NMR (400 MHz, CD$_2$Cl$_2$) δ 3.98 (s, 3H), 7.58 (d, 2H), 7.68-7.82 (m, 3H), 7.97 (d, 1H), 8.33 (d, 1H).

Step 2. Preparation of methyl 4'-amino-3-chlorobiphenyl-4-carboxylate

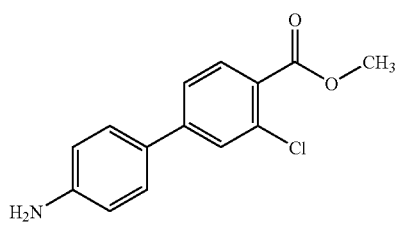

Iron powder (0.99 g, 17.7 mmol) was added to a solution of methyl 3-chloro-4'-nitrobiphenyl-4-carboxylate (0.64 g, 1.8 mmol) in ethanol (15 mL). Concentrated HCl (0.88 mL, 1.8 mmol) was added, and the mixture was heated at reflux for 3 h. Upon cooling to rt, the mixture was filtered through a pad of Celite®, and the filtrate was concentrated in vacuo. The material was purified by column chromatography (33% EtOAc in hexanes), yielding 0.453 g (98%) of the title compound. LC/MS m/z 262.4 (Mob; retention time 2.39 min. $^1$H NMR (400 MHz, CD$_2$Cl$_2$) δ 3.99 (s, 3H), 6.78 (d, 2H), 7.41-7.46 (m, 3H), 7.62 (s, 1H), 7.88 (d, 1H).

Intermediate III-3: Methyl 4'-amino-3-methoxybiphenyl-4-carboxylate

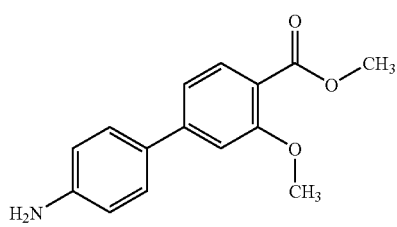

Step 1. Preparation of methyl 3-methoxy-4'-nitrobiphenyl-4-carboxylate

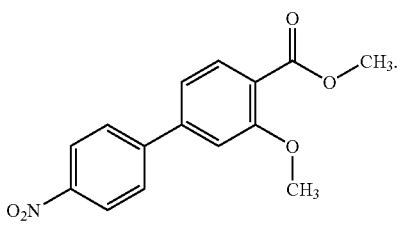

To a solution of methyl 4-bromo-2-methoxybenzoate (0.95 g, 3.9 mmol) and 4-nitrophenylboronic acid (1.29 g, 7.75 mmol) in toluene (10 mL) was added Na$_2$CO$_3$ (1.85 g, 17.4 mmol), 1,1-bis(diphenylphosphino)ferrocenepalladium(II) chloride complex with dichloromethane (0.06 g, 0.08 mmol), 1,4-dioxane (5 mL), and water (5 mL). The mixture was heated at reflux for 3 h and then allowed to cool to rt. The mixture was diluted with EtOAc and water, and the organic layer was isolated, dried over MgSO$_4$, and concentrated in vacuo. The material was purified by column chromatography (25% EtOAc in hexanes), yielding 0.675 g (61%) of the title compound. LC/MS m/z 287.9 (MH$^+$); retention time 3.14 min.

Step 2. Preparation of methyl 4'-amino-3-methoxybiphenyl-4-carboxylate

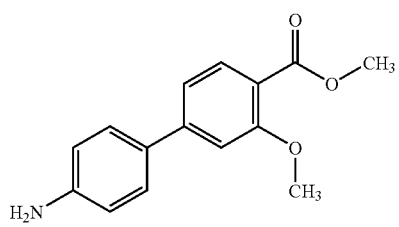

Iron powder (0.58 g, 10 mmol) was added to a solution of methyl 3-methoxy-4'-nitrobiphenyl-4-carboxylate (0.38 g, 1.0 mmol) in ethanol (10 mL). Concentrated HCl (0.52 mL, 1.0 mmol) was added, and the mixture was heated at reflux for 3 h. Upon cooling to rt, the mixture was filtered through a pad of Celite®, and the filtrate was concentrated in vacuo. The material was purified by column chromatography (33% EtOAc in hexanes), yielding 0.279 g (quantitative yield) of the title compound. LC/MS m/z 258.3 (MH$^+$); retention time 1.65 min. $^1$H NMR (400 MHz, CD$_2$Cl$_2$) δ3.81 (s, 3H), 3.99 (s, 3H), 6.78 (d, 2H), 7.15-7.19 (m, 2H), 7.45 (d, 2H), 7.80 (d, 1H).

Preparation of Intermediate Compounds of Formula (IV)

Intermediate IV-1: N-(4-bromophenyl)-6-fluoro-1,3-benzothiazol-2-amine

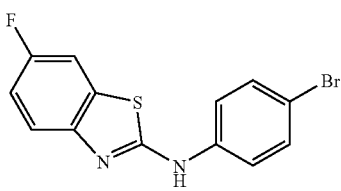

Step 1. Preparation of 2-chloro-6-fluoro-benzothiazole

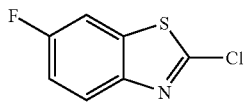

6-Fluoro-benzothiazole-2-thiol was treated with sulfuryl chloride by the procedure described in PCT/US04/14036 to give the desired product, which was used in the next step without further purification. EI-MS m/z 187 (M$^+$); $^1$H NMR (DMSO-d$_6$) δ 8.00 (m, 2H), 7.40 (m, 1H).

Step 2. Preparation of N-(4-bromophenyl)-6-fluoro-1,3-benzothiazol-2-amine

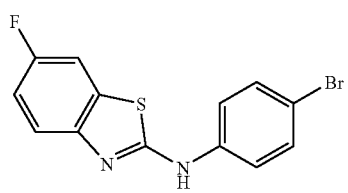

A mixture of 2-chloro-6-fluoro-benzothiazole (0.65 g, 3.5 mmol) and 4-bromoaniline (0.61 g, 3.5 mmol) in n-butanol (6 mL) was heated at 60-70° C. under nitrogen to obtain a solution, to which 4 M HCl in dioxane (0.43 mL, 1.73 mmol) was slowly added dropwise. The reaction mixture was then heated at 90° C. for 18 h. Upon cooling to rt, the reaction mixture was concentrated under reduced pressure. The resulting solid was triturated with ethanol and collected by filtration. This yielded 0.98 g (88%) of the title compound. LC/MS m/z 323.0 (MH$^+$); retention time 3.74 min. $^1$H NMR (CD$_3$OD) δ 7.10-7.30 (m, 1H), 7.39 (d, 1H), 7.45 (d, 2H), 7.58-7.61 (m, 3H).

Intermediate IV-2: N-(4-bromo-2-fluoro-phenyl)-6-fluoro-1,3-benzothiazol-2-amine

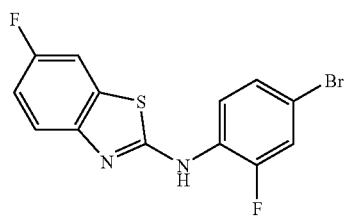

In a similar manner to the procedure described above for the preparation of N-(4-bromophenyl)-6-fluoro-1,3-benzothiazol-2-amine, 2-chloro-6-fluoro-benzothiazole and 2-fluoro-4-bromoaniline were reacted together to provide N-(4-bromo-2-fluoro-phenyl)-6-fluoro-1,3-benzothiazol-2-amine as a solid. $^1$H NMR (DMSO-d$_6$) δ 10.50 (s, 1H), 8.60 (t, 1H), 7.80 (d, 1H), 7.60 (m, 2H), 7.40 (d, 1H), 7.20 (m, 1H)).

Intermediate IV-3: N-(4-bromophenyl)-6-chloro-1,3-benzothiazol-2-amine

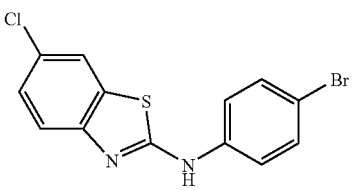

A mixture of 2,6-dichlorobenzothiazole (0.71 g, 3.5 mmol) and 4-bromoaniline (0.61 g, 3.5 mmol) in n-butanol (6 mL) was heated at 60-70° C. under nitrogen to obtain a solution, to which 4 M HCl in dioxane (0.43 mL, 1.73 mmol) was then slowly added dropwise. The reaction mixture was then heated at 90° C. for 18 h. Upon cooling to rt, the reaction mixture was concentrated under reduced pressure. The resulting solid was triturated with ethanol and collected by filtration. This yielded 1.09 g (93%) of the title compound. LC/MS m/z 339 (MH$^+$); retention time 3.98 min. $^1$H NMR (CD$_3$OD) δ 7.31 (d, 1H), 7.42-7.58 (m, 5H), 7.61 (d, 1H).

Intermediate IV-4: N-(4-bromo-2-fluorophenyl)-6-(trifluoromethoxy)-1,3-benzothiazol-2-amine

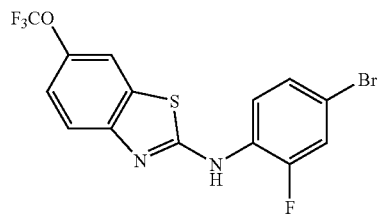

The preparation of this intermediate is described in US 2004/0224997.

Intermediate IV-5: N-(4-bromo-2-fluorophenyl)-6-isopropyl-1,3-benzothiazol-2-amine

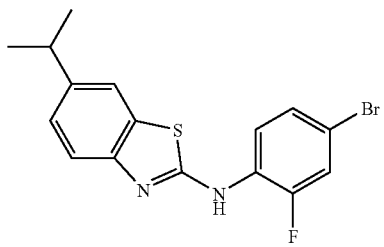

The preparation of this intermediate is described in US 2004/0224997.

Intermediate IV-6: N-(4-bromo-2-fluorophenyl)-6-(trifluoromethyl)-1,3-benzothiazol-2-amine

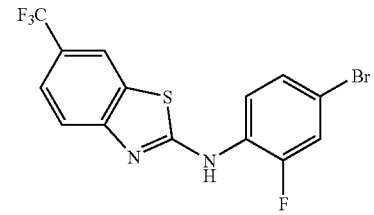

The preparation of this intermediate is described in US 2004/0224997.

Intermediate IV-7: N-(4-bromophenyl)-6-(trifluoromethyl)-1,3-benzothiazol-2-amine

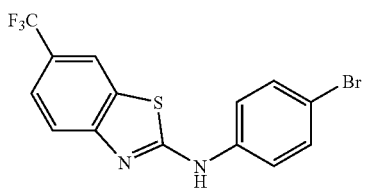

This intermediate was prepared by the methods described in US 2004/0224997.

Preparation of Intermediate Compounds of Formula (VI) by Method a

Intermediate VI-1: 3'-Fluoro-4'-[(6-fluoro-1,3-benzothiazol-2-yl)amino]biphenyl-4-carboxylic Acid

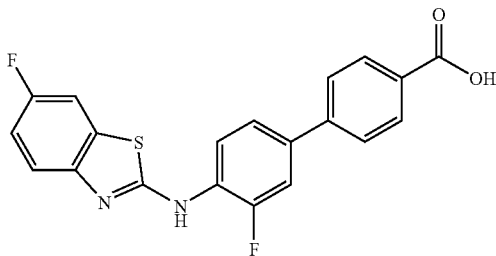

The preparation of 3'-fluoro-4'-[(6-fluoro-1,3-benzothiazol-2-yl)amino]biphenyl-4-carboxylic acid is described below in Reaction Scheme 5.

Step 1. Preparation of methyl 3'-fluoro-4'-[(6-fluoro-1,3-benzothiazol-2-yl)amino]biphenyl-4-carboxylate

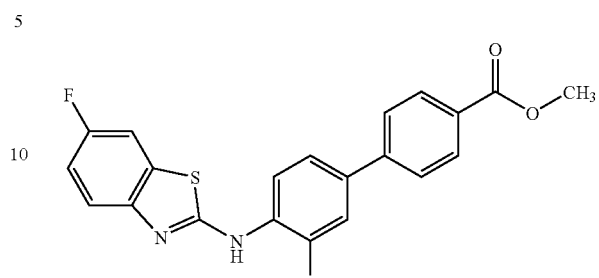

As shown in Reaction Scheme 5, to a mixture of N-(4-bromo-2-fluorophenyl)-6-fluoro-1,3-benzothiazol-2-amine (1.00 g, 2.93 mmol) and 4-(methoxycarbonylphenyl)boronic acid (0.79 g, 4.40 mmol) in toluene (10 mL) was added Na$_2$CO$_3$ (1.40 g, 13.2 mmol), 1,1'-bis(diphenylphosphino)ferrocenepalladium(II) chloride complex with dichloromethane (0.05 g, 0.06 mmol), 1,4-dioxane (5 mL), and water (5 mL). This mixture was heated at reflux overnight. Upon cooling to rt, the reaction mixture was filtered, and the solid was washed with water (2×30 mL) and methanol (2×30 mL). The solid was recrystallized from acetone/MeOH (2:1). This yielded 0.641 g (55%) of the desired product as an off-white solid. $^1$H NMR (400 MHz, DMSO-d$_6$) δ 3.82 (s, 3H), 7.20 (t, 1H), 7.59-8.02 (m, 8H), 8.70 (t, 1H), 10.50 (bs, 1H).

Step 2. Preparation of 3'-fluoro-4'-[(6-fluoro-1,3-benzothiazol-2-yl)amino]biphenyl-4-carboxylic Acid As shown in Reaction Scheme 5, methyl 3'-fluoro-4'-[(6-fluoro-1,3-benzothiazol-2-yl)amino]biphenyl-4-carboxylate (0.64 g, 1.6 mmol) was suspended in THF (10 mL), MeOH (10 mL) and water (5 mL), and LiOH (0.39 g, 16.2 mmol) was added. The reaction mixture was heated at 50° C. until dissolution was achieved, and then the mixture was stirred for 3 days at rt. The reaction mixture was brought to pH 4 with 1N HCl and was extracted with EtOAc (3×25 mL). The combined organic phases were washed with water (2×50 mL) and brine (50 mL), dried over MgSO$_4$, filtered, and concentrated in vacuo. This yielded 0.518 g (84%) of the desired product as an off-white solid. LC/MS m/z 383.3 (MH$^+$), retention time 3.83 min. $^1$H NMR (400 MHz, DMSO-d$_6$) δ 7.18 (t, 1H), 7.59-8.00 (m, 8H), 8.70 (t, 1H), 10.50 (bs, 1H), 12.95 (bs, 1H).

Reaction Scheme 5

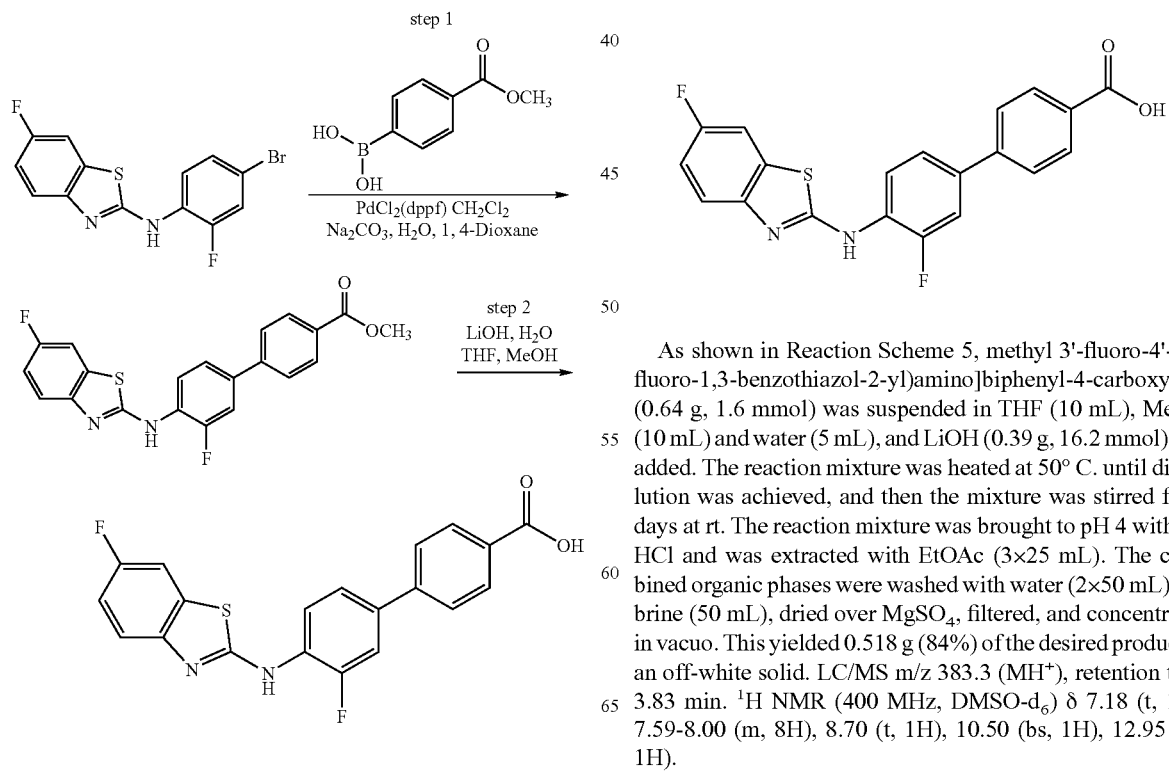

Intermediate VI-2: 3'-Fluoro-4'-[(6-fluoro-1,3-benzothiazol-2-yl)amino]-3-methyl biphenyl-4-carboxylic Acid

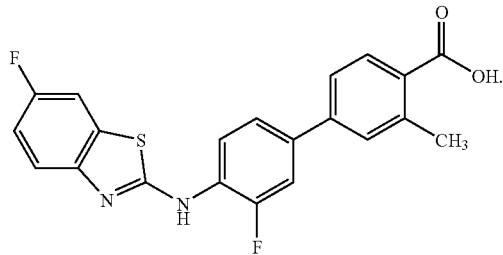

The preparation of 3'-fluoro-4'-[(6-fluoro-1,3-benzothiazol-2-yl)amino]-3-methylbiphenyl-4-carboxylic acid is described below in Reaction Scheme 6.

As shown in Reaction Scheme 6, a mixture of bis(pinacolato)diboron (0.55 g, 2.2 mmol), methyl 4-bromo-2-methylbenzoate (0.50 g, 2.2 mmol), palladium(II) acetate (0.01 g, 0.07 mmol), and KOAc (0.64 g, 6.6 mmol) in DMF (7.5 mL) was degassed with argon for 30 min at rt. The mixture was then heated at 80° C. for 4 h. After cooling the mixture to rt, N-(4-bromo-2-fluorophenyl)-6-fluoro-1,3-benzothiazol-2-amine (0.74 g, 2.2 mmol), tetrakis(triphenylphosphine)palladium(0) (0.08 g, 0.07 mmol), and saturated aqueous $NaHCO_3$ (5 mL) were added. The mixture was heated at 85° C. overnight. The mixture was poured into ice water and extracted with EtOAc. The combined organic phases were dried over $Na_2SO_4$, concentrated in vacuo, and purified by column chromatography (20% EtOAc in hexanes). This yielded 0.345 g (39%) of the title compound. LC/MS m/z 411.3 ($MH^+$; retention time 4.15 min. $^1H$ NMR (400 MHz, $CD_2Cl_2$) δ2.62 (s, 3H), 3.90 (s, 3H), 7.10 (t, 1H), 7.39-7.53 (m, 5H), 7.62-7.70 (m, 1H), 7.99 (d, 1H), 8.58 (t, 1H).

Reaction Scheme 6

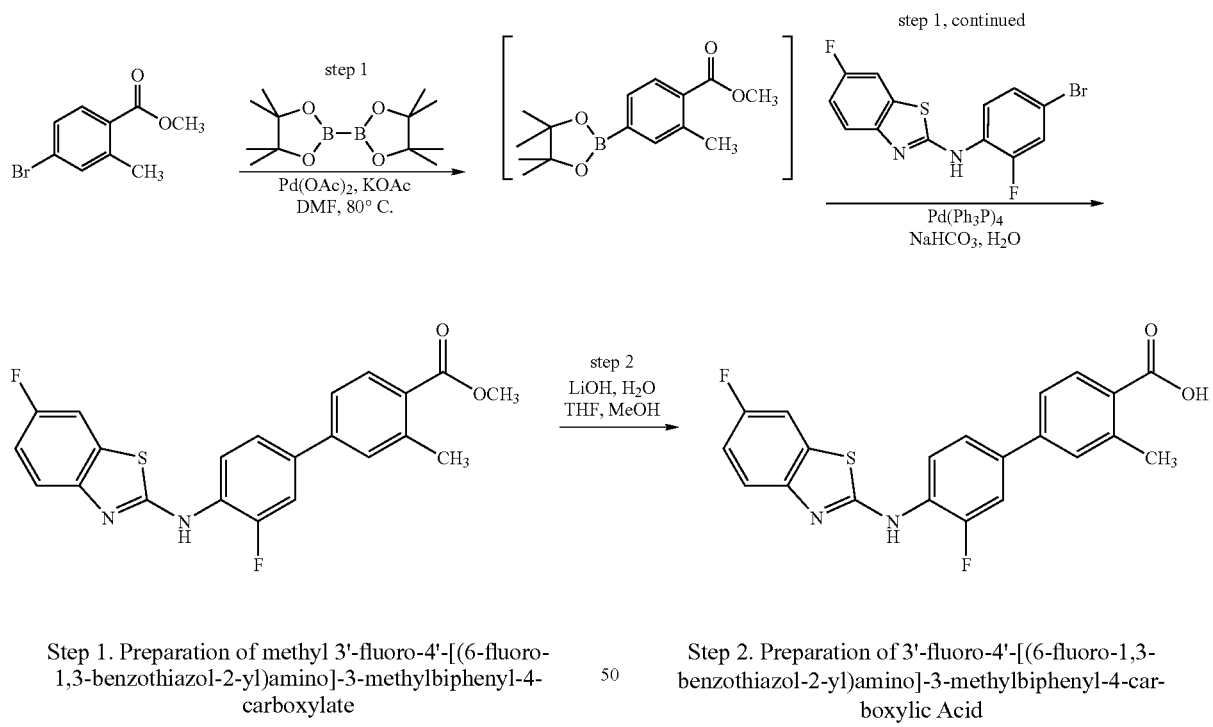

Step 1. Preparation of methyl 3'-fluoro-4'-[(6-fluoro-1,3-benzothiazol-2-yl)amino]-3-methylbiphenyl-4-carboxylate Step 2. Preparation of 3'-fluoro-4'-[(6-fluoro-1,3-benzothiazol-2-yl)amino]-3-methylbiphenyl-4-carboxylic Acid

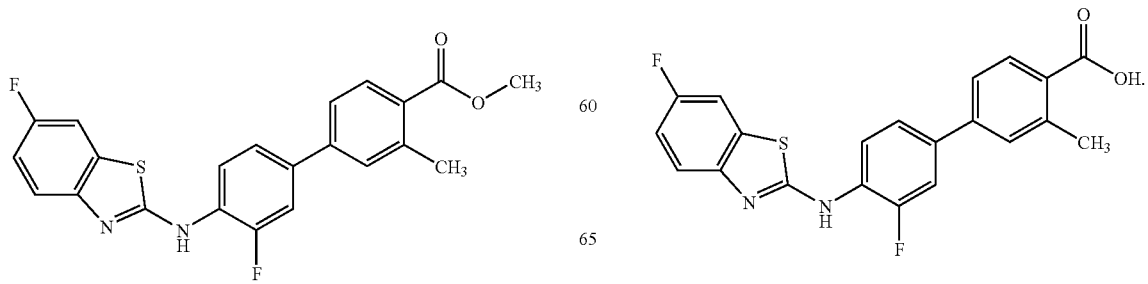

As shown in Reaction Scheme 6, methyl 3'-fluoro-4'-[(6-fluoro-1,3-benzothiazol-2-yl)amino]-3-methylbiphenyl-4-carboxylate (0.38 g, 0.67 mmol) was suspended in THF (5 mL), MeOH (5 mL), and water (2.5 mL), and NaOH (0.27 g, 6.7 mmol) was added. The reaction mixture was heated at 50° C. for 3 h. Upon cooling to rt, the reaction mixture was concentrated in vacuo, acidified with 2N HCl, and the resulting solid was collected by filtration. This yielded 0.33 g (quantitative) of the title compound. $^1$H NMR (400 MHz, DMSO-$d_6$) §2.62 (s, 3H), 7.10 (t, 1H), 7.49-7.58 (m, 5H), 7.65-7.75 (m, 1H), 8.10 (d, 1H), 8.58 (t, 1H), 10.85 (br, 1H).

Intermediate VI-3: 4'-[(6-Fluoro-1,3-benzothiazol-2-yl)amino]biphenyl-4-carboxylic Acid

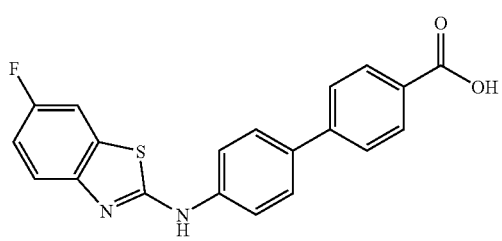

Step 1. Preparation of methyl 4'-[(6-fluoro-1,3-benzothiazol-2-yl)amino]biphenyl-4-carboxylate

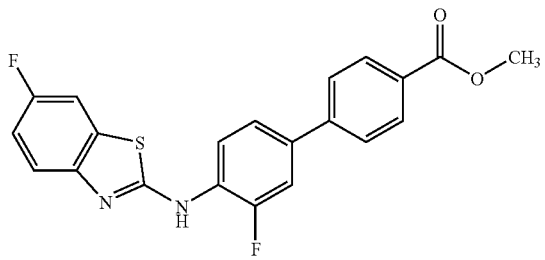

A mixture of bis(pinacolato)diboron (0.35 g, 1.4 mmol), methyl 4-bromobenzoate (0.30 g, 1.4 mmol), palladium(II) acetate (0.01 g, 0.04 mmol), and KOAc (0.41 g, 4.2 mmol) in DMF (7.5 mL) was degassed with argon for 30 min at rt. The mixture was then heated at 80° C. for 4 h. After the mixture was cooled to rt, N-(4-bromophenyl)-6-fluoro-1,3-benzothiazol-2-amine (0.45 g, 1.4 mmol), tetrakis(triphenylphosphine)palladium(0) (0.05 g, 0.04 mmol), and saturated aqueous NaHCO$_3$ (5 mL) were added. The mixture was heated at 85° C. overnight. Upon cooling to rt, the mixture was diluted with EtOAc. The combined organic phases were separated, dried over Na$_2$SO$_4$, and concentrated in vacuo. Purification by column chromatography (25% EtOAc in hexanes) yielded 0.094 g (18%) of the title compound. LC/MS m/z 379.3 (MH$^+$); retention time 3.87 min. $^1$H NMR (400 MHz, CD$_3$OD) δ 3.93 (s, 3H), 7.05 (t, 1H), 7.39-7.81 (m, 8H), 8.03 (d, 2H).

Step 2. Preparation of 4'-[(6-fluoro-1,3-benzothiazol-2-yl)amino]biphenyl-4-carboxylic Acid

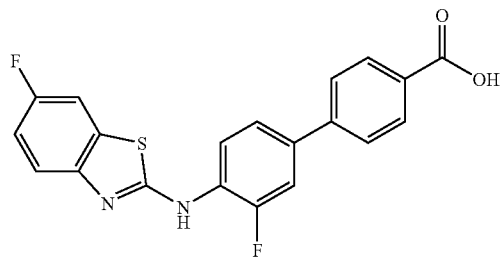

Methyl 4'-[(6-fluoro-1,3-benzothiazol-2-yl)amino]biphenyl-4-carboxylate (94 mg, 0.25 mmol) was suspended in THF (3 mL), MeOH (3 mL), and water (1.5 mL), and NaOH (0.10 g, 2.5 mmol) was added. The reaction mixture was heated at 50° C. for 3 h. Upon cooling to rt, the reaction mixture was concentrated in vacuo, acidified with 2N HCl, and the resulting solid was collected by filtration. This yielded 90 mg (99%) of the title compound. LC/MS m/z 365.2 (MH$^+$), retention time 3.46 min. $^1$H NMR (400 MHz, DMSO-$d_6$) δ 7.08 (t, 1H), 7.49-7.80 (m, 6H), 7.82-8.01 (m, 4H), 10.75 (br, 1H).

Intermediate VI-4: 3'-Fluoro-4'-[(6-fluoro-1,3-benzothiazol-2-yl)amino]-3-methoxy biphenyl-4-carboxylic Acid

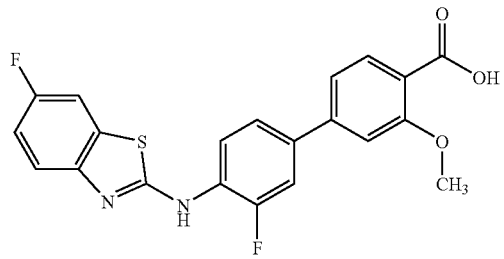

Step 1. Preparation of methyl 3'-fluoro-4'-[(6-fluoro-1,3-benzothiazol-2-yl)amino]-3-methoxy biphenyl-4-carboxylate

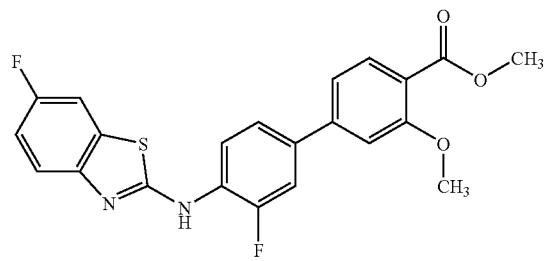

A mixture of bis(pinacolato)diboron (1.40 g, 5.51 mmol), methyl 4-bromo-2-methoxybenzoate (1.35 g, 5.51 mmol), palladium(1) acetate (0.04 g, 0.17 mmol), and KOAc (1.62 g, 16.5 mmol) in DMF (10 mL) was degassed with argon for 30 min at rt. The mixture was then heated at 80° C. for 4 h. After the mixture was cooled to rt, N-(4-bromo-2-fluorophenyl)-6-fluoro-1,3-benzothiazol-2-amine (1.88 g, 5.51 mmol), tetrakis(triphenylphosphine)palladium(0) (0.19 g, 0.17 mmol), and saturated aqueous NaHCO$_3$ (5 mL) were added. The mixture was heated at 85° C. overnight. The mixture was poured into ice water and extracted with EtOAc. The combined organic phases were dried over MgSO$_4$, concentrated in vacuo, and purified by column chromatography (25% EtOAc in hexanes). This yielded 0.431 g (18%) of the title compound. LC/MS m/z 427.3 (MH$^+$), retention time 3.82 min. $^1$H NMR (400 MHz, CD$_2$Cl$_2$) δ 3.81 (s, 3H), 4.03 (s, 3H), 7.19-7.23 (m, 3H), 7.41-7.64 (m, 4H), 7.82 (d, 1H), 8.31 (t, 1H).

Step 2. Preparation of 3'-fluoro-4'-[(6-fluoro-1,3-benzothiazol-2-yl)amino]-3-methoxy biphenyl-4-carboxylic Acid

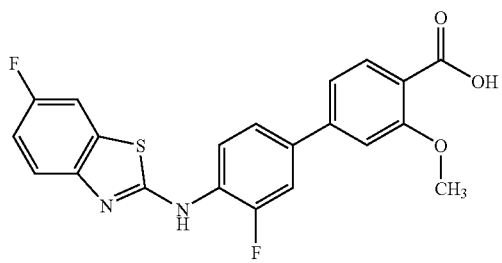

Methyl 3'-fluoro-4'-[(6-fluoro-1,3-benzothiazol-2-yl)amino]-3-methoxybiphenyl-4-carboxylate (0.43 g, 1.01 mmol) was suspended in THF (10 mL), MeOH (5 mL) and water (5 mL), and NaOH (0.40 g, 10 mmol) was added. The reaction mixture was stirred at rt for 18 h. The reaction mixture was concentrated under reduced pressure, acidified with 2N HCl, and the resulting solid was collected by filtration. This yielded 0.41 g (99%) of the title compound as a light brown solid. LC/MS m/z 413.3 (MH$^+$), retention time 3.44 min. $^1$H NMR (400 MHz, DMSO-d$_6$) δ 3.91 (s, 3H), 7.17 (t, 1H), 7.24-7.29 (m, 2H), 7.58-7.78 (m, 5H), 8.63 (t, 1H), 10.45 (br, 1H).

Preparation of Intermediate Compounds of Formula (VI) by Method B

Intermediate VI-5: 4'-[(6-Fluoro-1,3-benzothiazol-2-yl)amino]-3-methylbiphenyl-4-carboxylic Acid

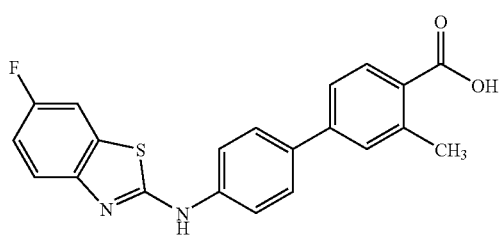

The preparation of 4'-[(6-fluoro-1,3-benzothiazol-2-yl)amino]-3-methylbiphenyl-4-carboxylic acid is described below in Reaction Scheme 7.

Reaction Scheme 7

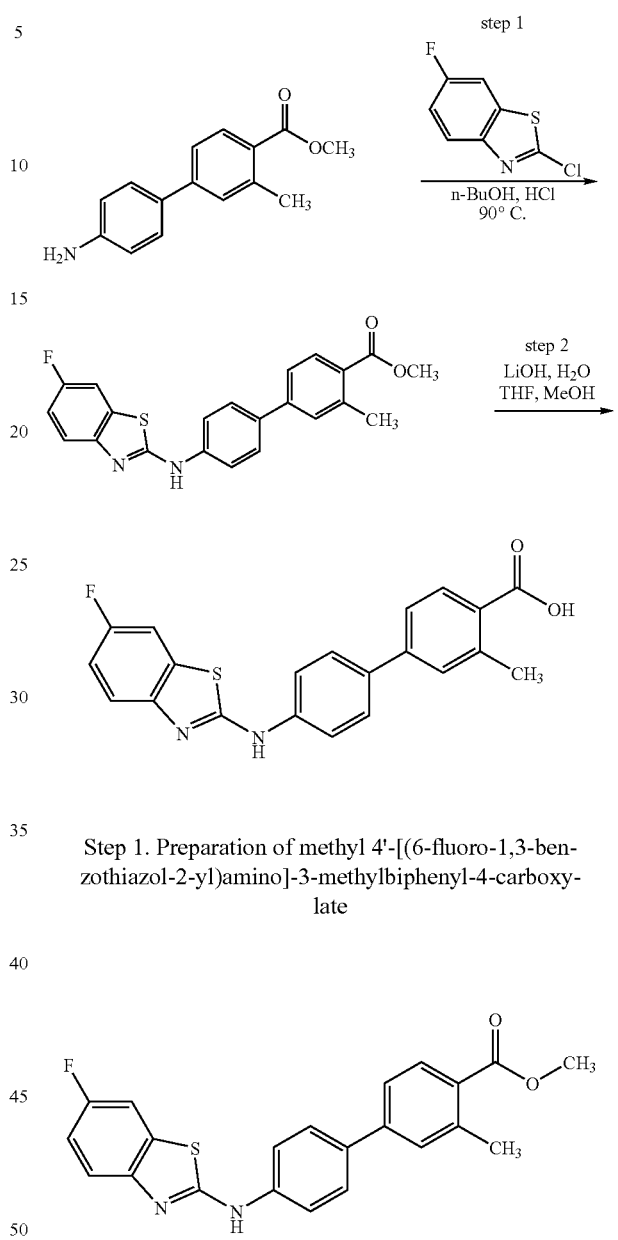

Step 1. Preparation of methyl 4'-[(6-fluoro-1,3-benzothiazol-2-yl)amino]-3-methylbiphenyl-4-carboxylate

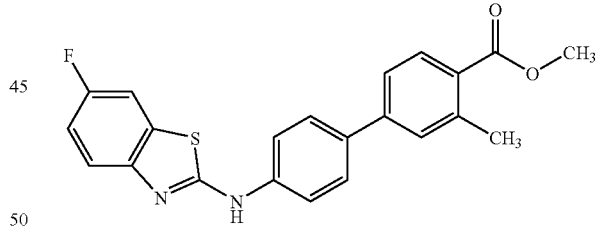

As shown in Reaction Scheme 7, a mixture of methyl 4'-amino-3-methylbiphenyl-4-carboxylate (0.34 g, 1.40 mmol) and 2-chloro-6-fluoro-1,3-benzothiazole (0.26 g, 1.40 mmol) in n-butanol (4 mL) was heated to 60-70° C., and then 4N HCl in 1,4-dioxane (0.16 mL, 0.63 mmol) was added dropwise with stirring. The reaction mixture was heated at 90° C. for 18 h. Upon cooling to rt, the reaction mixture was concentrated in vacuo. The residue was triturated with ethanol and collected by filtration, yielding 0.32 g (58%) of the title compound as a pale yellow solid. LC/MS m/z 393.3 (MH$^+$), retention time 4.02 min. $^1$H NMR (400 MHz, CD$_2$Cl$_2$) δ 2.62 (s, 3H), 3.95 (s, 3H), 7.05 (t, 1H), 7.39-7.60 (m, 4H), 7.65 (s, 4H), 7.96 (d, 1H).

Step 2. Preparation of 4'-[(6-fluoro-1,3-benzothiazol-2-yl)amino]-3-methylbiphenyl-4-carboxylic Acid

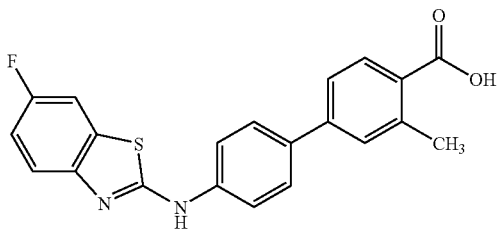

As shown in Reaction Scheme 7, methyl 4'-[(6-fluoro-1,3-benzothiazol-2-yl)amino]-3-methylbiphenyl-4-carboxylate (0.25 g, 0.65 mmol) was suspended in THF (5 mL), MeOH (5 mL) and water (2.5 mL), and NaOH (0.26 g, 6.5 mmol) was added. The reaction mixture was heated at 50° C. for 3 h. Upon cooling to rt, the reaction mixture was concentrated in vacuo, acidified with 2N HCl, and the resulting solid was collected by filtration. This yielded 0.25 g (quantitative) of the title compound. $^1$H NMR (400 MHz, DMSO-$d_6$) δ 2.62 (s, 3H), 7.05 (t, 1H), 7.57-7.90 (m, 9H), 10.62 (br, 1H)

Intermediate VI-6: 4'-[(6-Fluoro-1,3-benzothiazol-2-yl)amino]-3-methoxybiphenyl-4-carboxylic Acid

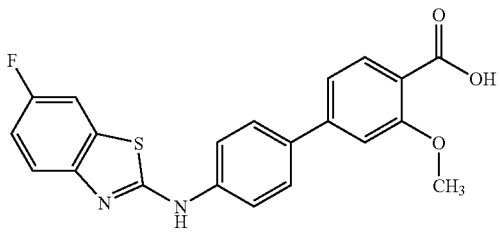

Step 1. Preparation of butyl 4'-[(6-fluoro-1,3-benzothiazol-2-yl)amino]-3-methoxybiphenyl-4-carboxylate and methyl 4'-[(6-fluoro-1,3-benzothiazol-2-yl)amino]-3-methoxybiphenyl-4-carboxylate

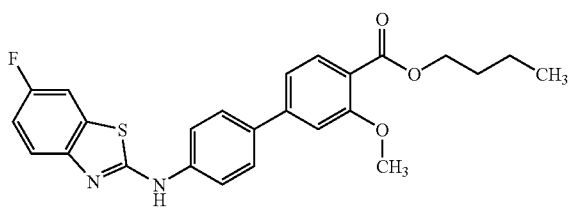

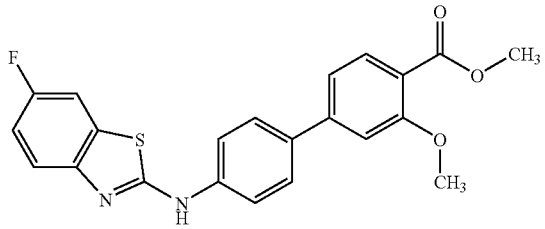

A mixture of methyl 4'-amino-3-methoxybiphenyl-4-carboxylate (0.27 g, 1.06 mmol) and 2-chloro-6-fluoro-1,3-benzothiazole (0.20 g, 1.06 mmol) in n-butanol (8 mL) was heated to 60-70° C., and then 4N HCl in 1,4-dioxane (0.12 mL, 0.48 mmol) was added dropwise with stirring. The reaction mixture was heated at 90° C. for 18 h. Upon cooling to rt, the reaction mixture was concentrated under reduced pressure. The residue was purified by column chromatography (25% EtOAc in hexanes), yielding 0.209 g (44%) of butyl 4'-[(6-fluoro-1,3-benzothiazol-2-yl)amino]-3-methoxybiphenyl-4-carboxylate, and 0.132 g (30%) of methyl 4'-[(6-fluoro-1,3-benzothiazol-2-yl)amino]-3-methoxybiphenyl-4-carboxylate [LC/MS m/z 409.3 (MH$^+$), retention time=3.67 min, m/z 451.3 (MH$^+$), retention time=4.25 min. $^1$H NMR (400 MHz, CD$_2$Cl$_2$) δ 3.85 (s, 3H), 4.00 (s, 3H), 7.05-7.26 (m, 3H), 7.42 (d, 1H), 7.61-7.64 (m, 1H), 7.76 (s, 4H), 7.90 (d, 1H)].

Step 2. Preparation of 4'-[(6-fluoro-1,3-benzothiazol-2-yl)amino]-3-methoxybiphenyl-4-carboxylic Acid

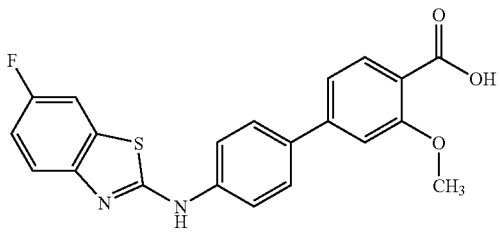

Butyl 4'-[(6-fluoro-1,3-benzothiazol-2-yl)amino]-3-methoxybiphenyl-4-carboxylate (0.30 g, 0.43 mmol) and methyl 4'-[(6-fluoro-1,3-benzothiazol-2-yl)amino]-3-methoxybiphenyl-4-carboxylate (0.13 g, 0.25 mmol) were combined in THF (6 mL), MeOH (6 mL) and water (3 mL), and then NaOH (0.09 g, 2.1 mmol) was added. The reaction mixture was heated at 50° C. for 3 h. Upon cooling to rt, the reaction mixture was concentrated under reduced pressure, acidified, and the resulting solid was collected by filtration. This yielded 0.286 g (87%) of the title compound. LC/MS m/z 395.2 (MH$^+$), retention time 3.30 min. $^1$H NMR (400 MHz, DMSO-$d_6$) δ 3.90 (s, 3H), 7.12-7.33 (m, 3H), 7.61-7.90 (m, 7H), 10.62 (br, 1H).

Intermediate VI-7: 4'-[(6-Fluoro-1,3-benzothiazol-2-yl)amino]-3-chlorobiphenyl-4-carboxylic Acid

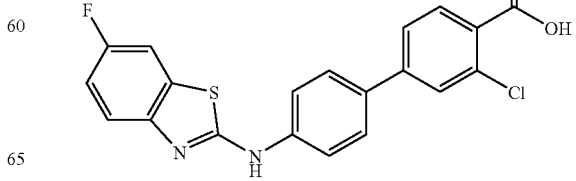

Step 1. Preparation of methyl 4'-[(6-fluoro-1,3-benzothiazol-2-yl)amino]-3-chlorobiphenyl-4-carboxylate

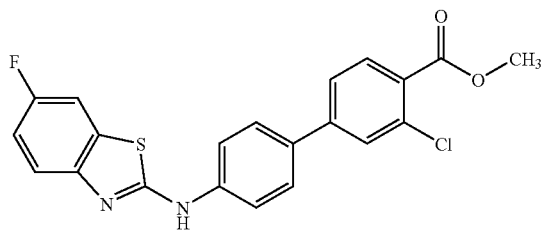

A mixture of methyl 4'-amino-3-chlorobiphenyl-4-carboxylate (0.45 g, 1.7 mmol) and 2-chloro-6-fluoro-1,3-benzothiazole (0.32 g, 1.7 mmol) in n-butanol (8 mL) was heated to 60-70° C., and then 4N HCl in 1,4-dioxane (0.19 mL, 0.77 mmol) was added dropwise with stirring. The reaction mixture was heated at 90° C. for 18 h. Upon cooling to rt, the reaction mixture was concentrated under reduced pressure. The residue was triturated with ethanol, and the solid was collected by filtration. This yielded 0.399 g (56%) of the title compound as a beige solid. LC/MS m/z 411 (MH$^+$), retention time 4.03 min. $^1$H NMR (400 MHz, DMSO-d$_6$) δ 3.85 (s, 3H), 7.12 (t, 1H), 7.67-7.87 (m, 9H), 10.62 (br, 1H).

Step 2. Preparation of 4'-[(6-fluoro-1,3-benzothiazol-2-yl)amino]-3-chlorobiphenyl-4-carboxylic Acid

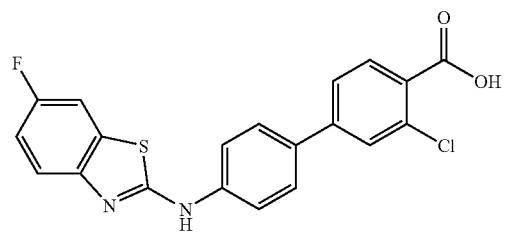

Methyl 4'-[(6-fluoro-1,3-benzothiazol-2-yl)amino]-3-chlorobiphenyl-4-carboxylate (0.30 g, 0.71 mmol) was suspended in THF (5 mL), MeOH (5 mL) and water (2.5 mL), and then NaOH (0.28 g, 7.1 mmol) was added. The reaction mixture was heated at 50° C. for 3 h. Upon cooling to rt, the reaction mixture was concentrated under reduced pressure, acidified, and the resulting solid was collected by filtration. This yielded 0.34 g (quantitative) of the title compound. LC/MS m/z 399.2 (MH$^+$), retention time 3.53 min.

Preparation of Intermediate Compounds of Formula (VI) by Method a

Intermediate VI-8: 3,3'-Difluoro-4'-[(6-fluoro-1,3-benzothiazol-2-yl)amino]biphenyl-4-carboxylic Acid

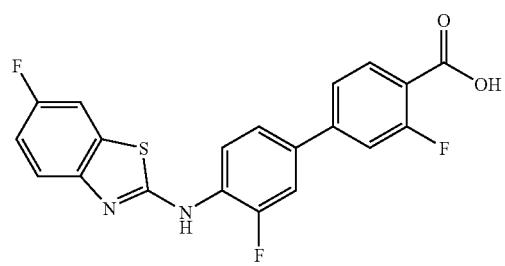

The preparation of 3,3'-difluoro-4'-[(6-fluoro-1,3-benzothiazol-2-yl)amino]biphenyl-4-carboxylic acid is described below in Reaction Scheme 8.

Reaction Scheme 8

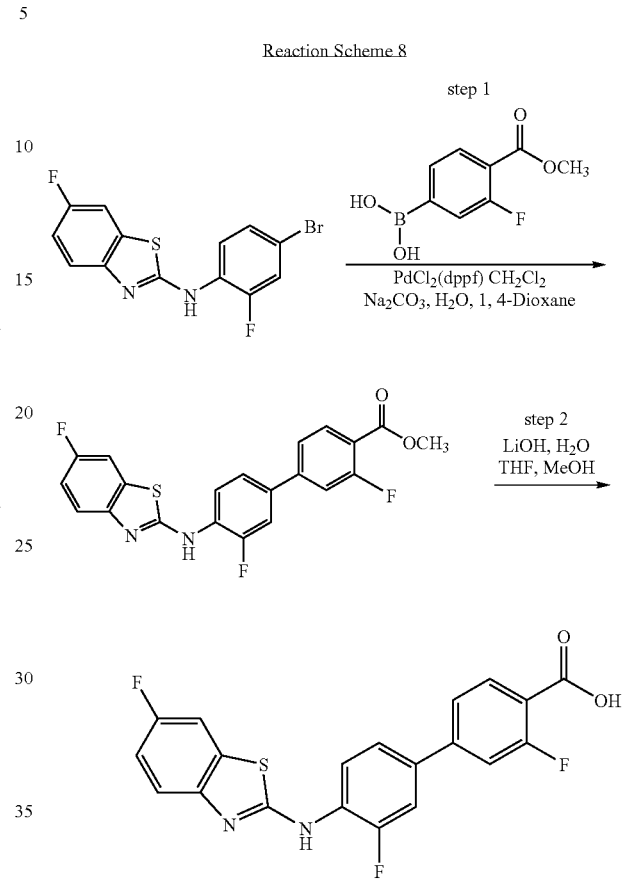

As shown in Reaction Scheme 8, Intermediate VI-8 (3,3'-difluoro-4'-[(6-fluoro-1,3-benzothiazol-2-yl)amino]biphenyl-4-carboxylic acid) was prepared using a method similar to that employed in the preparation of Intermediate VI-1 using N-(4-bromo-2-fluorophenyl)-6-fluoro-1,3-benzothiazol-2-amine and commercially available [3-fluoro-4-(methoxycarbonyl)phenyl]boronic acid as starting materials.

Intermediate VI-9: 3-Fluoro-4'-[(6-fluoro-1,3-benzothiazol-2-yl)amino]biphenyl-4-carboxylic Acid

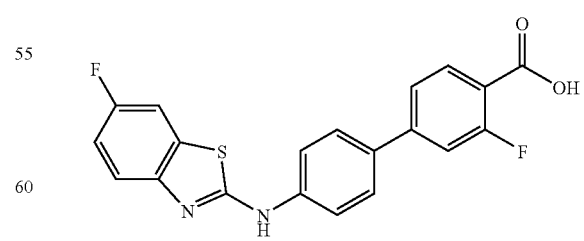

The preparation of 3-fluoro-4'-[(6-fluoro-1,3-benzothiazol-2-yl)amino]biphenyl-4-carboxylic acid is described below in Reaction Scheme 9.

Reaction Scheme 9

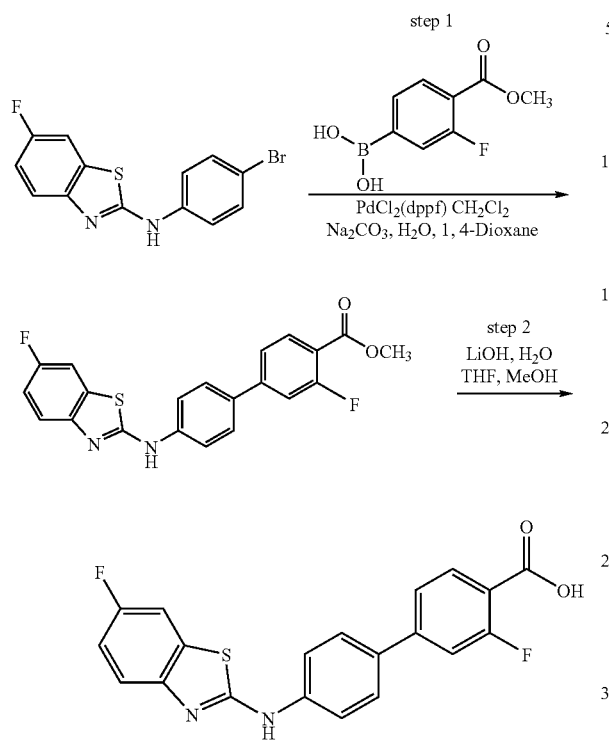

As shown in Reaction Scheme 9, Intermediate VI-9 (3-fluoro-4'-[(6-fluoro-1,3-benzothiazol-2-yl)amino]biphenyl-4-carboxylic acid) was prepared using a method similar to that employed in the preparation of Intermediate VI-1 using N-(4-bromophenyl)-6-fluoro-1,3-benzothiazol-2-amine and commercially available [3-fluoro-4-(methoxycarbonyl)phenyl]boronic acid as starting materials.

Preparation of Compounds of Formula (VII)

Intermediate VIII-1: Methyl D-leucinate Hydrochloride

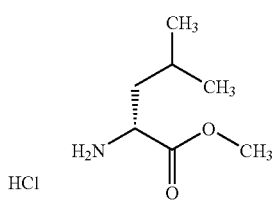

D-Leucine (3.00 g, 22.9 mmol) was added to a solution of acetyl chloride (1.70 mL, 23.9 mmol) in methanol (30 mL). The reaction mixture was allowed to stir for 18 h and then concentrated under reduced pressure. This yielded 3.8 g (91%) of the title compound. $^1$H NMR (400 MHz, CD$_3$OD) δ 0.99 (dd, 6H), 1.63-1.87 (m, 3H), 4.10 (dd, 1H), 3.81 (s, 3H).

Intermediate VIII-2: Methyl 1-aminocyclopentanecarboxylate Hydrochloride

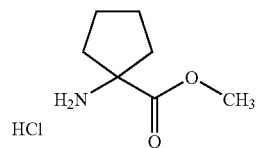

1-Aminocyclopentanecarboxylic acid (1.00 g, 7.74 mmol) was added to a solution of acetyl chloride (0.60 mL, 8.44 mmol) in methanol (10 mL). The reaction mixture was allowed to stir for 18 h and then concentrated under reduced pressure. This yielded 1.35 g (97%) of the title compound. $^1$H NMR (400 MHz, CD$_3$OD) δ 1.80-2.00 (m, 6H), 2.34-2.39 (m, 2H), 3.82 (s, 3H).

Intermediate VIII-3: Methyl-1-aminocyclohexanecarboxylate Hydrochloride

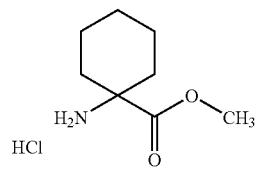

1-Aminocyclohexanecarboxylic acid (1.00 g, 6.98 mmol) was added to a solution of acetyl chloride (0.60 mL, 8.44 mmol) in methanol (10 mL). The reaction mixture was allowed to stir for 18 h and then concentrated under reduced pressure. $^1$H NMR (400 MHz, CD$_3$OD) δ 1.42-1.82 (m, 8H), 2.08-2.20 (m, 2H), 3.82 (s, 3).

Intermediate VIII-4: Methyl L-norvalinate Hydrochloride

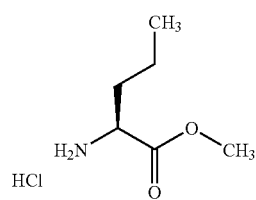

L-Norvaline (0.82 g, 6.98 mmol) was added to a solution of acetyl chloride (0.60 mL, 8.44 mmol) in methanol (10 mL). The reaction mixture was allowed to stir for 18 h and then concentrated under reduced pressure. $^1$H NMR (400 MHz, CD$_3$OD) δ 1.0 (t, 3H), 1.35-1.50 (m, 2H), 1.80-2.00 (m, 2H), 3.82 (s, 3H).

Preparation of Compounds of Formula (I)

Example 1

N-({3'-fluoro-4'-[(6-fluoro-1,3-benzothiazol-2-yl)amino]biphenyl-4-yl}carbonyl)-L-valine

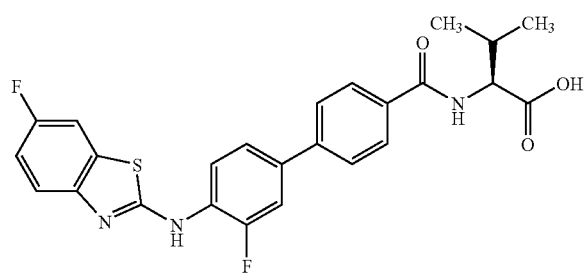

Step 1. Preparation of methyl N-({3'-fluoro-4'-[(6-fluoro-1,3-benzothiazol-2-yl)amino]biphenyl-4-yl}carbonyl)-L-valinate

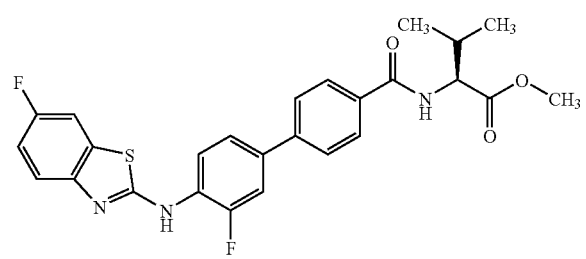

3'-Fluoro-4'-[(6-fluoro-1,3-benzothiazol-2-yl)amino]biphenyl-4-carboxylic acid (0.084 g, 0.22 mmol) and L-valine methyl ester hydrochloride (0.044 g, 0.26 mmol) were suspended in CH$_2$Cl$_2$ (5 mL), and triethylamine (0.04 mL, 0.26 mmol), 1-hydroxybenzotriazole (0.0296 g, 0.22 mmol), and N,N'-diisopropylcarbodiimide (0.030 mL, 0.22 mmol) were added. DMF (2.0 mL) was added to achieve dissolution, and the reaction mixture was stirred at rt overnight. The reaction mixture was diluted with EtOAc (50 mL) and was washed with water (2×50 mL) and brine (50 mL). The combined organic phases were dried over MgSO$_4$, filtered, and concentrated in vacuo. The crude material was purified by flash column chromatography (Biotage® system; 30-40% EtOAc/Hexanes gradient). This yielded 90.4 mg (83%) of the desired product as a white solid.

Step 2. Preparation of N-({3'-fluoro-4'-[(6-fluoro-1,3-benzothiazol-2-yl)amino]biphenyl-4-yl}carbonyl)-L-valine

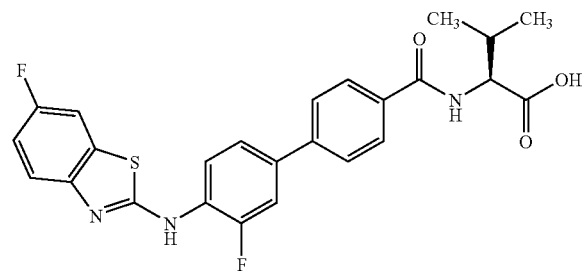

Methyl N-({3'-fluoro-4'-[(6-fluoro-1,3-benzothiazol-2-yl)amino]biphenyl-4-yl}carbonyl)-L-valinate (84.2 mg, 0.17 mmol) was suspended in THF (2.5 mL), MeOH (2.5 mL) and water (1 mL), and LiOH (40.7 mg, 1.70 mmol) was added. The reaction mixture was heated at 50° C. for 2 h. Upon cooling to rt, the reaction mixture was brought to pH 3 with 1N HCl and was extracted with EtOAc (3×25 mL). The combined organic phases were washed with water (2×50 mL) and brine (50 mL), dried over MgSO$_4$, filtered, and concentrated in vacuo. This yielded 72.3 mg (88%) of the title compound as a white solid. LC/MS m/z 482.3 (MH$^+$), retention time 3.46 min. $^1$H NMR (400 MHz, DMSO-d$_6$) δ 0.99 (dd, 6H), 2.19-2.24 (m, 1H), 4.30 (dd, H), 7.18 (t, 1H), 7.60-7.84 (m, 6H), 7.88 (d, 2H), 8.42 (d, 1H), 8.66 (t, 1H), 10.42 (s, 1H).

By using the methods described above and by substituting the appropriate starting materials, compounds of Formula (I), listed in Table 1a below, were similarly prepared.

TABLE 1a

Preparative Examples of Compounds of Formula (I)

| Example No. | R$^1$ | R$^2$ | R$^3$ | R$^4$ | LC-MS Ret. Time (min) | LC-MS [M + H]$^+$ | Method |
|---|---|---|---|---|---|---|---|
| 1 | 6-F | F | H | L-Val-OH | 3.46 | 482.3 | A |
| 2 | 6-F | H | H | L-Ala-OH | 3.50 | 436.3 | A |
| 3 | 6-F | F | H | L-Ala-OH | 3.55 | 454.3 | A |
| 4 | 6-F | H | H | L-Val-OH | 3.72 | 464.3 | A |
| 5 | 6-F | H | Cl | L-Val-OH | 3.46 | 498.2 | B |
| 6 | 6-F | F | CH$_3$ | L-Val-OH | 3.47 | 496.2 | A |
| 7 | 6-F | F | OMe | L-Val-OH | 3.60 | 512.4 | A |
| 8 | 6-F | H | H | L-Leu-OH | 3.86 | 478.3 | A |
| 9 | 6-F | F | H | L-Leu-OH | 3.93 | 496.3 | A |
| 10 | 6-F | H | OMe | L-Leu-OH | 3.64 | 508.2 | B |
| 11 | 6-F | F | OMe | L-Leu-OH | 3.75 | 526.4 | A |
| 12 | 6-F | H | Cl | L-Leu-OH | 3.62 | 512.2 | B |
| 13 | 6-F | H | CH$_3$ | L-Leu-OH | 3.55 | 492.2 | B |
| 14 | 6-F | F | CH$_3$ | L-Leu-OH | 3.60 | 510.4 | A |
| 15 | 6-F | H | H | D-Leu-OH | 3.48 | 478.2 | A |
| 16 | 6-F | F | H | D-Leu-OH | 3.58 | 496.2 | A |
| 17 | 6-F | H | H | L-Ile-OH | 3.52 | 478.2 | A |
| 18 | 6-F | F | H | L-Ile-OH | 3.64 | 496.4 | A |
| 19 | 6-F | F | OMe | L-Ile-OH | 3.75 | 526.4 | A |
| 20 | 6-F | H | H | L-Phe-OH | 3.85 | 512.3 | A |
| 21 | 6-F | F | H | L-Phe-OH | 3.93 | 530.2 | A |
| 22 | 6-F | H | OMe | L-Phe-OH | 3.63 | 508.2 | B |
| 23 | 6-F | H | CH$_3$ | L-Phe-OH | 3.51 | 526.2 | A |
| 24 | 6-F | F | CH$_3$ | L-Phe-OH | 3.61 | 544.3 | A |
| 25 | 6-F | H | Cl | L-Phe-OH | 3.60 | 546.1 | B |
| 26 | 6-F | H | H | L-Pro-OH | 3.52 | 462.2 | A |
| 27 | 6-F | F | H | L-Pro-OH | 3.58 | 480.2 | A |
| 28 | 6-F | H | OMe | L-Pro-OH | 3.20 | 492.1 | B |
| 29 | 6-F | H | Cl | L-Pro-OH | 3.32 | 496.1 | B |
| 30 | 6-F | H | CH$_3$ | L-Pro-OH | 3.52 | 476.1 | B |
| 31 | 6-F | F | CH$_3$ | L-Pro-OH | 3.31 | 494.3 | A |

TABLE 1b

IUPAC Names for Compounds in Table 1a

| Example No. | IUPAC Name |
|---|---|
| 1 | N-({3'-fluoro-4'-[(6-fluoro-1,3-benzothiazol-2-yl)amino]biphenyl-4-yl}carbonyl)-L-valine |
| 2 | N-({4'-[(6-fluoro-1,3-benzothiazol-2-yl)amino]biphenyl-4-yl}carbonyl)-L-alanine |
| 3 | N-({3'-fluoro-4'-[(6-fluoro-1,3-benzothiazol-2-yl)amino]biphenyl-4-yl}carbonyl)-L-alanine |
| 4 | N-({4'-[(6-fluoro-1,3-benzothiazol-2-yl)amino]biphenyl-4-yl}carbonyl)-L-valine |
| 5 | N-({3-chloro-4'-[(6-fluoro-1,3-benzothiazol-2-yl)amino]biphenyl-4-yl}carbonyl)-L-valine |
| 6 | N-({3'-fluoro-4'-[(6-fluoro-1,3-benzothiazol-2-yl)amino]-3-methylbiphenyl-4-yl}carbonyl)-L-valine |
| 7 | N-({3'-fluoro-4'-[(6-fluoro-1,3-benzothiazol-2-yl)amino]-3-methoxybiphenyl-4-yl}carbonyl)-L-valine |
| 8 | N-({4'-[(6-fluoro-1,3-benzothiazol-2-yl)amino]biphenyl-4-yl}carbonyl)-L-leucine |
| 9 | N-({3'-fluoro-4'-[(6-fluoro-1,3-benzothiazol-2-yl)amino]biphenyl-4-yl}carbonyl)-L-leucine |
| 10 | N-({4'-[(6-fluoro-1,3-benzothiazol-2-yl)amino]-3-methoxybiphenyl-4-yl}carbonyl)-L-leucine |
| 11 | N-({3'-fluoro-4'-[(6-fluoro-1,3-benzothiazol-2-yl)amino]-3-methoxybiphenyl-4-yl}carbonyl)-L-leucine |
| 12 | N-({3-chloro-4'-[(6-fluoro-1,3-benzothiazol-2-yl)amino]biphenyl-4-yl}carbonyl)-L-leucine |
| 13 | N-({4'-[(6-fluoro-1,3-benzothiazol-2-yl)amino]-3-methylbiphenyl-4-yl}carbonyl)-L-leucine |
| 14 | N-({3'-fluoro-4'-[(6-fluoro-1,3-benzothiazol-2-yl)amino]-3-methylbiphenyl-4-yl}carbonyl)-L-leucine |
| 15 | N-({4'-[(6-fluoro-1,3-benzothiazol-2-yl)amino]biphenyl-4-yl}carbonyl)-D-leucine |
| 16 | N-({3'-fluoro-4'-[(6-fluoro-1,3-benzothiazol-2-yl)amino]biphenyl-4-yl}carbonyl)-D-leucine |
| 17 | N-({4'-[(6-fluoro-1,3-benzothiazol-2-yl)amino]biphenyl-4-yl}carbonyl)-L-isoleucine |
| 18 | N-({3'-fluoro-4'-[(6-fluoro-1,3-benzothiazol-2-yl)amino]biphenyl-4-yl}carbonyl)-L-isoleucine |
| 19 | N-({3'-fluoro-4'-[(6-fluoro-1,3-benzothiazol-2-yl)amino]-3-methoxybiphenyl-4-yl}carbonyl)-L-isoleucine |
| 20 | N-({4'-[(6-fluoro-1,3-benzothiazol-2-yl)amino]biphenyl-4-yl}carbonyl)-L-phenylalanine |
| 21 | N-({3'-fluoro-4'-[(6-fluoro-1,3-benzothiazol-2-yl)amino]biphenyl-4-yl}carbonyl)-L-phenylalanine |
| 22 | N-({4'-[(6-fluoro-1,3-benzothiazol-2-yl)amino]-3-methoxybiphenyl-4-yl}carbonyl)-L-phenylalanine |
| 23 | N-({4'-[(6-fluoro-1,3-benzothiazol-2-yl)amino]-3-methylbiphenyl-4-yl}carbonyl)-L-phenylalanine |
| 24 | N-({3'-fluoro-4'-[(6-fluoro-1,3-benzothiazol-2-yl)amino]-3-methylbiphenyl-4-yl}carbonyl)-L-phenylalanine |
| 25 | N-({3-chloro-4'-[(6-fluoro-1,3-benzothiazol-2-yl)amino]biphenyl-4-yl}carbonyl)-L-phenylalanine |
| 26 | 1-({4'-[(6-fluoro-1,3-benzothiazol-2-yl)amino]biphenyl-4-yl}carbonyl)-L-proline |
| 27 | 1-({3'-fluoro-4'-[(6-fluoro-1,3-benzothiazol-2-yl)amino]biphenyl-4-yl}carbonyl)-L-proline |
| 28 | 1-({4'-[(6-fluoro-1,3-benzothiazol-2-yl)amino]-3-methoxybiphenyl-4-yl}carbonyl)-L-proline |
| 29 | 1-({3-chloro-4'-[(6-fluoro-1,3-benzothiazol-2-yl)amino]biphenyl-4-yl}carbonyl)-L-proline |
| 30 | 1-({4'-[(6-fluoro-1,3-benzothiazol-2-yl)amino]-3-methylbiphenyl-4-yl}carbonyl)-L-proline |
| 31 | 1-({3'-fluoro-4'-[(6-fluoro-1,3-benzothiazol-2-yl)amino]-3-methylbiphenyl-4-yl}carbonyl)-L-proline |

By using the methods described above and by substituting the appropriate starting materials, compounds of Formula (I), listed in Table 2a below, were similarly prepared.

TABLE 2a

Preparative Examples of Compounds of Formula (I)

| Example No. | $R^1$ | $R^2$ | $R^3$ | $R^4$ | LC-MS Ret. Time (min) | LC-MS $[M + H]^+$ | Method |
|---|---|---|---|---|---|---|---|
| 32 | 6-F | H | H | C(CH$_3$)$_2$(NH-)(CO$_2$H) | 3.57 | 450.2 | A |
| 33 | 6-F | F | H | C(CH$_3$)$_2$(NH-)(CO$_2$H) | 3.64 | 468.2 | A |
| 34 | 6-F | H | OCH$_3$ | C(CH$_3$)$_2$(NH-)(CO$_2$H) | 3.35 | 480.1 | B |
| 35 | 6-F | H | Cl | C(CH$_3$)$_2$(NH-)(CO$_2$H) | 3.30 | 484.1 | B |
| 36 | 6-F | H | CH$_3$ | C(CH$_3$)$_2$(NH-)(CO$_2$H) | 3.24 | 464.2 | B |
| 37 | 6-F | F | CH$_3$ | C(CH$_3$)$_2$(NH-)(CO$_2$H) | 3.28 | 482.3 | A |
| 38 | 6-F | H | H | 1-(NH-)cyclopropyl-CO$_2$H | 3.48 | 448.2 | A |
| 39 | 6-F | F | H | 1-(NH-)cyclopropyl-CO$_2$H | 3.23 | 466.3 | A |
| 40 | 6-F | F | OCH$_3$ | 1-(NH-)cyclopropyl-CO$_2$H | 3.34 | 496.3 | A |
| 41 | 6-F | H | H | 1-(NH-)cyclopentyl-CO$_2$H | 3.74 | 476.3 | A |

TABLE 2a-continued

Preparative Examples of Compounds of Formula (I)

| Example No. | R¹ | R² | R³ | R⁴ | LC-MS Ret. Time (min) | LC-MS [M + H]⁺ | Method |
|---|---|---|---|---|---|---|---|
| 42 | 6-F | F | H | cyclopentyl-NH-C(CO₂H) | 3.49 | 494.3 | A |
| 43 | 6-F | H | H | cyclohexyl-NH-C(CO₂H) | 3.87 | 490.3 | A |
| 44 | 6-F | H | H | CH₃-CH(NH-)-CO₂H | 3.25 | 450.1 | A |
| 45 | 6-F | F | H | CH₃-CH(NH-)-CO₂H | 3.37 | 468.3 | A |
| 46 | 6-F | F | OCH₃ | CH₃-CH(NH-)-CO₂H | 3.50 | 498.4 | A |
| 47 | 6-F | H | H | CH₃CH₂-CH(NH-)-CO₂H | 3.76 | 464.3 | A |
| 48 | 6-F | F | H | CH₃CH₂-CH(NH-)-CO₂H | 3.55 | 482.4 | A |
| 49 | 6-F | F | OCH₃ | CH₃CH₂-CH(NH-)-CO₂H | 3.63 | 512.3 | A |

TABLE 2a-continued
Preparative Examples of Compounds of Formula (I)
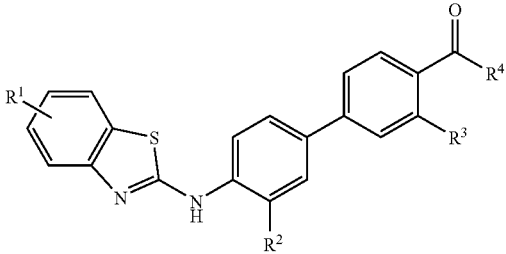
| Example No. | R¹ | R² | R³ | R⁴ | LC-MS Ret. Time (min) | LC-MS [M + H]⁺ | Method |
|---|---|---|---|---|---|---|---|
| 50 | 6-F | H | H | 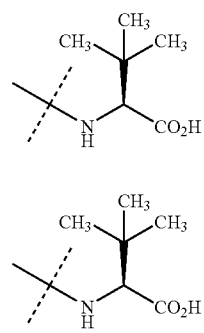 | 3.52 | 478.2 | A |
| 51 | 6-F | F | H | 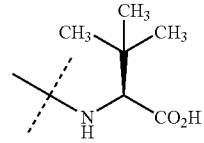 | 3.63 | 496.3 | A |
| 52 | 6-F | F | OCH₃ | 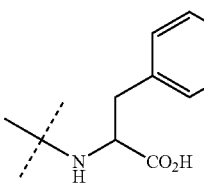 | 3.73 | 526.4 | A |
| 53 | 6-F | H | H | 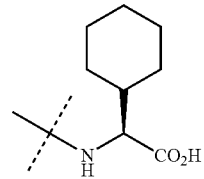 | 3.68 | 546.1 | A |
| 54 | 6-F | H | H | 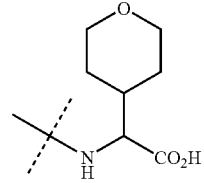 | 3.68 | 504.2 | A |
| 55 | 6-F | H | H |  | 3.15 | 506.2 | A |

TABLE 2a-continued

Preparative Examples of Compounds of Formula (I)

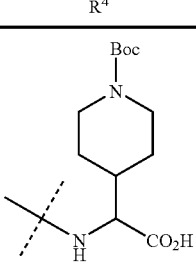

| Example No. | R¹ | R² | R³ | R⁴ | LC-MS Ret. Time (min) | LC-MS [M + H]⁺ | Method |
|---|---|---|---|---|---|---|---|
| 56 | 6-F | H | H | 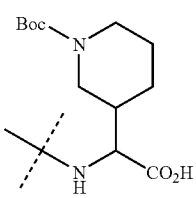 | 3.60 | 605.0 | A |
| 57 | 6-F | H | H | 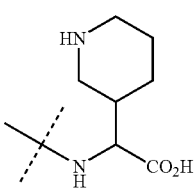 | 3.65 | 605.1 | A |
| 58 | 6-F | H | H | 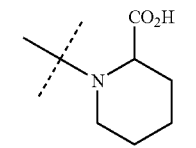 | 2.98 | 505.2 | A |
| 59 | 6-F | F | H | (structure, see image) | 3.80 | 494.2 | A |

TABLE 2b

IUPAC Names for Compounds in Table 2a

| Example No. | IUPAC Name |
|---|---|
| 32 | N-({4'-[(6-fluoro-1,3-benzothiazol-2-yl)amino]biphenyl-4-yl}carbonyl)-2-methylalanine |
| 33 | N-({3'-fluoro-4'-[(6-fluoro-1,3-benzothiazol-2-yl)amino]biphenyl-4-yl}carbonyl)-2-methylalanine |
| 34 | N-({4'-[(6-fluoro-1,3-benzothiazol-2-yl)amino]-3-methoxybiphenyl-4-yl}carbonyl)-2-methylalanine |
| 35 | N-({3-chloro-4'-[(6-fluoro-1,3-benzothiazol-2-yl)amino]biphenyl-4-yl}carbonyl)-2-methylalanine |
| 36 | N-({4'-[(6-fluoro-1,3-benzothiazol-2-yl)amino]-3-methylbiphenyl-4-yl}carbonyl)-2-methylalanine |
| 37 | N-({3'-fluoro-4'-[(6-fluoro-1,3-benzothiazol-2-yl)amino]3-methylbiphenyl-4-yl}carbonyl)-2-methylalanine |

TABLE 2b-continued

IUPAC Names for Compounds in Table 2a

| Example No. | IUPAC Name |
|---|---|
| 38 | 1-[({4'-[(6-fluoro-1,3-benzothiazol-2-yl)amino]biphenyl-4-yl}carbonyl)amino]cyclopropanecarboxylic acid |
| 39 | 1-[({3'-fluoro-4'-[(6-fluoro-1,3-benzothiazol-2-yl)amino]biphenyl-4-yl}carbonyl)amino]cyclopropanecarboxylic acid |
| 40 | 1-[({3'-fluoro-4'-[(6-fluoro-1,3-benzothiazol-2-yl)amino]-3-methoxybiphenyl-4-yl}carbonyl)amino]cyclopropanecarboxylic acid |
| 41 | 1-[({4'-[(6-fluoro-1,3-benzothiazol-2-yl)amino]biphenyl-4-yl}carbonyl)amino]cyclopentanecarboxylic acid |
| 42 | 1-[({3'-fluoro-4'-[(6-fluoro-1,3-benzothiazol-2-yl)amino]biphenyl-4-yl}carbonyl)amino]cyclopentanecarboxylic acid |
| 43 | 1-[({4'-[(6-fluoro-1,3-benzothiazol-2-yl)amino]biphenyl-4-yl}carbonyl)amino]cyclohexanecarboxylic acid |
| 44 | (2S)-2-[({4'-[(6-fluoro-1,3-benzothiazol-2-yl)amino]biphenyl-4-yl}carbonyl)amino]butanoic acid |
| 45 | (2S)-2-[({3'-fluoro-4'-[(6-fluoro-1,3-benzothiazol-2-yl)amino]biphenyl-4-yl}carbonyl)amino]butanoic acid |
| 46 | (2S)-2-[({3'-fluoro-4'-[(6-fluoro-1,3-benzothiazol-2-yl)amino]-3-methoxybiphenyl-4-yl}carbonyl)amino]butanoic acid |
| 47 | N-({4'-[(6-fluoro-1,3-benzothiazol-2-yl)amino]biphenyl-4-yl}carbonyl)-L-norvaline |
| 48 | N-({3'-fluoro-4'-[(6-fluoro-1,3-benzothiazol-2-yl)amino]biphenyl-4-yl}carbonyl)-L-norvaline |
| 49 | N-({3'-fluoro-4'-[(6-fluoro-1,3-benzothiazol-2-yl)amino]-3-methoxybiphenyl-4-yl}carbonyl)-L-norvaline |
| 50 | N-({4'-[(6-fluoro-1,3-benzothiazol-2-yl)amino]biphenyl-4-yl}carbonyl)-3-methyl-L-valine |
| 51 | N-({3'-fluoro-4'-[(6-fluoro-1,3-benzothiazol-2-yl)amino]biphenyl-4-yl}carbonyl)-3-methyl-L-valine |
| 52 | N-({3'-fluoro-4'-[(6-fluoro-1,3-benzothiazol-2-yl)amino]-3-methoxybiphenyl-4-yl}carbonyl)-3-methyl-L-valine |
| 53 | 4-chloro-N-({4'-[(6-fluoro-1,3-benzothiazol-2-yl)amino]biphenyl-4-yl}carbonyl)phenylalanine |
| 54 | (2S)-cyclohexyl[({4'-[(6-fluoro-1,3-benzothiazol-2-yl)amino]biphenyl-4-yl}carbonyl)amino]acetic acid |
| 55 | [({4'-[(6-fluoro-1,3-benzothiazol-2-yl)amino]biphenyl-4-yl}carbonyl)amino](tetrahydro-2H-pyran-4-yl)acetic acid |
| 56 | [1-(tert-butoxycarbonyl)piperidin-4-yl][({4'-[(6-fluoro-1,3-benzothiazol-2-yl)amino]biphenyl-4-yl}carbonyl)amino]acetic acid |
| 57 | [1-(tert-butoxycarbonyl)piperidin-3-yl][({4'-[(6-fluoro-1,3-benzothiazol-2-yl)amino]biphenyl-4-yl}carbonyl)amino]acetic acid |
| 58 | [({4'-[(6-fluoro-1,3-benzothiazol-2-yl)amino]biphenyl-4-yl}carbonyl)amino](piperidin-3-yl)acetic acid |
| 59 | 1-({3'-fluoro-4'-[(6-fluoro-1,3-benzothiazol-2-yl)amino]biphenyl-4-yl}carbonyl)piperidine-2-carboxylic acid |

Preparation of Intermediate Compounds of Formula (XIII) by Method C

Intermediate XIII-1: Methyl N-[(4'-aminobiphenyl-4-yl)carbonyl]-2-methylalaninate

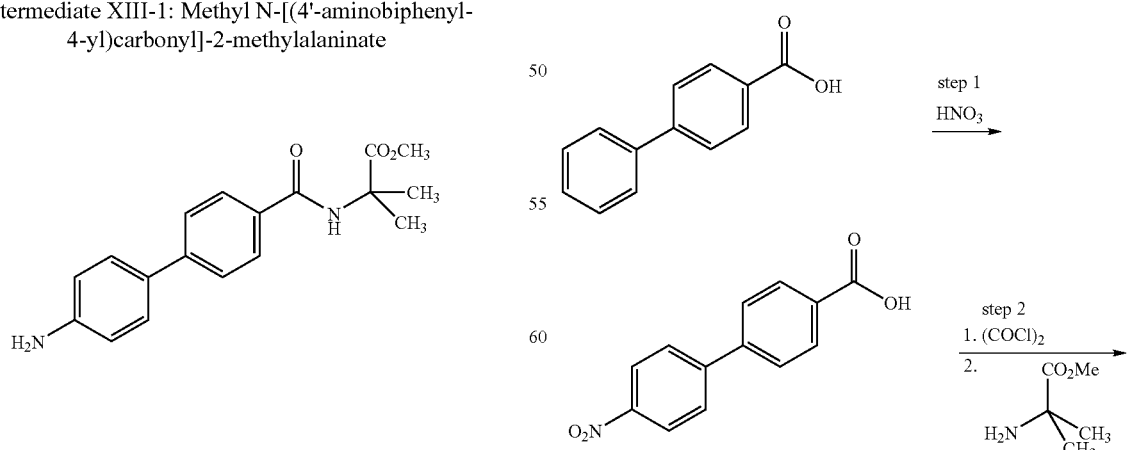

Reaction Scheme 10

The preparation of methyl N-[(4'-aminobiphenyl-4-yl)carbonyl]-2-methylalaninate is described below in Reaction Scheme 10.

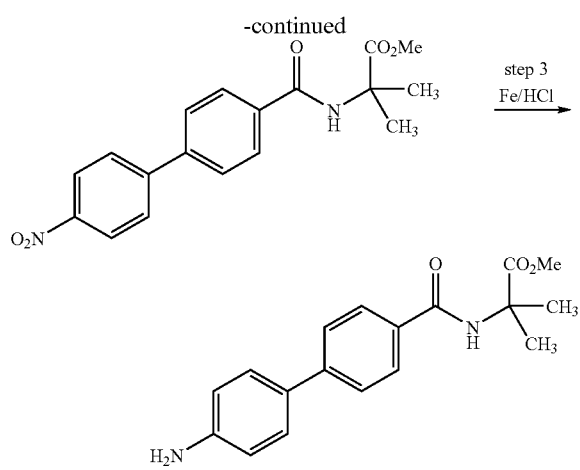

Step 1. Preparation of 4'-nitro-1,1'-biphenyl-4-carboxylic Acid

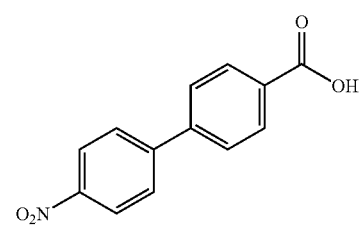

As shown in Reaction Scheme 10, to ice-cold nitric acid was added 4-biphenylcarboxylic acid (9.4 g, 20.0 mmol), and the resulting mixture was stirred with cooling in an ice-water bath for 1 h. The mixture was poured into ice-water and filtered. The collected solid was suspended in ethanol and heated at reflux for 2 h. The mixture was filtered hot, washed with ethanol and dried under high vacuum to give 4'-nitro-1,1'-biphenyl-4-carboxylic acid (2.3 g, 47%). $^1$H NMR (400 MHz, DMSO-$d_6$) δ 7.89 (d, 2H), 8.01 (d, 2H), 8.05 (d, 2H), 8.31 (d, 2H), 13.12 (d, 2H).

Step 2. Preparation of methyl 2-methyl-N-[(4'-nitro-biphenyl-4-yl)carbonyl]alaninate

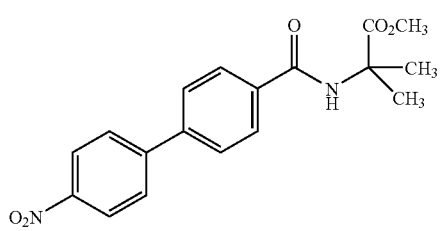

As shown in Reaction Scheme 10, 4'-nitro-1,1'-biphenyl-4-carboxylic acid (4.66 g, 19.2 mmol) was dissolved in methylene chloride (110 mL), and then oxalyl chloride (2.51 mL, 28.7 mmol) was added, followed by 3 drops of N,N-dimethylformamide. The resulting mixture was stirred at rt for 45 min, concentrated under reduced pressure, and further dried under vacuum for 30 min. The residue was dissolved in methylene chloride (75 mL) and added dropwise to an ice-cold mixture of methyl 2-methylalaninate hydrochloride (3.83 g, 24.9 mmol), methylene chloride (75 mL), and triethylamine (6.68 mL, 47.9 mmol). The resulting solution was stirred at rt for 1 h and then at 55° C. for 2 h. The mixture was allowed to cool to rt and was then washed with 1N aqueous HCl solution (5 mL) and water (2×20 mL). The organic layer was separated, dried (MgSO$_4$), and concentrated under reduced pressure. The residue was purified by flash chromatography (Biotage® system, 4:1 hexanes/EtOAc) to afford methyl 2-methyl-N-[(4'-nitrobiphenyl-4-yl)carbonyl]alaninate (6.21 g, 95%). $^1$H NMR (400 MHz, CDCl$_3$) δ 1.73 (s, 6H), 3.82 (s, 3H), 6.89 (broad s, 1H), 7.69 (d, 2H), 7.77 (d, 2H), 7.92 (d, 2H), 8.31 (d, 2H); LC-MS m/z 342.9 (MH$^+$), retention time 2.98 minutes.

Step 3. Preparation of methyl N-[(4'-aminobiphenyl-4-yl)carbonyl]-2-methylalaninate

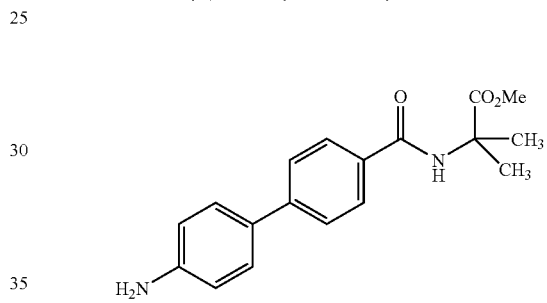

As shown in Reaction Scheme 10, to a solution of methyl 2-methyl-N-[(4'-nitrobiphenyl-4-yl)carbonyl]alaninate (1.59 g, 4.6 mmol) in 85% ethanol (50 mL) was added iron powder (2.59 g, 46.4 mmol) and 2 M aqueous HCl solution (2.32 mL, 4.6 mmol). The resulting mixture was heated at reflux for 2 h. The mixture was then filtered through a pad of Celite® and concentrated under reduced pressure to afford N-[(4'-aminobiphenyl-4-yl)carbonyl]-2-methylalaninate as a yellow solid (2.48 g, 99%). $^1$H NMR (400 MHz, DMSO-$d_6$) δ 1.44 (s, 6H), 3.57 (s, 3H), 5.33 (broad s, 2H), 6.61 (d, 2H), 7.41 (d, 2H), 7.58 (d, 2H), 7.83 (d, 2H), 8.54 (broad s, 1H); LC-MS m/z 313.2 (MH$^+$), retention time 1.54 minutes.

Intermediate XIII-2: Methyl N-[(4'-aminobiphenyl-4-yl)carbonyl]-N-methyl-L-valinate

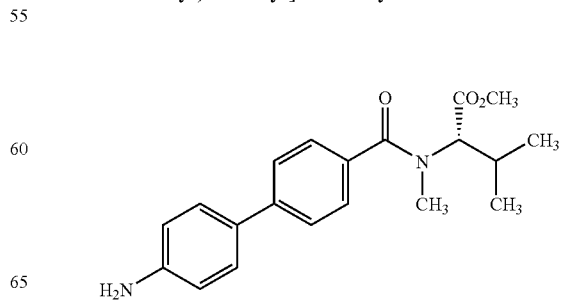

Step 1. Preparation of methyl N-methyl-N-[(4'-nitro-1,1'-biphenyl-4-yl)carbonyl]-L-valinate

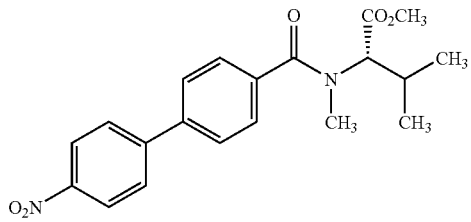

4'-Nitro-1,1'-biphenyl-4-carboxylic acid (0.50 g, 2.0 mmol) was dissolved in methylene chloride (25 mL), and then oxalyl chloride (0.27 mL, 3.1 mmol) was added, followed by one drop of N,N-dimethylformamide. The resulting mixture was heated at 50° C. for 1 h, concentrated under reduced pressure, and further dried under vacuum for 30 min. The residue was dissolved in methylene chloride (20 mL) and added dropwise to an ice-cold mixture of methyl N-methyl-L-valinate hydrochloride (0.48 g, 2.6 mmol), methylene chloride (50 mL), and triethylamine (1.44 mL, 10.2 mmol). The resulting solution was stirred on ice for 1 h and then at rt overnight. The mixture was diluted with methylene chloride and washed with 1N aqueous HCl solution and brine. The organic layer was separated and concentrated under reduced pressure. The residue was purified by flash chromatography (Biotage® system, 3:1 hexanes/EtOAc) to afford methyl N-methyl-N-[(4'-nitro-1,1'-biphenyl-4-yl)carbonyl]-L-valinate (0.70 g, 92%). $^1$H NMR (400 MHz, CDCl$_3$) δ 0.85 (dd, 3H), 1.06 (dd, 3H), 2.31 (m, 1H), 3.02 (d, 3H), 3.77 (d, 3H), 3.94 (d, 0.5H), 4.98 (d, 0.5H), 7.52 (m, 2H), 7.64 (m, 2H), 7.72 (t, 2H), 8.27 (d, 2H); LC-MS m/z 371.2 (MH$^+$), retention time 3.27 minutes.

Step 2. Preparation of methyl N-[(4'-amino-1,1'-biphenyl-4-yl)carbonyl]-N-methyl-L-valinate

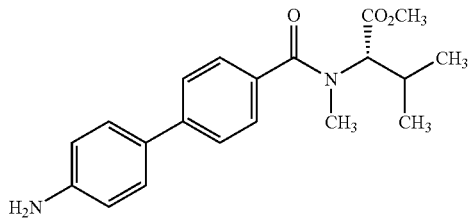

To a solution of methyl N-methyl-N-[(4'-nitro-1,1'-biphenyl-4-yl)carbonyl]-L-valinate (0.70 g, 1.9 mmol) in 85% ethanol (20 mL) was added iron powder (1.05 g, 18.9 mmol) and 2N aqueous HCl solution (0.41 mL). The resulting mixture was heated at reflux for 2 h. The mixture was then filtered through a pad of Celite® and concentrated under reduced pressure. The residue was dissolved in methylene chloride, washed with water and brine, dried (Na$_2$SO$_4$) and concentrated under reduced pressure to afford methyl N-[(4'-amino-1,1'-biphenyl-4-yl)carbonyl]-N-methyl-L-valinate (0.49 g, 76%). $^1$H NMR (400 MHz, CD$_3$OD) δ 0.85 (dd, 3H), 1.06 (dd, 3H), 2.35 (m, 1H), 3.02 (d, 3H), 3.75 (d, 3H), 4.05 (d, 0.5H), 4.78 (d, 0.5H), 6.78 (d, 2H), 7.42 (m, 4H), 7.63 (d, 2H); LC-MS m/z 341.2 (MH$^+$), retention time 2.37 minutes.

Intermediate XII-3: Methyl N-[(4'-amino-1,1'-biphenyl-4-yl)carbonyl]-L-valinate

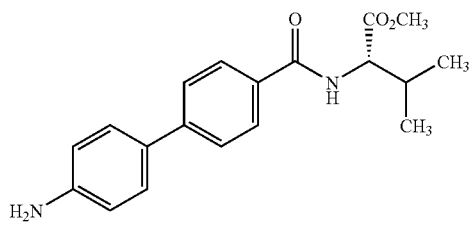

Step 1. Preparation of methyl-N-[(4'-nitro-1,1'-biphenyl-4-yl)carbonyl]-L-valinate

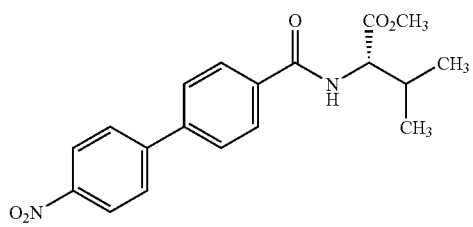

4'-Nitro-1,1'-biphenyl-4-carboxylic acid (0.60 g, 2.4 mmol) was dissolved in methylene chloride (25 mL), and then oxalyl chloride (0.32 mL, 3.7 mmol) was added, followed by one drop of N,N-dimethylformamide. The resulting mixture was heated at 50° C. for 1 h, concentrated under reduced pressure, and further dried under vacuum for 30 min. The residue was dissolved in methylene chloride (20 mL) and added dropwise to an ice-cold mixture of methyl L-valinate hydrochloride (0.54 mg, 3.2 mmol), methylene chloride (25 mL), and triethylamine (1.74 mL, 12.3 mmol). The resulting solution was stirred on ice for 1 h and then at rt overnight. The mixture was diluted with methylene chloride and washed with 1N aqueous HCl solution and brine. The organic layer was separated and concentrated under reduced pressure. The residue was purified by flash chromatography (Biotage® system, 2:1 hexanes/EtOAc) to afford methyl-N-[(4'-nitro-1,1'-biphenyl-4-yl)carbonyl]-L-valinate (0.70 g, 80%). $^1$H NMR (400 MHz, CD$_3$OD) δ 1.06 (dd, 6H), 2.38 (m, 1H), 3.77 (s, 3H), 4.52 (d, 1H), 7.82 (d, 2H), 7.91 (d, 2H), 7.97 (d, 2H), 8.33 (d, 2H); LC-MS m/z 357.1 (MH$^+$), retention time 3.07 minutes.

Step 2. Preparation of methyl N-[(4'-amino-1,1'-biphenyl-4-yl)carbonyl]-L-valinate

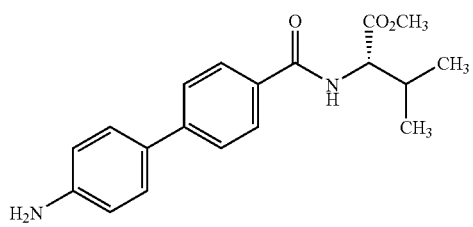

To a solution of methyl-N-[(4'-nitro-1,1'-biphenyl-4-yl)carbonyl]-L-valinate (0.70 g, 1.9 mmol) in 85% ethanol (20 mL) was added iron powder (1.09 g, 19.6 mmol) and 2N aqueous HCl solution (1.0 mL). The resulting mixture was heated at reflux for 2 h. The mixture was then filtered through a pad of Celite® and concentrated under reduced pressure. The residue was dissolved in dichloromethane and washed with water and brine, dried (Na$_2$SO$_4$), and concentrated under reduced pressure to afford methyl N-[(4'-amino-1,1'-biphenyl-4-yl)carbonyl]-L-valinate (0.58 g, 90%). $^1$H NMR (400 MHz, CD$_3$OD) δ 1.03 (dd, 6H), 2.26 (m, 1H), 3.74 (s, 3H), 4.48 (d, 1H), 6.77 (d, 2H), 7.43 (d, 2H), 7.62 (d, 2H), 7.83 (d, 2H); LC-MS m/z 327.1 (MH$^+$), retention time 2.27 minutes.

Intermediate XII-4: Methyl N-[(4'-aminobiphenyl-4-yl)carbonyl]-N,2-dimethylalaninate

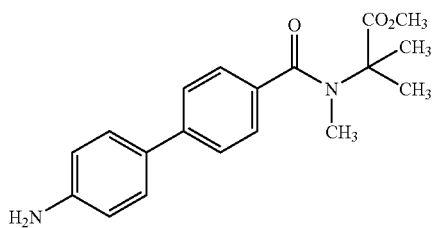

The preparation of methyl N-[(4'-aminobiphenyl-4-yl)carbonyl]-N,2-dimethylalaninate is described below in Reaction Scheme 11.

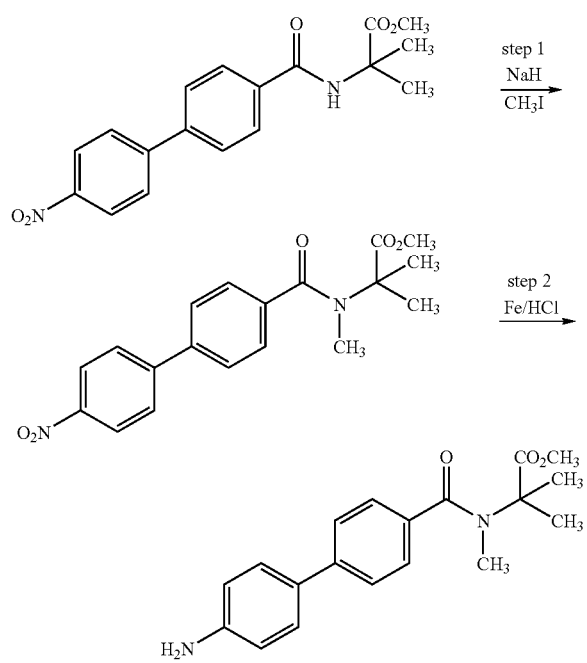

Step 1. Preparation of methyl N,2-dimethyl-N-[(4'-nitrobiphenyl-4-yl)carbonyl]alaninate As shown in Reaction Scheme 11, a mixture of methyl 2-methyl-N-[(4'-nitrobiphenyl-4-yl)carbonyl]alaninate (1.32 g, 3.9 mmol), sodium hydride (117 mg, 4.6 mmol), and N,N-dimethylformamide (15 mL) was stirred for 2 h at rt. Iodomethane (0.48 mL, 7.7 mmol) was added, and the reaction mixture was stirred overnight at rt. Water (30 mL) was added, and the mixture was extracted with ethyl acetate (2×10 mL). The combined extracts were evaporated to dryness, and crude product was purified by flash chromatography (Biotage®, 4:1 hexanes/EtOAc) to yield methyl N,2-dimethyl-N-[(4'-nitrobiphenyl-4-yl)carbonyl]alaninate as an off-white solid (1.29 g, 94%). $^1$H NMR (400 MHz, DMSO-d$_6$) δ 1.47 (s, 6H), 2.93 (s, 3H), 3.58 (s, 3H), 7.52 (d, 2H), 7.84 (d, 2H), 7.98 (d, 2H), 8.30 (d, 2H); LC-MS m/z 356.9 (MH$^+$), retention time 2.98 minutes.

Step 2. Preparation of methyl N-[(4'-aminobiphenyl-4-yl)carbonyl]-N,2-dimethylalaninate

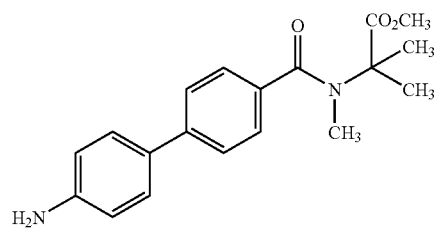

As shown in Reaction Scheme 11, to a solution of methyl N,2-dimethyl-N-[(4'-nitrobiphenyl-4-yl)carbonyl]alaninate (1.92 g, 5.4 mmol) in 85% ethanol (50 mL) was added iron powder (3.01 g, 53.88 mmol) and 2 M aqueous HCl solution (2.69 mL, 5.4 mmol). The resulting mixture was heated at reflux for 2.5 h. The mixture was filtered through a pad of Celite® and concentrated under reduced pressure to afford methyl N-[(4'-aminobiphenyl-4-yl)carbonyl]-N,2-dimethylalaninate as a yellow solid (1.44 g, 82%). $^1$H NMR (400 MHz, DMSO-d$_6$) δ 1.42 (s, 6H), 2.94 (s, 3H), 3.57 (s, 3H), 5.30 (broad s, 2H), 6.61 (d, 2H), 7.31-7.40 (m, 4H), 7.58 (d, 2H); LC-MS m/z 327.2 (MH$^+$), retention time 1.84 minutes.

Intermediate XIII-5: Methyl N-[(4'-amino-3-methyl-biphenyl-4-yl)carbonyl]-L-valinate

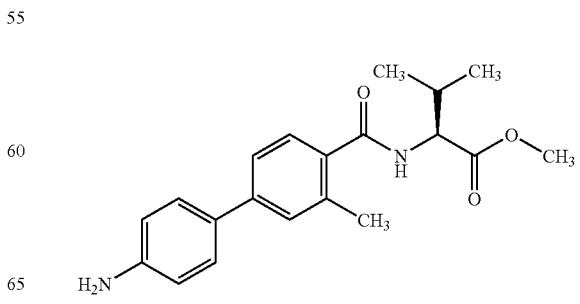

Step 1. Preparation of 3-methyl-4'-nitrobiphenyl-4-carboxylic acid

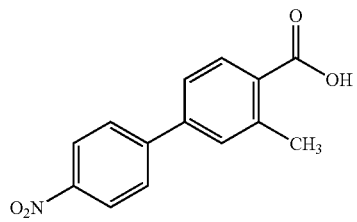

Methyl 3-methyl-4'-nitrobiphenyl-4-carboxylate (0.70 g, 2.1 mmol) was suspended in THF (5 mL), MeOH (5 mL) and water (2.5 mL), and NaOH (0.41 g, 10.3 mmol) was added. The reaction mixture was heated at 50° C. for 3 h. Upon cooling to rt, the reaction mixture was concentrated in vacuo and purified by reversed-phase HPLC to give 0.498 g (94%) of the title compound. $^1$H NMR (400 MHz, DMSO-$d_6$) δ 2.62 (s, 3H), 7.62-7.68 (m, 2H), 7.91-8.05 (m 3H), 7.18 (t, 1H), 8.31 (d, 1H).

Step 2. Preparation of methyl N-[(3-methyl-4'-nitrobiphenyl-4-yl)carbonyl]-L-valinate

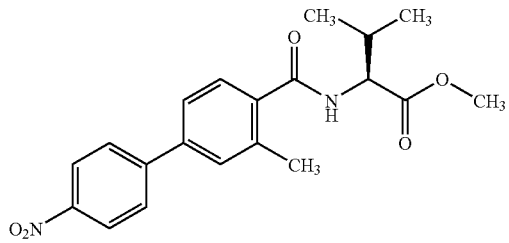

3-Methyl-4'-nitrobiphenyl-4-carboxylic acid (0.50 g, 1.0 mmol) was dissolved in methylene chloride (10 mL), and then oxalyl chloride (0.25 mL, 0.29 mmol) was added, followed by one drop of DMF. The resulting mixture was stirred at 50° C. for 45 min and then concentrated under reduced pressure. The residue was dissolved in methylene chloride (5 mL) and added dropwise to an ice-cold mixture of L-valine methyl ester hydrochloride (0.39 g, 2.3 mmol), methylene chloride (10 mL), and triethylamine (1.08 mL, 7.75 mmol). The resulting solution was stirred at rt for 18 h. The mixture was concentrated under reduced pressure, and the residue was purified by column chromatography (50% EtOAc in hexanes). This yielded 0.653 g (91%) of the title compound. LC/MS m/z 370.9 (MH$^+$), retention time 3.29 min. $^1$H NMR (400 MHz, CD$_2$Cl$_2$) δ 1.06 (dd, 6H), 2.32-2.39 (m, 1H), 2.55 (s, 3H), 3.78 (s, 3H), 4.71-4.78 (m, 1H), 6.33 (d, 1H), 7.42-7.52 (m, 3H), 7.82 (d, 2H), 8.26 (d, 2H).

Step 3. Preparation of methyl N-[(4'-amino-3-methylbiphenyl-4-yl)carbonyl]-L-valinate

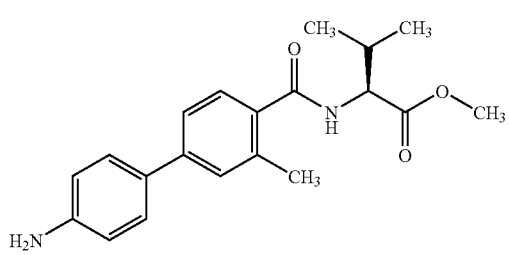

Iron powder (0.79 g, 14 mmol) was added to a solution of methyl N-[(3-methyl-4'-nitrobiphenyl-4-yl)carbonyl]-L-valinate (0.65 g, 1.4 mmol) in ethanol (20 mL). Concentrated HCl (0.71 mL, 1.4 mmol) was added, and the mixture was heated at reflux for 1 h. Upon cooling to rt, the mixture was filtered through a pad of Celite®, and the filtrate was concentrated in vacuo. The material was purified by column chromatography (33% EtOAc in hexanes), yielding 0.50 g (quantitative) of the title compound. LC/MS m/z 341.1 (MH$^+$), retention time 2.19 min. $^1$H NMR (400 MHz, CD$_2$Cl$_2$) δ 1.06 (dd, 6H), 2.32-2.39 (m, 1H), 2.50 (s, 3H), 3.78 (s, 3H), 4.71-4.78 (m, 1H), 6.33 (d, 1H), 6.78 (d, 2H), 7.38-7.44 (m, 5H).

Intermediate XIII-6: Methyl N-[(4'-amino-3-methoxybiphenyl-4-yl)carbonyl]-L-valinate

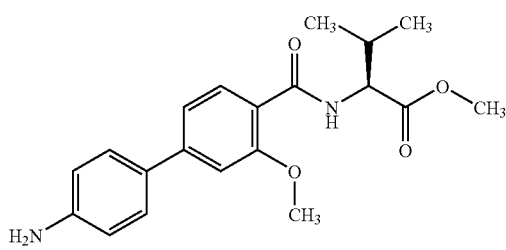

Step 1. Preparation of 3-methoxy-4'-nitrobiphenyl-4-carboxylic Acid

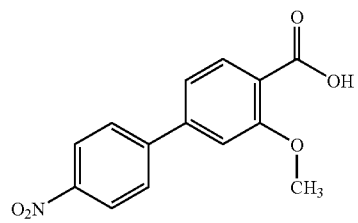

Methyl 3-methoxy-4'-nitrobiphenyl-4-carboxylate (0.35 g, 0.97 mmol) was suspended in THF (6 mL), MeOH (6 mL) and water (3 mL), and NaOH (0.19 g, 4.9 mmol) was added. The reaction mixture was heated at 50° C. for 3 h. Upon cooling to rt, the reaction mixture was concentrated under reduced pressure and acidified with 2N HCl. The resulting solid was collected by filtration and dried in a 40° C. vacuum oven, yielding 0.28 g (quantitative) of the title compound. $^1$H NMR (400 MHz, DMSO-$d_6$) δ 3.90 (s, 3H), 7.35-7.41 (m, 2H), 7.77 (d, 1H), 8.03 (d, 2H), 8.36 (d, 2H).

Step 2. Preparation of methyl N-[(3-methoxy-4'-nitrobiphenyl-4-yl)carbonyl]-L-valinate

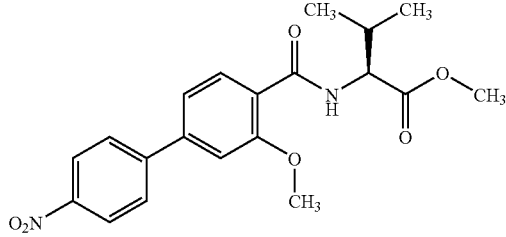

3-Methoxy-4'-nitrobiphenyl-4-carboxylic acid (0.28 g, 1.0 mmol) was dissolved in methylene chloride (10 mL), and then oxalyl chloride (0.13 mL, 1.51 mmol) was added, followed by one drop of DMF. The resulting mixture was stirred at 50° C. for 45 min and then concentrated under reduced pressure. The residue was dissolved in methylene chloride (5 mL) and added dropwise to an ice-cold mixture of L-valine methyl ester hydrochloride (0.21 g, 1.2 mmol), methylene chloride (10 mL), and triethylamine (0.57 mL, 4.1 mmol). The resulting solution was stirred at rt for 18 h. The mixture was concentrated under reduced pressure, and the residue was purified by column chromatography (33% EtOAc in hexanes). LC/MS m/z 387.0 (MH$^+$), retention time 3.40 min. $^1$H NMR (400 MHz, CD$_2$Cl$_2$) δ 1.05 (t, 6H), 2.32-2.39 (m, 1H), 3.78 (s, 3H), 4.10 (s, 3H), 4.71-4.78 (m, 1H), 7.22 (s, 1H), 7.38 (d, 1H), 7.80 (d, 2H), 8.22-8.37 (m, 4H).

Step 3. Preparation of methyl N-[(4'-amino-3-methoxybiphenyl-4-yl)carbonyl]-L-valinate

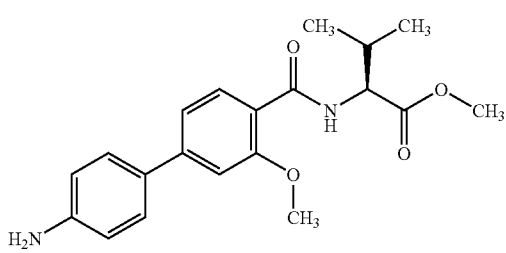

Iron powder (0.35 g, 6.2 mmol) was added to a solution of methyl N-[(3-methoxy-4'-nitrobiphenyl-4-yl)carbonyl]-L-valinate (0.30 g, 0.62 mmol) in ethanol (10 mL). Concentrated HCl (0.31 mL, 0.62 mmol) was added, and the mixture was heated at reflux for 1 h. Upon cooling to rt, the mixture was filtered through a pad of Celite®, and the filtrate was concentrated in vacuo. The material was purified by column chromatography (33% EtOAc in hexanes), yielding 0.296 g (quantitative) of the title compound. LC/MS m/z 357.2 (MI), retention time 2.34 min.

Intermediate XIII-7: Methyl N-[(4'-amino-3-chlorobiphenyl-4-yl)carbonyl]-L-valinate

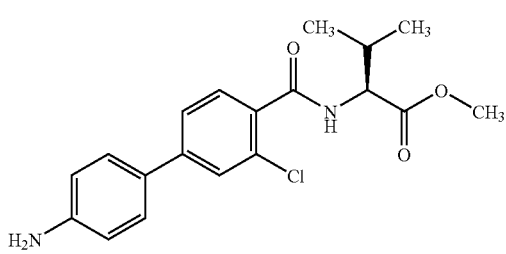

Step 1. Preparation of 3-chloro-4'-nitrobiphenyl-4-carboxylic Acid

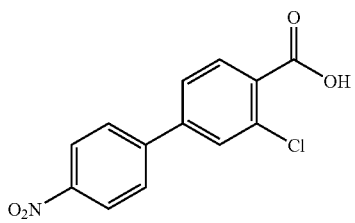

Methyl 3-chloro-4'-nitrobiphenyl-4-carboxylate (0.50 g, 1.4 mmol) was suspended in THF (6 mL), MeOH (6 mL) and water (3 mL), and NaOH (0.27 g, 6.9 mmol) was added. The reaction mixture was heated at 50° C. for 3 h. Upon cooling to rt, the reaction mixture was concentrated under reduced pressure and acidified with 2N HCl. The resulting solid was collected by filtration and dried in a 40° C. vacuum oven, yielding 0.315 g (83%) of the title compound. $^1$H NMR (400 MHz, DMSO-d$_6$) δ 7.81-8.10 (m, 5H), 8.21-8.38 (m, 2H).

Step 2. Preparation of methyl N-[(3-chloro-4'-nitrobiphenyl-4-yl)carbonyl]-L-valinate

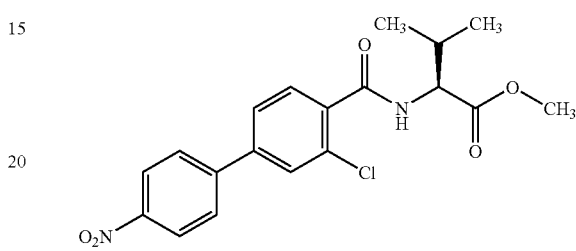

3-Chloro-4'-nitrobiphenyl-4-carboxylic acid (0.31 g, 1.12 mmol) was dissolved in methylene chloride (10 mL), and then oxalyl chloride (0.15 mL, 1.7 mmol) was added, followed by one drop of DMF. The resulting mixture was stirred at 50° C. for 45 min and then concentrated under reduced pressure. The residue was dissolved in methylene chloride (5 mL) and added dropwise to an ice-cold mixture of L-valine methyl ester hydrochloride (0.22 g, 1.3 mmol), methylene chloride (10 mL), and triethylamine (0.62 mL, 4.5 mmol). The resulting solution was stirred at rt for 18 h and then concentrated under reduced pressure. The residue was taken up in EtOAc, passed through a plug of silica gel, and concentrated under reduced pressure. This yielded 0.305 g (70%) of the title compound. LC/MS m/z 390.9 (MH$^+$), retention time 3.30 min. $^1$H NMR (400 MHz, CD$_2$Cl$_2$) δ 1.06 (dd, 6H), 2.32-2.39 (m, 1H), 3.80 (s, 3H), 4.71-4.78 (m, 1H), 6.33 (d, 1H), 6.76 (d, 2H), 7.58-7.80 (m, 5H), 8.35 (d, 2H).

Step 3. Preparation of methyl N-[(4'-amino-3-chlorobiphenyl-4-yl)carbonyl]-L-valinate

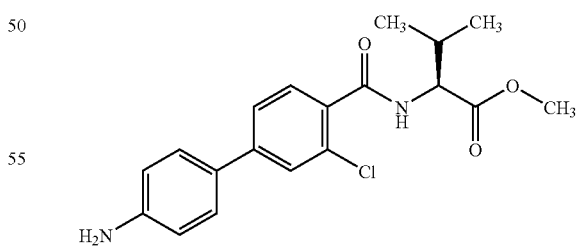

Iron powder (0.44 g, 7.8 mmol) was added to a solution of methyl N-[(3-chloro-4'-nitrobiphenyl-4-yl)carbonyl]-L-valinate (0.30 g, 0.78 mmol) in ethanol (10 mL). Concentrated HCl (0.39 mL, 0.78 mmol) was added, and the mixture was heated at reflux for 3 h. Upon cooling to rt, the mixture was filtered through a pad of Celite®, and the filtrate was concentrated in vacuo. The material was purified by column chromatography (33% EtOAc in hexanes), yielding 0.25 g (89%) of the title compound. LC/MS m/z/z 361.2 (MH⁺), retention time 2.36 min. ¹H NMR (400 MHz, CD₂Cl₂) δ 1.06 (dd, 6H), 2.32-2.39 (m, 1H), 3.80 (s, 3H), 4.71-4.78 (m, 1H), 6.82 (d, 3H), 7.40-7.74 (m, 5H).

Preparation of Compounds of Formula (I) by Method C

Example 60

N-({4'-[(6-fluoro-1,3-benzothiazol-2-yl)amino]-3-methoxybiphenyl-4-yl}carbonyl)-L-valine

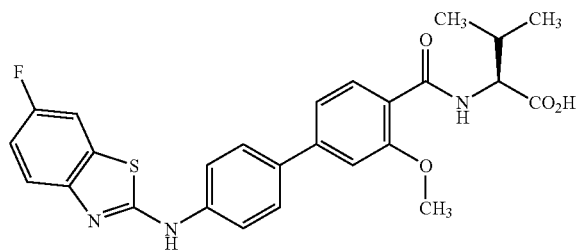

Step 1. Preparation of methyl N-({4'-[(6-fluoro-1,3-benzothiazol-2-yl)amino]-3-methoxy biphenyl-4-yl}carbonyl)-L-valinate and butyl N-({4'-[(6-fluoro-1,3-benzothiazol-2-yl)amino]-3-methoxybiphenyl-4-yl}carbonyl)-L-valinate

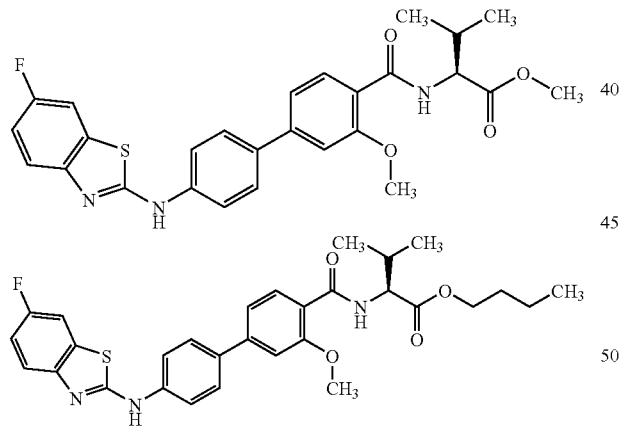

A mixture of methyl N-[(4'-amino-3-methoxybiphenyl-4-yl)carbonyl]-L-valinate (0.05 g, 0.14 mmol), 2-chloro-6-fluorobenzothiazole (0.03 g, 0.14 mmol), and 1-butanol (1.5 mL) was heated to 60-70° C., and then 4N HCl in 1,4-dioxane (0.02 mL, 0.07 mmol) was added with stirring. The reaction mixture was heated at 90° C. for 18 h. Upon cooling to rt, the reaction mixture was concentrated under reduced pressure and purified by HPLC (40-90% CH₃CN in H₂O/0.1% TFA gradient). This gave 7 mg (10%) of methyl N-({4'-[(6-fluoro-1,3-benzothiazol-2-yl)amino]-3-methoxybiphenyl-4-yl}carbonyl)-L-valinate and 39 mg (51%) of butyl N-({4'-[(6-fluoro-1,3-benzothiazol-2-yl)amino]-3-methoxybiphenyl-4-yl}carbonyl)-L-valinate.

Step 2. Preparation of N-({4'-[(6-fluoro-1,3-benzothiazol-2-yl)amino]-3-methoxybiphenyl-4-yl}carbonyl)-L-valine

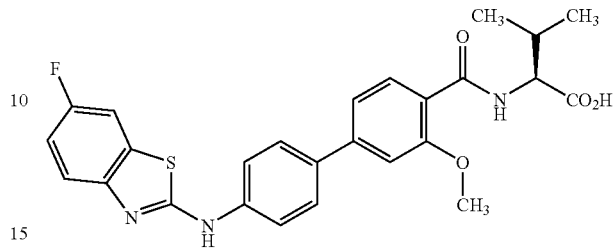

Butyl N-({4'-[(6-fluoro-1,3-benzothiazol-2-yl)amino]-3-methoxybiphenyl-4-yl}carbonyl)-L-valinate (0.02 g, 0.03 mmol) was suspended in THF (1 mL), MeOH (1 mL) and water (0.5 mL), and then LiOH (0.01 g, 0.35 mmol) was added. The reaction mixture was heated at 50° C. for 3 h. Upon cooling to rt, the reaction mixture was concentrated under reduced pressure and acidified with 2N HCl. The resulting solid was collected by filtration and purified by HPLC (15-80% CH₃CN in H₂O/0.1% TFA gradient), yielding 19 mg (91%) of the title compound. LC/MS m/z 494.1 (MH⁺), retention time 3.47 min. ¹H NMR (400 MHz, CD₃OD) δ 1.06 (d, 6H), 2.32-2.39 (m, 1H), 4.10 (s, 3H), 4.60 (d, 1H), 7.05 (t, 1H), 7.35-7.58 (m, 4H), 7.60 (d, 2H), 7.80 (d, 2H), 8.05 (d, 1H).

By using the methods described above and by substituting the appropriate starting materials, compounds of Formula (I), listed in Table 3a below, were similarly prepared.

TABLE 3a

Preparative Examples of Compounds of Formula (I) by Method C

| Example No. | R¹ | R³ | R⁴ | LC-MS Ret. Time (min) | LC-MS [M + H]⁺ |
|---|---|---|---|---|---|
| 60 | 6-F | OCH₃ | L-Val-OH | 3.50 | 494.1 |
| 61 | 6-F | CH₃ | L-Val-OH | 3.39 | 478.2 |
| 62 | 6-OCH₃ | CH₃ | L-Val-OH | 3.21 | 490.2 |
| 63 | H | CH₃ | L-Val-OH | 3.24 | 460.2 |
| 64 | 6-i-Pr | CH₃ | L-Val-OH | 3.65 | 502.2 |
| 65 | 6-Cl | CH₃ | L-Val-OH | 3.59 | 494.2 |
| 66 | 7-F | CH₃ | L-Val-OH | 3.47 | 478.2 |
| 67 | 7-Cl | CH₃ | L-Val-OH | 3.62 | 494.2 |
| 68 | H | OCH₃ | L-Val-OH | 3.37 | 476.1 |
| 69 | H | H | L-Val-OH | 3.39 | 446.2 |
| 70 | H | H | D-Val-OH | 3.21 | 446.2 |
| 71 | 6-Cl | OCH₃ | L-Val-OH | 3.71 | 510.2 |
| 72 | 7-F | OCH₃ | L-Val-OH | 3.56 | 494.2 |
| 73 | 7-Cl | OCH₃ | L-Val-OH | 3.71 | 510.1 |
| 74 | 6-i-Pr | OCH₃ | L-Val-OH | 3.77 | 518.2 |
| 75 | H | Cl | L-Val-OH | 3.36 | 480.2 |
| 76 | 6-i-Pr | Cl | L-Val-OH | 3.73 | 522.2 |
| 77 | 6-Cl | Cl | L-Val-OH | 3.67 | 550.9 |
| 78 | 7-F | Cl | L-Val-OH | 3.53 | 498.1 |

TABLE 3a-continued

Preparative Examples of Compounds of Formula (I) by Method C

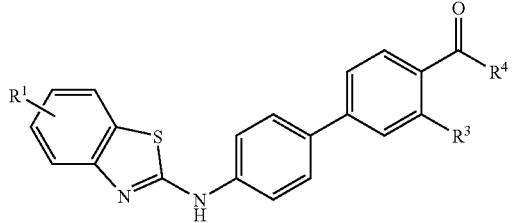
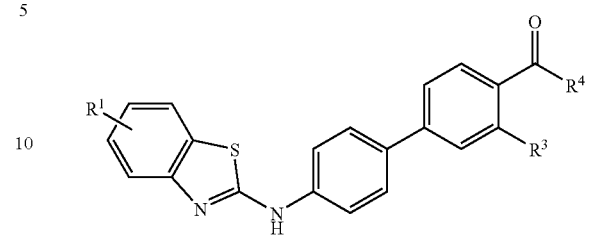

| Example No. | R¹ | R³ | R⁴ | LC-MS Ret. Time (min) | LC-MS [M + H]⁺ |
|---|---|---|---|---|---|
| 79 | 7-Cl | Cl | L-Val-OH | 3.68 | 514.1 |
| 80 | H | OCH₃ | L-Leu-OH | 3.87 | 490.3 |
| 81 | 6-OCH₃ | OCH₃ | L-Leu-OH | 3.85 | 520.3 |
| 82 | 6-Cl | OCH₃ | L-Leu-OH | 4.19 | 524.3 |
| 83 | 4-Cl, 6-F | OCH₃ | L-Leu-OH | 4.21 | 542.1 |
| 84 | 6-NO₂ | OCH₃ | L-Leu-OH | 3.98 | 535.0 |
| 85 | 6-(CH₃)SO₂ | OCH₃ | L-Leu-OH | 3.54 | 568.2 |
| 86 | 6-i-Pr | OCH₃ | L-Leu-OH | 4.24 | 532.3 |

TABLE 3b

IUPAC Names of Compounds in Table 3a

| Example No. | IUPAC Name |
|---|---|
| 60 | N-({4'-[(6-fluoro-1,3-benzothiazol-2-yl)amino]-3-methoxybiphenyl-4-yl}carbonyl)-L-valine |
| 61 | N-({4'-[(6-fluoro-1,3-benzothiazol-2-yl)amino]-3-methylbiphenyl-4-yl}carbonyl)-L-valine |
| 62 | N-({4'-[(6-methoxy-1,3-benzothiazol-2-yl)amino]-3-methylbiphenyl-4-yl}carbonyl)-L-valine |
| 63 | N-{[4'-(1,3-benzothiazol-2-ylamino)-3-methylbiphenyl-4-yl]carbonyl}-L-valine |
| 64 | N-({4'-[(6-isopropyl-1,3-benzothiazol-2-yl)amino]-3-methylbiphenyl-4-yl}carbonyl)-L-valine |
| 65 | N-({4'-[(6-chloro-1,3-benzothiazol-2-yl)amino]-3-methylbiphenyl-4-yl}carbonyl)-L-valine |
| 66 | N-({4'-[(7-fluoro-1,3-benzothiazol-2-yl)amino]-3-methylbiphenyl-4-yl}carbonyl)-L-valine |
| 67 | N-({4'-[(7-chloro-1,3-benzothiazol-2-yl)amino]-3-methylbiphenyl-4-yl}carbonyl)-L-valine |
| 68 | N-{[4'-(1,3-benzothiazol-2-ylamino)-3-methoxybiphenyl-4-yl]carbonyl}-L-valine |
| 69 | N-{[4'-(1,3-benzothiazol-2-ylamino)biphenyl-4-yl]carbonyl}-L-valine |
| 70 | N-{[4'-(1,3-benzothiazol-2-ylamino)biphenyl-4-yl]carbonyl}-D-valine |
| 71 | N-({4'-[(6-chloro-1,3-benzothiazol-2-yl)amino]-3-methoxybiphenyl-4-yl}carbonyl)-L-valine |
| 72 | N-({4'-[(7-fluoro-1,3-benzothiazol-2-yl)amino]-3-methoxybiphenyl-4-yl}carbonyl)-L-valine |
| 73 | N-({4'-[(7-chloro-1,3-benzothiazol-2-yl)amino]-3-methoxybiphenyl-4-yl}carbonyl)-L-valine |
| 74 | N-({4'-[(6-isopropyl-1,3-benzothiazol-2-yl)amino]-3-methoxybiphenyl-4-yl}carbonyl)-L-valine |
| 75 | N-{[4'-(1,3-benzothiazol-2-ylamino)-3-chlorobiphenyl-4-yl]carbonyl}-L-valine |
| 76 | N-({3-chloro-4'-[(6-isopropyl-1,3-benzothiazol-2-yl)amino]biphenyl-4-yl}carbonyl)-L-valine |
| 77 | N-({3-chloro-4'-[(6-chloro-1,3-benzothiazol-2-yl)amino]biphenyl-4-yl}carbonyl)-L-valine |
| 78 | N-({3-chloro-4'-[(7-fluoro-1,3-benzothiazol-2-yl)amino]biphenyl-4-yl}carbonyl)-L-valine |
| 79 | N-({3-chloro-4'-[(7-chloro-1,3-benzothiazol-2-yl)amino]biphenyl-4-yl}carbonyl)-L-valine |
| 80 | N-{[4'-(1,3-benzothiazol-2-ylamino)-3-methoxybiphenyl-4-yl]carbonyl}-L-leucine |

TABLE 3b-continued

IUPAC Names of Compounds in Table 3a

| Example No. | IUPAC Name |
|---|---|
| 81 | N-({3-methoxy-4'-[(6-methoxy-1,3-benzothiazol-2-yl)amino]biphenyl-4-yl}carbonyl)-L-leucine |
| 82 | N-({4'-[(6-chloro-1,3-benzothiazol-2-yl)amino]-3-methoxybiphenyl-4-yl}carbonyl)-L-leucine |
| 83 | N-({4'-[(4-chloro-6-fluoro-1,3-benzothiazol-2-yl)amino]-3-methoxybiphenyl-4-yl}carbonyl)-L-leucine |
| 84 | N-({3-methoxy-4'-[(6-nitro-1,3-benzothiazol-2-yl)amino]biphenyl-4-yl}carbonyl)-L-leucine |
| 85 | N-[(3-methoxy-4'-{[6-(methylsulfonyl)-1,3-benzothiazol-2-yl]amino}biphenyl-4-yl)carbonyl]-L-leucine |
| 86 | N-({4'-[(6-isopropyl-1,3-benzothiazol-2-yl)amino]-3-methoxybiphenyl-4-yl}carbonyl)-L-leucine |

Example 87

N-({4'-[(6-methoxy-1,3-benzothiazol-2-yl)amino]biphenyl-4-yl}carbonyl)-2-methylamine

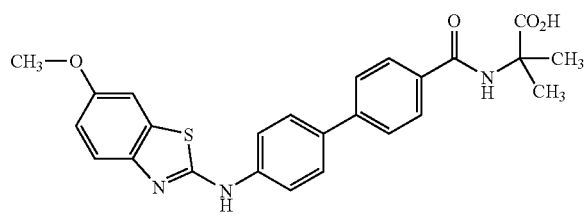

The preparation of N-({4'-[(6-methoxy-1,3-benzothiazol-2-yl)amino]biphenyl-4-yl}carbonyl)-2-methylalanine is described below in Reaction Scheme 12.

mg, 0.42 mmol, commercially available), and 1-butanol (4.0 mL) was heated at 90° C. overnight. The solvent was evaporated under reduced pressure to afford crude methyl N-({4'-[(6-methoxy-1,3-benzothiazol-2-yl)amino]biphenyl-4-yl}carbonyl)-2-methylalaninate; LC-MS m/z 476.2 (MH$^+$), retention time 3.25 minutes.

The intermediate aminobenzothiazole was dissolved in methanol (0.4 mL) and tetrahydrofuran (0.4 mL). Aqueous NaOH solution (2N, 0.64 mL, 1.28 mmol) was added, and the mixture was stirred at rt overnight. The mixture was filtered and the filtrate was purified by preparative reverse-phase HPLC (water/acetonitrile gradient, containing 0.1% TFA) to give N-({4'-[(6-methoxy-1,3-benzothiazol-2-yl)amino]biphenyl-4-yl}carbonyl)-2-methylalanine (58 mg, 39%). $^1$H NMR (400 MHz, DMSO-d$_6$) δ 1.47 (s, 6H), 3.78 (s, 3H), 6.95 (d, 1H), 7.24 (s, 1H), 7.32 (d, 1H), 7.72-7.78 (m, 4H), 7.88 (d, 2H), 7.92 (d, 2H), 8.47 (s, 1H), 10.27 (s, 1H); LC-MS m/z 462.5 (MH$^+$), retention time 2.94 minutes.

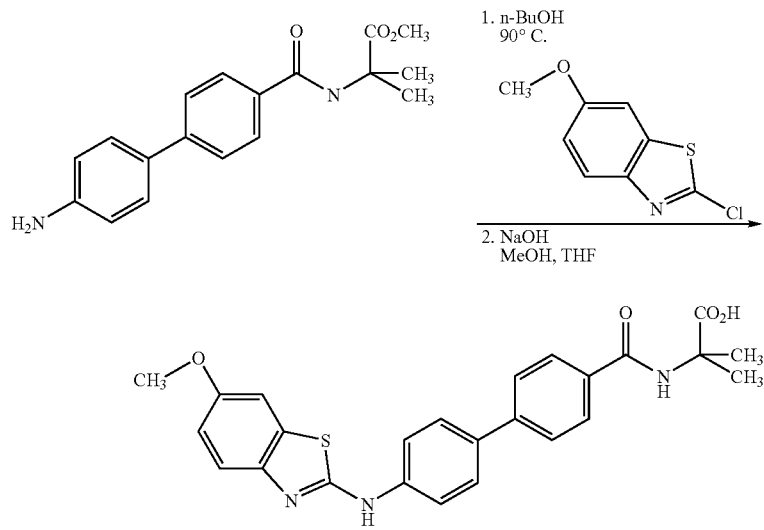

Reaction Scheme 12

As shown in Reaction Scheme 12, a mixture of methyl N-[(4'-aminobiphenyl-4-yl)carbonyl]-2-methylalaninate (100 mg, 0.32 mmol), 2-chloro-6-methoxybenzothiazole (83

By using the methods described above and by substituting the appropriate starting materials, compounds of Formula (I), listed in Table 4a below, were similarly prepared.

TABLE 4a

Preparative Examples of Compounds of Formula (I) by Method C

| Example No. | R¹ | R² | R³ | R⁴ | LC-MS retention time (min) | LC-MS [M + H]⁺ |
|---|---|---|---|---|---|---|
| 87 | 6-OMe | H | H | ![](CH₃ CH₃ / NH / CO₂H) | 2.94 | 462.4 |
| 88 | H | H | H | ![](CH₃ CH₃ / NH / CO₂H) | 2.98 | 432.2 |
| 89 | 6-Cl | H | H | ![](CH₃ CH₃ / NH / CO₂H) | 3.31 | 466.5 |
| 90 | H | H | H | ![](CH₃ / N(CH₃) / CO₂H) | 3.09 | 432.2 |
| 91 | H | H | H | ![](CH₃ CH₃ / N(CH₃) / CO₂H) | 3.33 | 460.2 |

TABLE 4b

IUPAC Names of Compounds in Table 4a

| Example No. | IUPAC Name |
|---|---|
| 87 | N-({4'-[(6-methoxy-1,3-benzothiazol-2-yl)amino]biphenyl-4-yl}carbonyl)-2-methylalanine |
| 88 | N-{[4'-(1,3-benzothiazol-2-ylamino)biphenyl-4-yl]carbonyl}-2-methylalanine |
| 89 | N-({4'-[(6-chloro-1,3-benzothiazol-2-yl)amino]biphenyl-4-yl}carbonyl)-2-methylalanine |
| 90 | N-{[4'-(1,3-benzothiazol-2-ylamino)biphenyl-4-yl]carbonyl}-N-methyl-L-alanine |
| 91 | N-{[4'-(1,3-benzothiazol-2-ylamino)biphenyl-4-yl]carbonyl}-N-methyl-L-valine |

Preparation of Intermediate V-1:
2-chloro[1,3]thiazolo[4,5-b]pyridine

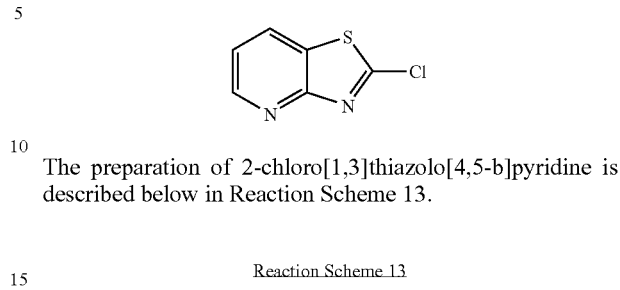

The preparation of 2-chloro[1,3]thiazolo[4,5-b]pyridine is described below in Reaction Scheme 13.

Reaction Scheme 13

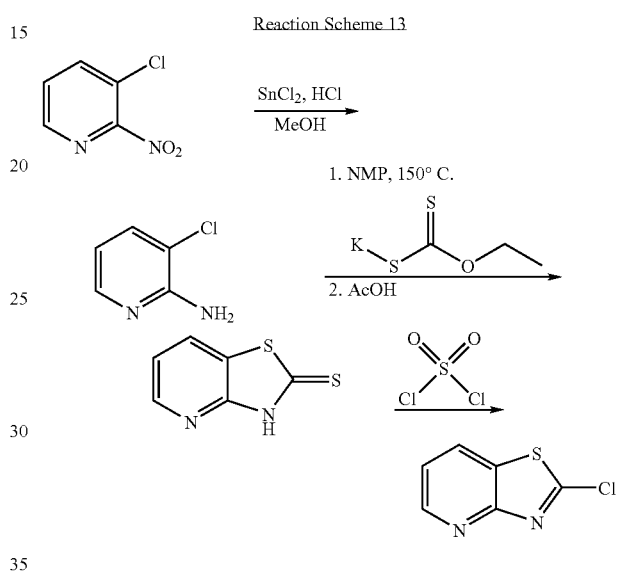

Step 1: Preparation of 2-amino-3-chloropyridine

A sample of 3-chloro-2-nitropyridine (1.00 g, 6.31 mmol) was dissolved in methanol (10 mL), treated with Tin(II) chloride (5.98 g, 31.54 mmol) followed by concentrated HCl (2.63 mL, 31.54 mmol). The reaction mixture was allowed to stir overnight at rt. The solution was then diluted with ethyl acetate and washed with 1N NaOH solution. The organic phase was then washed with concentrated $NaHCO_3$ solution and dried over $Na_2SO_4$. Concentration in vacuo gave the title compound (510.0 mg, 63%). $^1$H NMR (400 MHz, $CD_3CN$) δ 6.80 (m, 1H), 7.60 (d, 1H), 8.12 (d, 1H).

Step 2: Preparation of
[1,3]thiazolor[4,5-b]pyridine-2(3H)-thione

The intermediate 2-amino-3-chloro-pyridine (510 mg, 3.97 mmol) was dissolved in 1-methyl-2-pyrrolidinone (7 mL) and treated with potassium ethyl xanthate (953.9 mg, 5.95 mmol). The solution was heated to 150° C. overnight. The solution was then cooled to rt and treated with glacial acetic acid (1 mL) and diluted with water (150 ml). The resulting precipitate was filtered off and triturated with 1:1 water/ethanol solution. The filter cake was then suspended in EtOAc. Concentration in vacuo gave the title compound (650.0 mg, 97%). $^1$H NMR (400 MHz, DMSO-$d_6$) δ 7.25 (m, 1H), 8.11 (d, 1H), 8.35 (d, 1H).

Step 3: Preparation of 2-chloro[1,3]thiazolo[4,5-b]pyridine

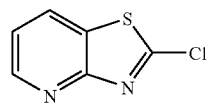

The intermediate [1,3]thiazolo[4,5-b]pyridine-2(3H)-thione (644.0 mg, 3.83 mmol, dry powder) was treated with neat sulfuryl chloride (3.08 ml, 38.28 mmol) and allowed to stir at it overnight. The reaction mixture was quenched with water and extracted with ethyl acetate. The organic layer was washed with 1N NaOH, followed by brine, and dried over $Na_2SO_4$. Concentration in vacuo gave the title compound (260.0 mg, 40%). LC/MS m/z 171.2 (MH$^+$); retention time 1.55 min. $^1$H NMR (400 MHz, DMSO-$d_6$) δ 7.58 (m, 1H), 8.62 (d, 1H), 8.78 (d, 1H).

The following intermediates of Formula (V) were prepared using the above method and the appropriate commercially available, chloro-nitro-pyridine as the starting material.

TABLE 5

Examples of Compounds of Formula (V)

| Example | Structure | LC/MS m/z (MH$^+$) | Ret. Time (min) |
|---|---|---|---|
| Intermediate V-2 | 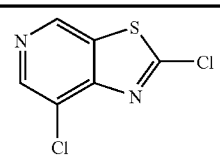 | 205.2 | 2.24 |
| Intermediate V-3 | 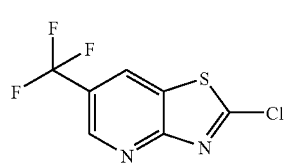 | 239.4 | 2.64 |
| Intermediate V-4 | 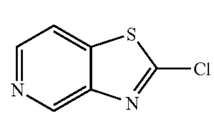 | 171.2 | 1.15 |
| Intermediate V-5 | 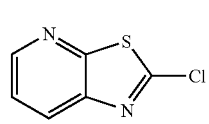 | 171.2 | 2.13 |

By using the methods described in the procedures provided herein and by substituting the appropriate starting materials, compounds of Formula (I), listed in Table 6, may be similarly prepared.

TABLE 6

Examples of Compounds of Formula (I)

| Example No. | Q | R$^1$ | R$^2$ | R$^3$ | R$^4$ | R$^5$ |
|---|---|---|---|---|---|---|
| 92 | NH | H | H | H | C(CH$_3$)$_2$(NH)CO$_2$H | H |
| 93 | NH | 6-F | F | H | C(CH$_3$)$_2$(NH)CO$_2$H | H |
| 94 | O | 6-F | F | H | C(CH$_3$)$_2$(NH)CO$_2$H | H |
| 95 | S | 6-OMe | H | CH$_3$ | C(CH$_3$)$_3$ amino acid | CH$_3$ |
| 96 | O | 6-CF$_3$ | F | H | L-Leu-OH | CH$_3$ |
| 97 | O | 5-CH$_3$ | F | H | L-Val-OH | CH$_3$ |
| 98 | O | 5-Cl | H | Cl | C(CH$_3$)$_3$ amino acid | CH$_3$ |
| 99 | S | 6-F | F | H | C(CH$_3$)$_2$(NH)CO$_2$H | CH$_2$CH$_2$OH |

By using the methods described in the procedures provided herein and by substituting the appropriate starting materials, compounds of Formula (I), listed in Table 7, were prepared.

TABLE 7a

Examples of Compounds

| Example No. | Structure | | LC-MS Ret. Time (min) | LC-MS [M + H]+ | Method |
|---|---|---|---|---|---|
| 100 | (structure) | Chiral | 2.97 | 466.1 | A |
| 101 | (structure) | Chiral | 3.04 | 484.1 | A |
| 102 | (structure) | Chiral | 3.03 | 484.1 | A |

TABLE 7a-continued

Examples of Compounds

| Example No. | Structure | | LC-MS Ret. Time (min) | LC-MS [M + H]+ | Method |
|---|---|---|---|---|---|
| 103 | 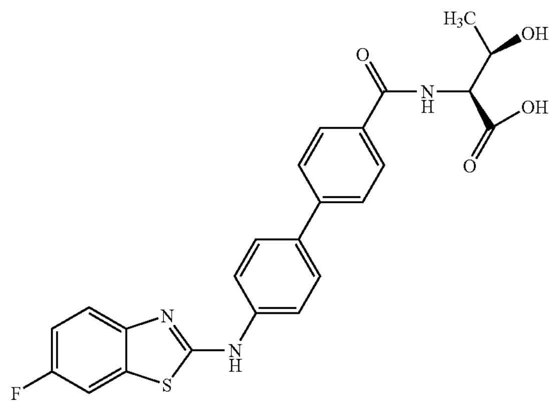 | Chiral | 2.97 | 466.1 | A |
| 104 | 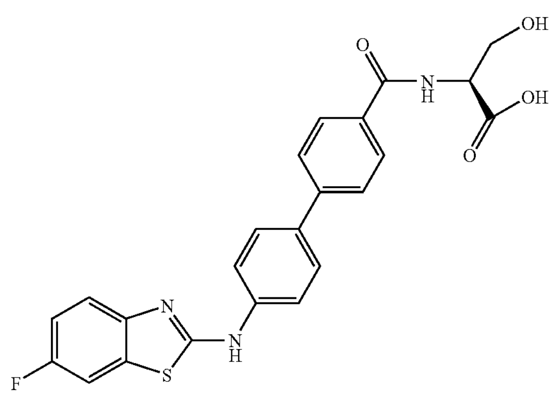 | Chiral | 2.88 | 452.1 | A |
| 105 | 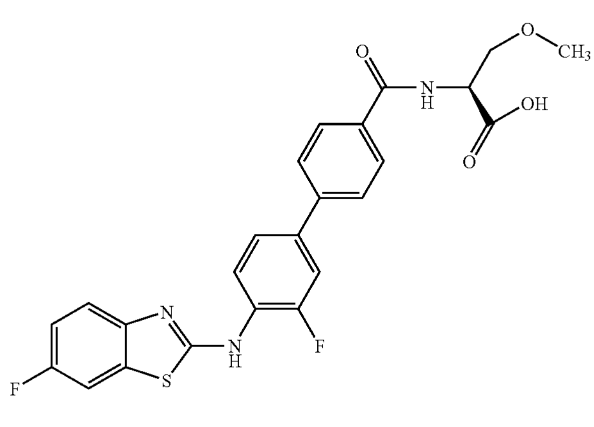 | Chiral | 3.19 | 484.1 | A |

TABLE 7a-continued

Examples of Compounds

| Example No. | Structure | | LC-MS Ret. Time (min) | LC-MS [M + H]+ | Method |
|---|---|---|---|---|---|
| 106 | (structure) | Chiral | 3.48 | 494.1 | A |
| 107 | (structure) | Chiral | 3.14 | 466.1 | A |
| 108 | (structure) | Chiral | 3.41 | 476.2 | A |

TABLE 7a-continued

Examples of Compounds

| Example No. | Structure | | LC-MS Ret. Time (min) | LC-MS [M + H]+ | Method |
|---|---|---|---|---|---|
| 109 | 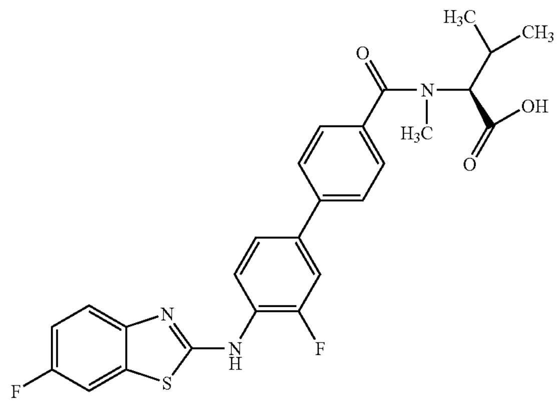 | Chiral | 3.53 | 496.1 | A |
| 110 | 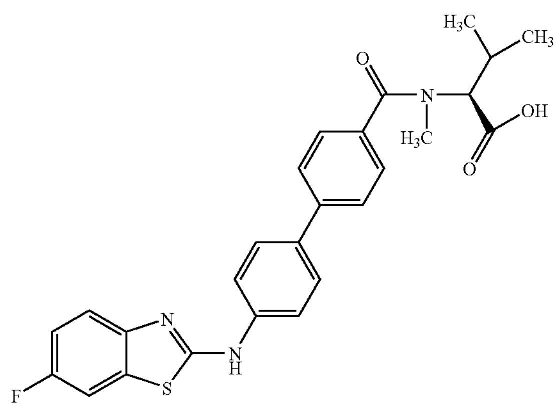 | Chiral | 3.43 | 478.2 | A |
| 111 | 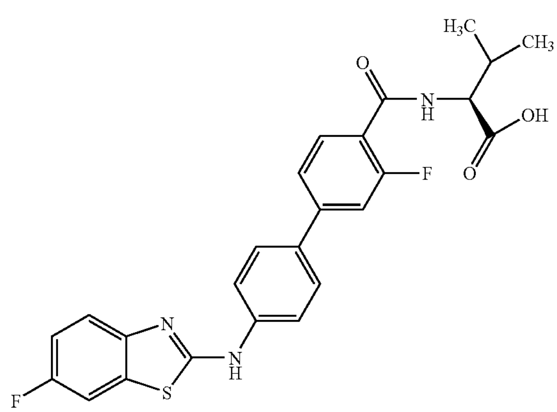 | Chiral | 3.52 | 482.2 | A |

TABLE 7a-continued

Examples of Compounds

| Example No. | Structure | | LC-MS Ret. Time (min) | LC-MS [M + H]+ | Method |
|---|---|---|---|---|---|
| 112 | (structure) | Chiral | 3.66 | 496.2 | A |
| 113 | (structure) | Chiral | 3.66 | 496.2 | A |
| 114 | (structure) | Chiral | 3.67 | 496.2 | A |

TABLE 7a-continued
Examples of Compounds
| Example No. | Structure | | LC-MS Ret. Time (min) | LC-MS [M + H]+ | Method |
|---|---|---|---|---|---|
| 115 | 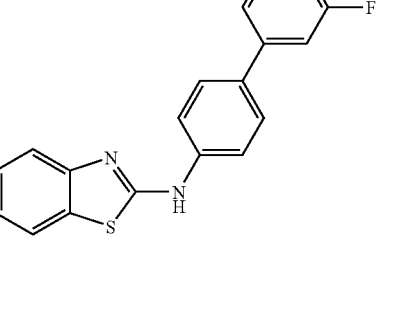 | Chiral | 3.53 | 482.2 | A |
| 116 | 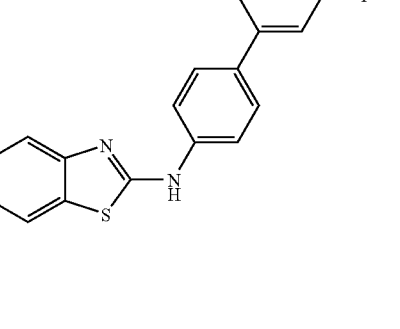 | Chiral | 3.39 | 468.2 | A |
| 117 | 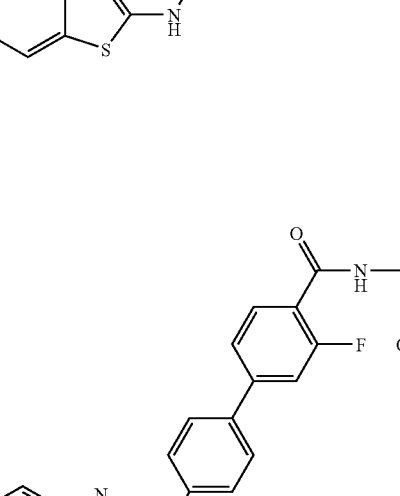 | Chiral | 3.56 | 494.2 | A |

TABLE 7a-continued

Examples of Compounds

| Example No. | Structure | | LC-MS Ret. Time (min) | LC-MS [M + H]+ | Method |
|---|---|---|---|---|---|
| 118 | 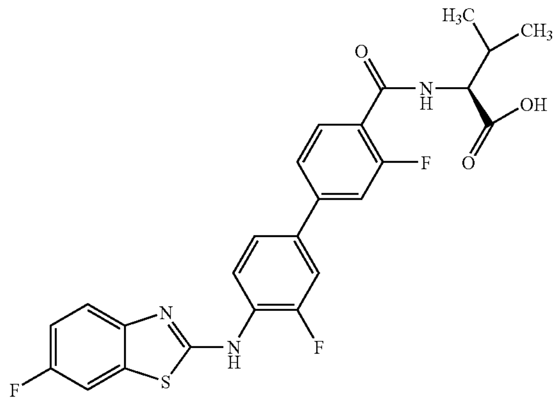 | Chiral | 3.6 | 500.2 | A |
| 119 | 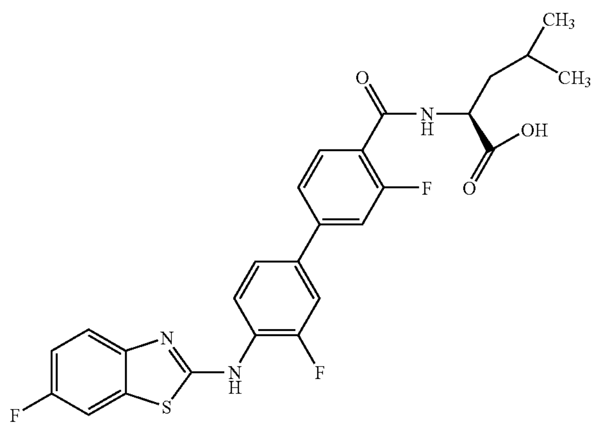 | Chiral | 3.72 | 514.2 | A |
| 120 | 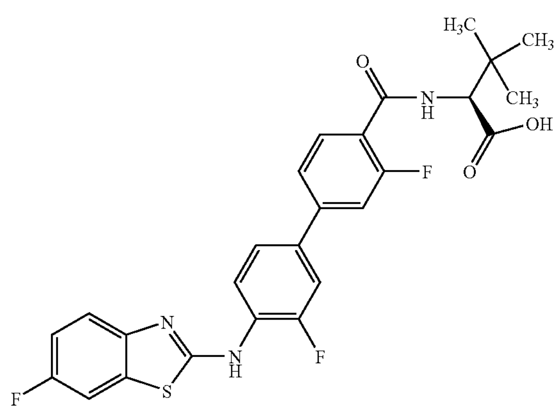 | Chiral | 3.74 | 514.2 | A |

TABLE 7a-continued
Examples of Compounds
| Example No. | Structure | | LC-MS Ret. Time (min) | LC-MS [M + H]+ | Method |
|---|---|---|---|---|---|
| 121 | 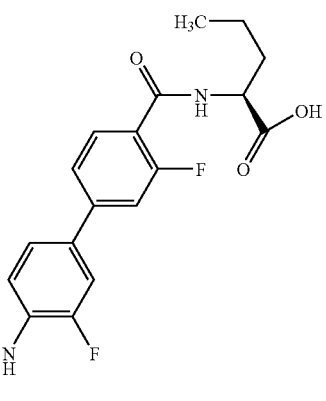 | Chiral | 3.61 | 500.1 | A |
| 122 | 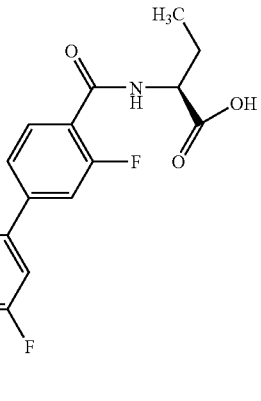 | Chiral | 3.47 | 485.1 | A |
| 123 | 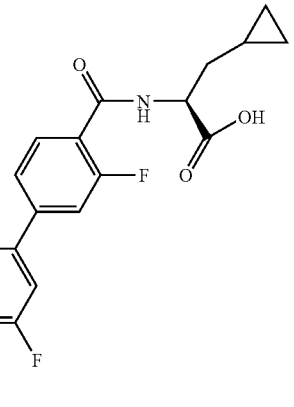 | Chiral | 3.64 | 512.1 | A |

TABLE 7a-continued

Examples of Compounds

| Example No. | Structure | | LC-MS Ret. Time (min) | LC-MS [M + H]+ | Method |
|---|---|---|---|---|---|
| 124 | 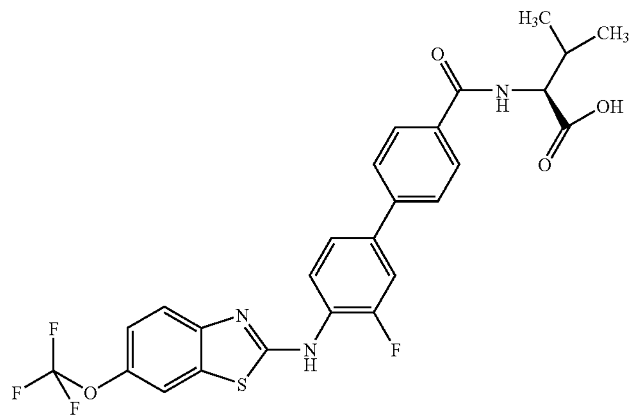 | Chiral | 4.27 | 548.2 | A |
| 125 | 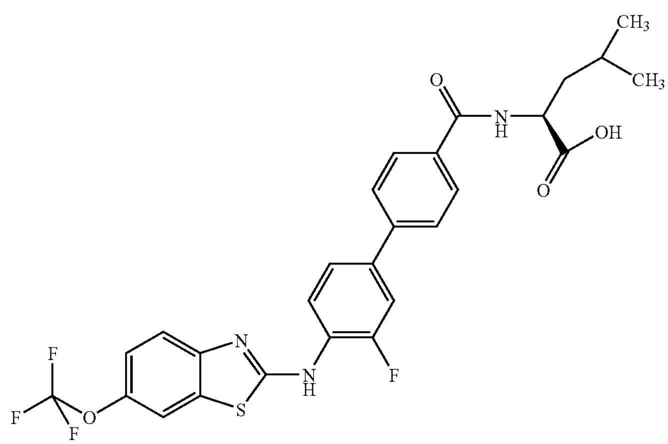 | Chiral | 4.56 | 562.2 | A |
| 126 | 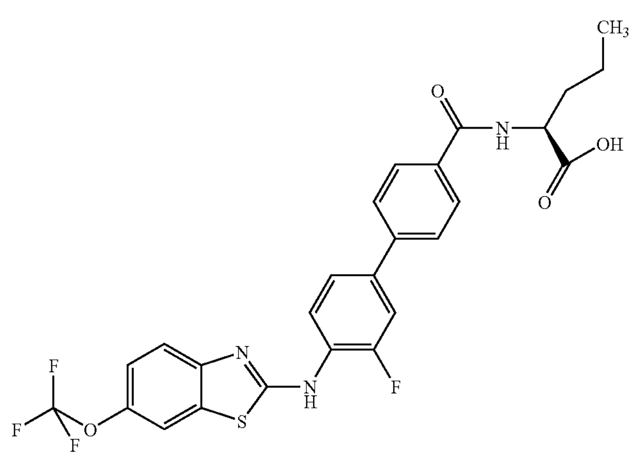 | Chiral | 4.23 | 562.1 | A |

TABLE 7a-continued

Examples of Compounds

| Example No. | Structure | | LC-MS Ret. Time (min) | LC-MS [M + H]+ | Method |
|---|---|---|---|---|---|
| 127 | 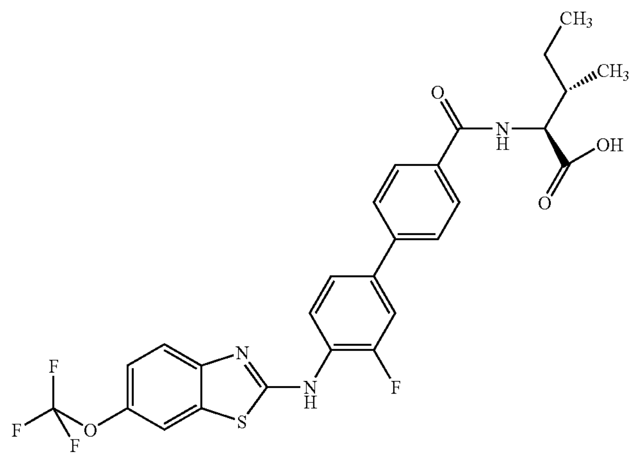 | Chiral | 4.56 | 562.1 | A |
| 128 | 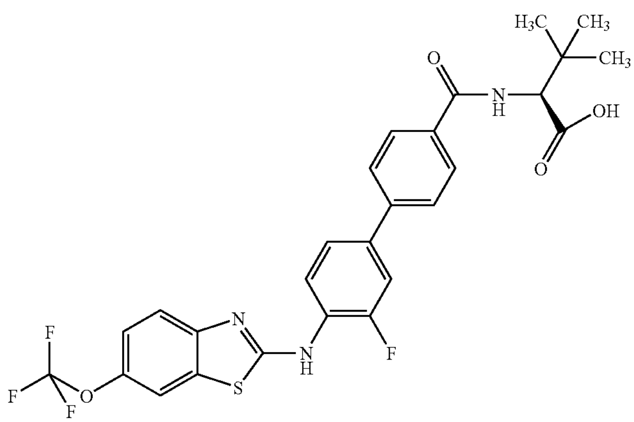 | Chiral | 4.45 | 562.2 | A |
| 129 | 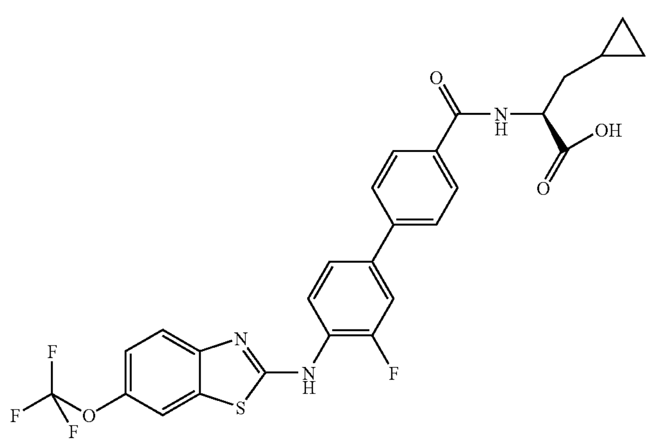 | Chiral | 4.47 | 560.2 | A |

TABLE 7a-continued

Examples of Compounds

| Example No. | Structure | | LC-MS Ret. Time (min) | LC-MS [M + H]+ | Method |
|---|---|---|---|---|---|
| 130 | 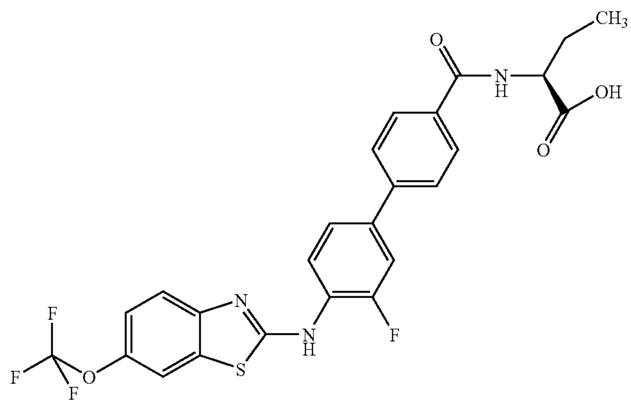 | Chiral | 4.28 | 534.1 | A |
| 131 | 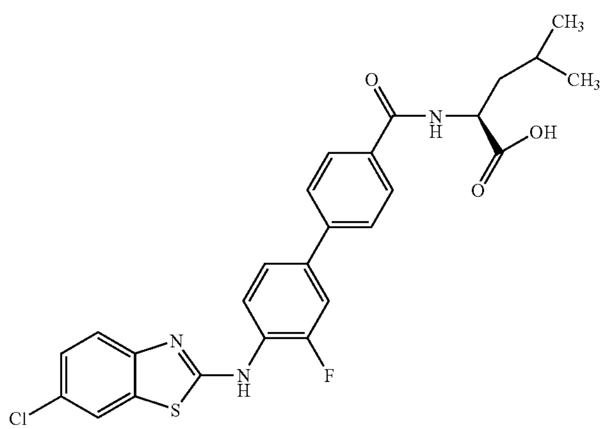 | Chiral | 3.79 | 512.1 | A |
| 132 | 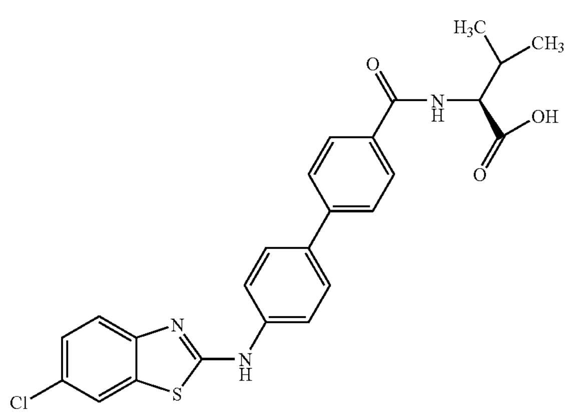 | Chiral | 3.57 | 480.1 | A |

TABLE 7a-continued

Examples of Compounds

| Example No. | Structure | | LC-MS Ret. Time (min) | LC-MS [M + H]+ | Method |
|---|---|---|---|---|---|
| 133 | (structure) | Chiral | 3.71 | 494.1 | A |
| 134 | (structure) | Chiral | 3.59 | 480.1 | A |
| 135 | (structure) | Chiral | 3.71 | 494.1 | A |

TABLE 7a-continued

Examples of Compounds

| Example No. | Structure | | LC-MS Ret. Time (min) | LC-MS [M + H]+ | Method |
|---|---|---|---|---|---|
| 136 | 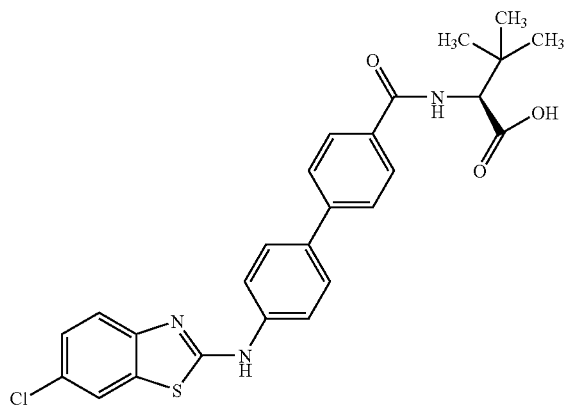 | Chiral | 3.7 | 494.1 | A |
| 137 | 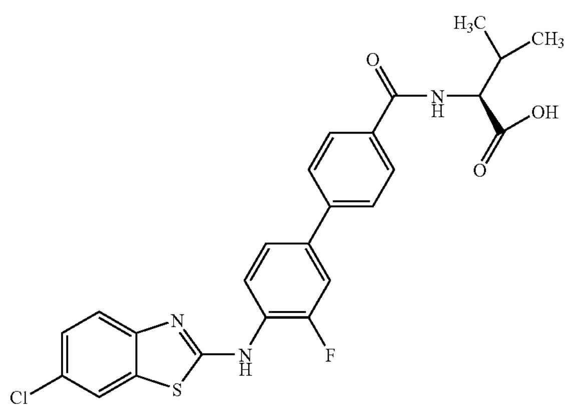 | Chiral | 3.63 | 498.1 | A |
| 138 | 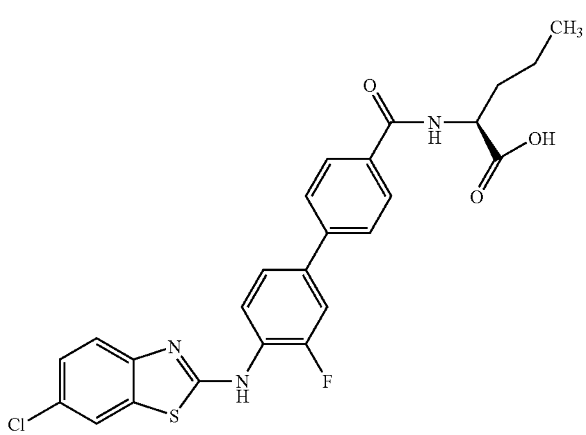 | Chiral | 3.65 | 498.1 | A |

TABLE 7a-continued
Examples of Compounds
| Example No. | Structure | | LC-MS Ret. Time (min) | LC-MS [M + H]+ | Method |
|---|---|---|---|---|---|
| 139 | 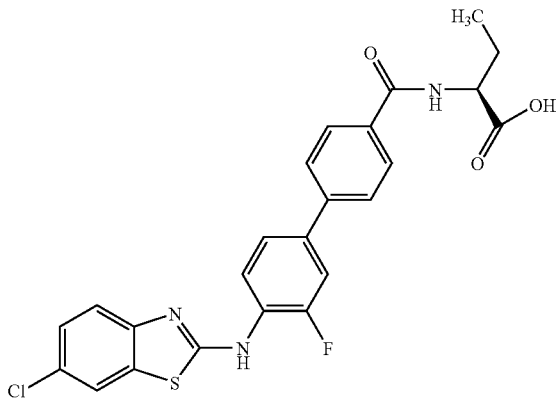 | Chiral | 3.51 | 484.1 | A |
| 140 | 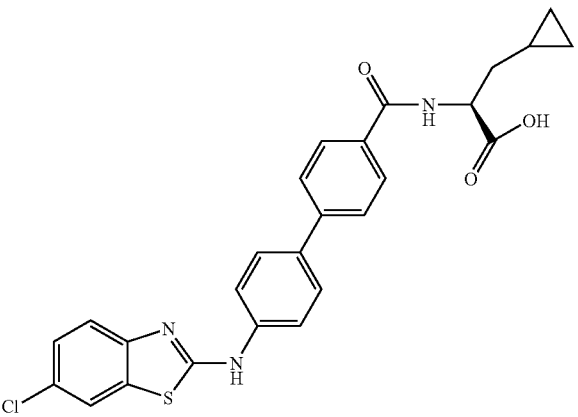 | Chiral | 3.61 | 492.1 | A |
| 141 | 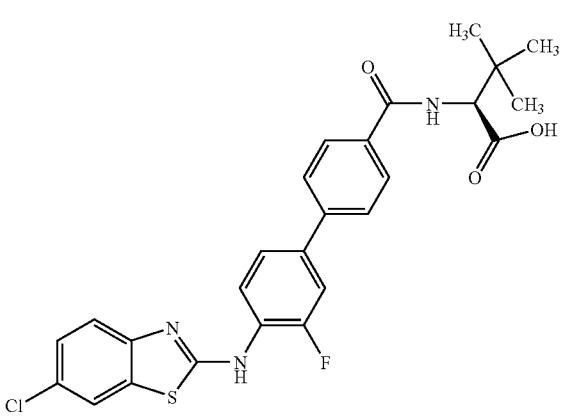 | Chiral | 3.78 | 512.1 | A |

TABLE 7a-continued

Examples of Compounds

| Example No. | Structure | LC-MS Ret. Time (min) | LC-MS [M + H]+ | Method |
|---|---|---|---|---|
| 142 | Chiral | 3.44 | 466.1 | A |
| 143 | Chiral | 2.95 | 447.2 | C |
| 144 | Chiral | 2.23 | 447.2 | C |

TABLE 7a-continued

Examples of Compounds

| Example No. | Structure | | LC-MS Ret. Time (min) | LC-MS [M + H]+ | Method |
|---|---|---|---|---|---|
| 145 | 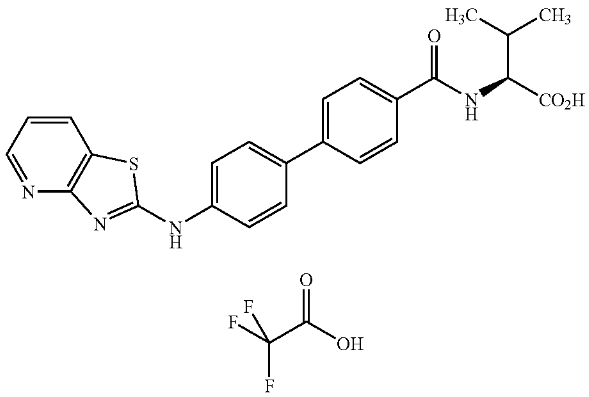 | Chiral | 2.35 | 447.2 | C |
| 146 | 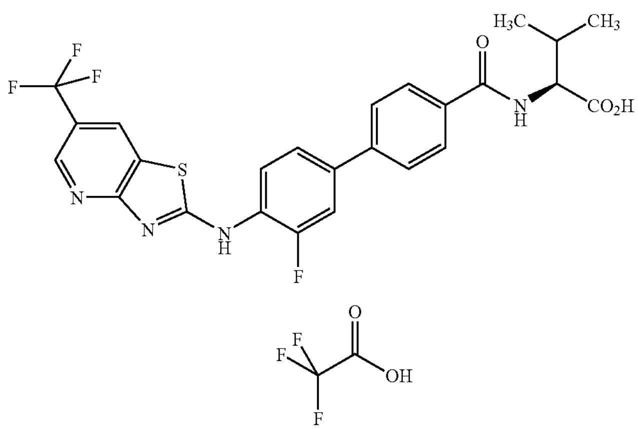 | Chiral | 3.32 | 533.2 | C |
| 147 | 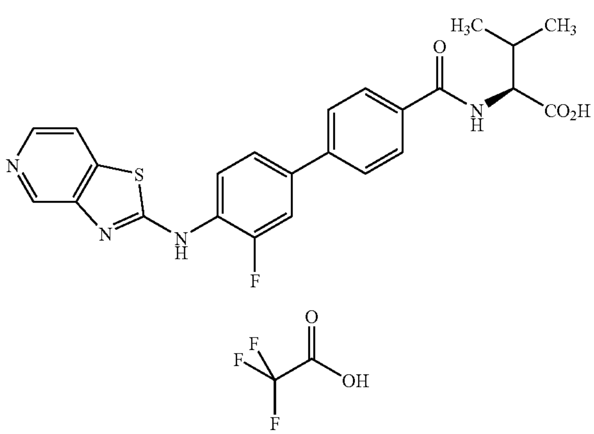 | Chiral | 2.25 | 465.2 | C |

TABLE 7a-continued

Examples of Compounds

| Example No. | Structure | | LC-MS Ret. Time (min) | LC-MS [M + H]+ | Method |
|---|---|---|---|---|---|
| 148 | 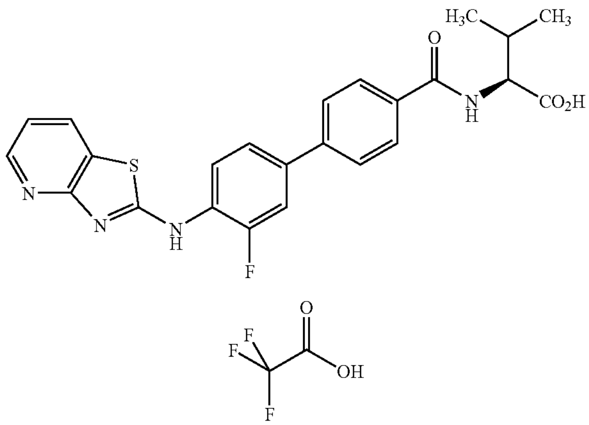 | Chiral | 2.42 | 465.2 | C |
| 149 | 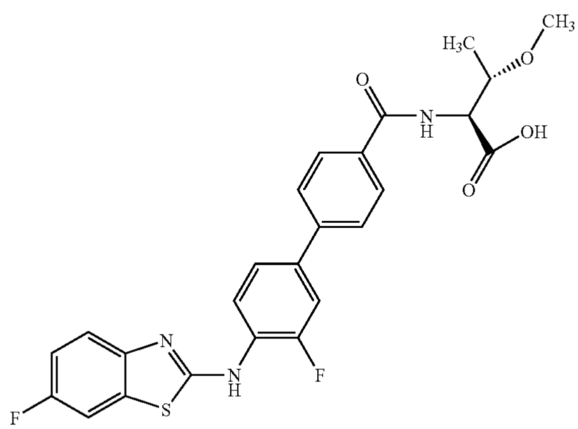 | Chiral | 3.27 | 498.1 | A |
| 150 | 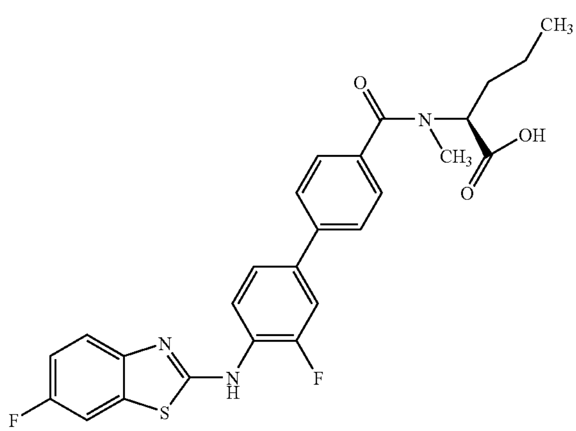 | Chiral | 3.53 | 496.1 | A |

TABLE 7a-continued

Examples of Compounds

| Example No. | Structure | LC-MS Ret. Time (min) | LC-MS [M + H]+ | Method |
|---|---|---|---|---|
| 151 | 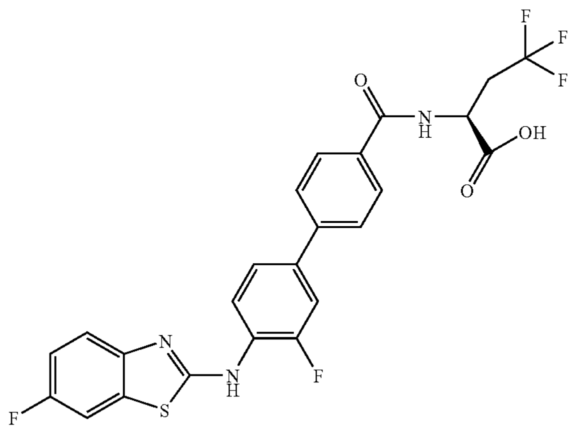 | 3.49 | 522.2 | A |
| 152 | Chiral | 3.51 | 494.1 | A |
| 153 | Chiral | 3.67 | 508.2 | A |

TABLE 7a-continued

Examples of Compounds

| Example No. | Structure | LC-MS Ret. Time (min) | LC-MS [M + H]+ | Method |
|---|---|---|---|---|
| 154 | Chiral | 3.54 | 516.1 | A |
| 155 | Chiral | 3.24 | 480.2 | A |
| 156 | Chiral | 3.46 | 478.2 | A |

TABLE 7a-continued

Examples of Compounds

| Example No. | Structure | | LC-MS Ret. Time (min) | LC-MS [M + H]+ | Method |
|---|---|---|---|---|---|
| 157 | 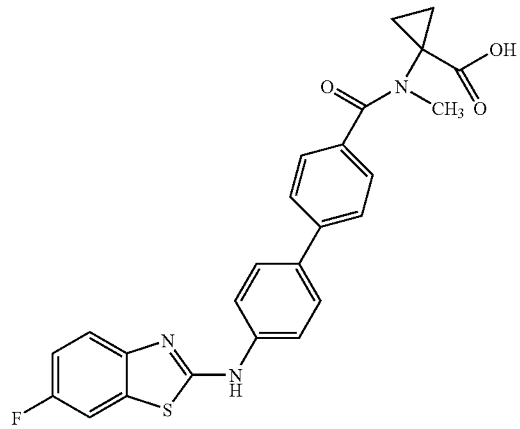 | | 3.16 | 462.1 | A |
| 158 | 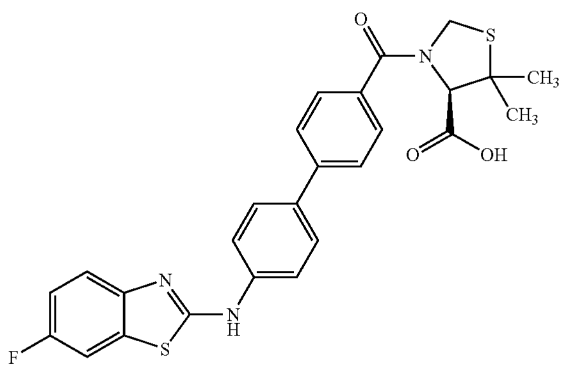 | Chiral | 3.55 | 508.1 | A |
| 159 | 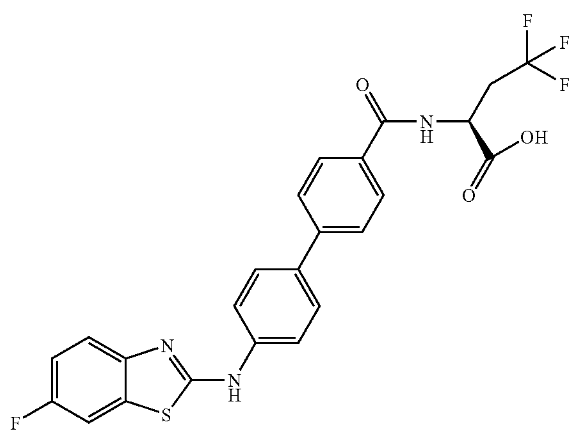 | | 3.41 | 504.1 | A |

TABLE 7a-continued

Examples of Compounds

| Example No. | Structure | | LC-MS Ret. Time (min) | LC-MS [M + H]+ | Method |
|---|---|---|---|---|---|
| 160 | 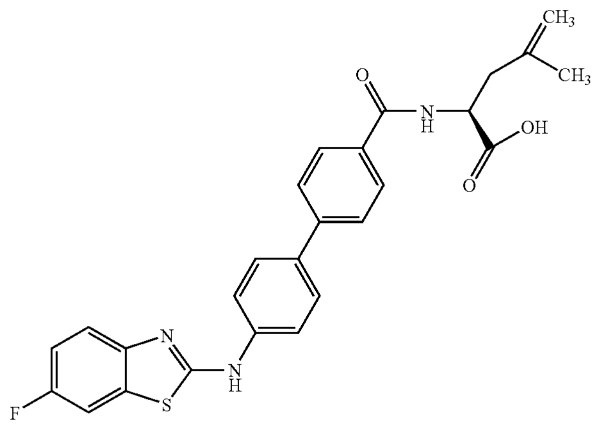 | Chiral | 3.42 | 476.2 | A |
| 161 | 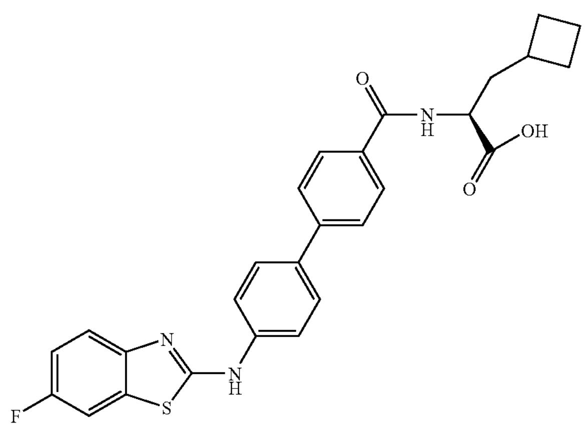 | Chiral | 3.59 | 490.2 | A |
| 162 | 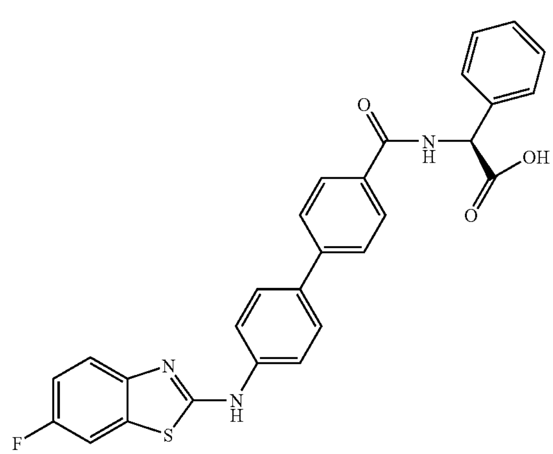 | Chiral | 3.47 | 498.2 | A |

TABLE 7a-continued

Examples of Compounds

| Example No. | Structure | | LC-MS Ret. Time (min) | LC-MS [M + H]+ | Method |
|---|---|---|---|---|---|
| 163 | [structure] | Chiral | 3.72 | 532.2 | A |
| 164 | [structure] | Chiral | 3.87 | 546.2 | A |
| 165 | [structure] | Chiral | 3.74 | 532.2 | A |

TABLE 7a-continued

Examples of Compounds

| Example No. | Structure | | LC-MS Ret. Time (min) | LC-MS [M + H]+ | Method |
|---|---|---|---|---|---|
| 166 | 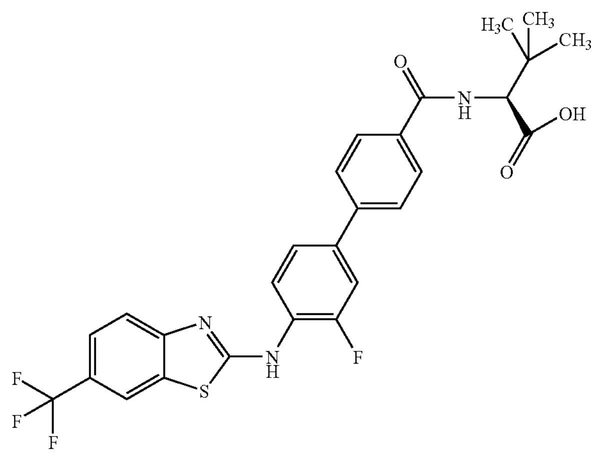 | Chiral | 3.84 | 546.2 | A |
| 167 | 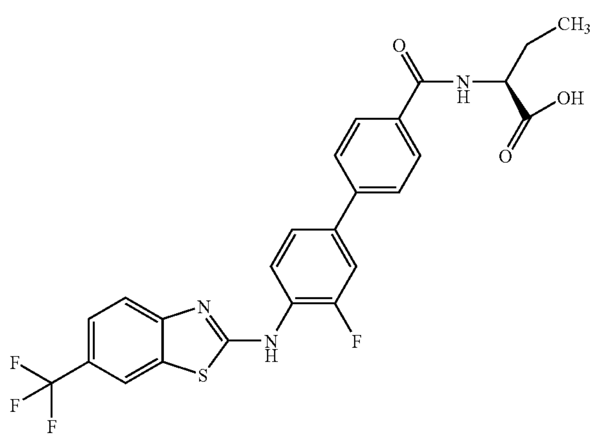 | Chiral | 3.6 | 518.2 | A |
| 168 | 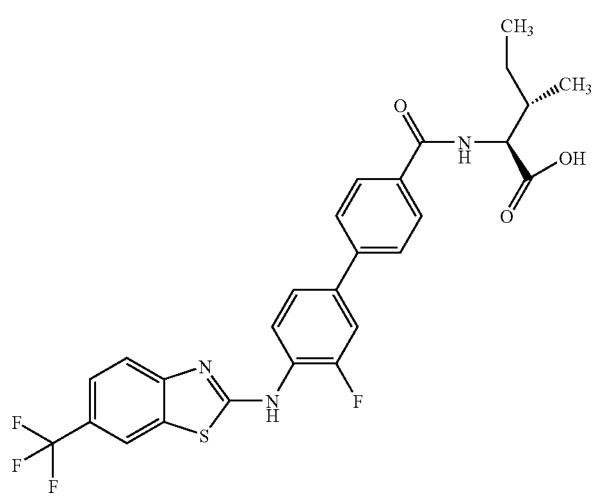 | Chiral | 3.86 | 546.2 | A |

TABLE 7a-continued

Examples of Compounds

| Example No. | Structure | | LC-MS Ret. Time (min) | LC-MS [M + H]+ | Method |
|---|---|---|---|---|---|
| 169 | 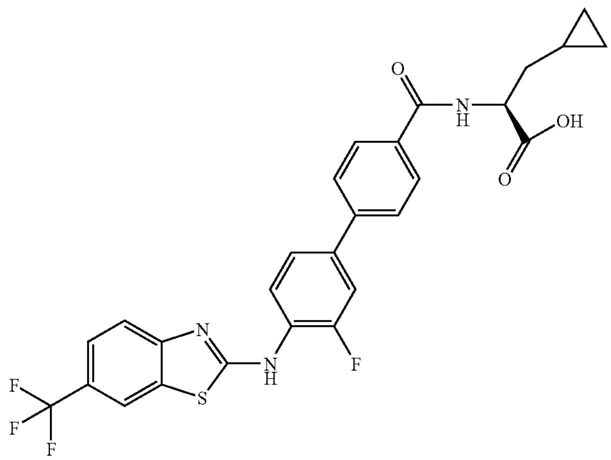 | Chiral | 3.74 | 544.2 | A |
| 170 | 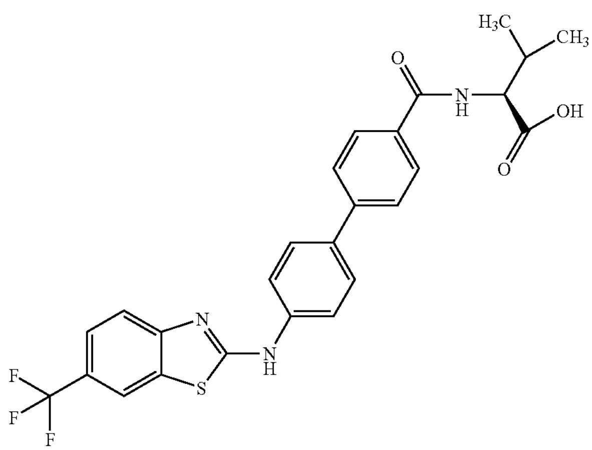 | Chiral | 3.66 | 514.2 | A |
| 171 | 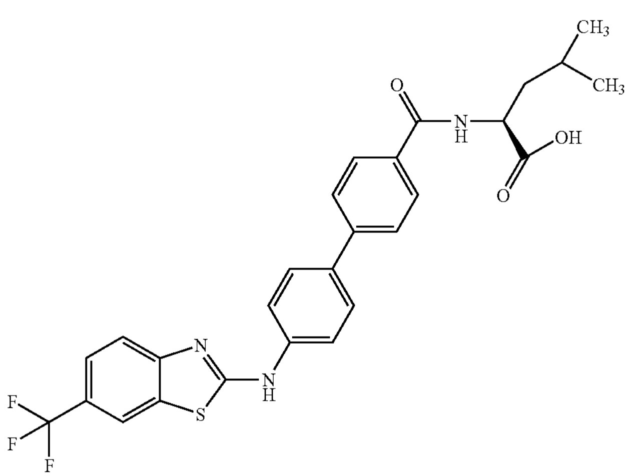 | Chiral | 3.79 | 528.2 | A |

TABLE 7a-continued

Examples of Compounds

| Example No. | Structure | | LC-MS Ret. Time (min) | LC-MS [M + H]+ | Method |
|---|---|---|---|---|---|
| 172 | (structure) | Chiral | 3.68 | 514.2 | A |
| 173 | (structure) | Chiral | 3.77 | 528.2 | A |
| 174 | (structure) | Chiral | 3.54 | 500.2 | A |

TABLE 7a-continued

Examples of Compounds

| Example No. | Structure | | LC-MS Ret. Time (min) | LC-MS [M + H]+ | Method |
|---|---|---|---|---|---|
| 175 | 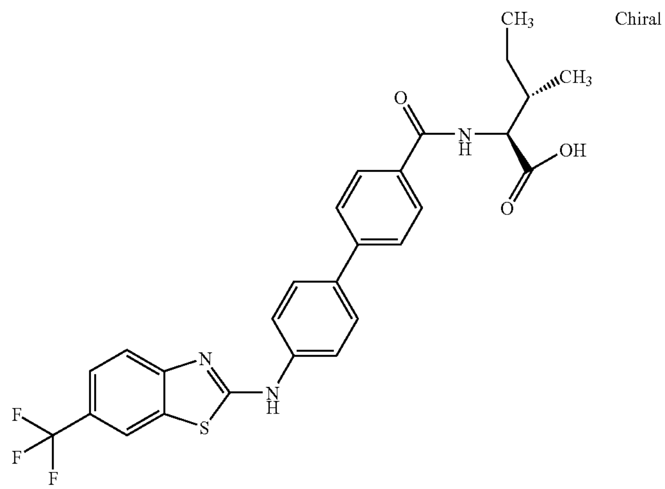 | Chiral | 3.78 | 528.2 | A |
| 176 | 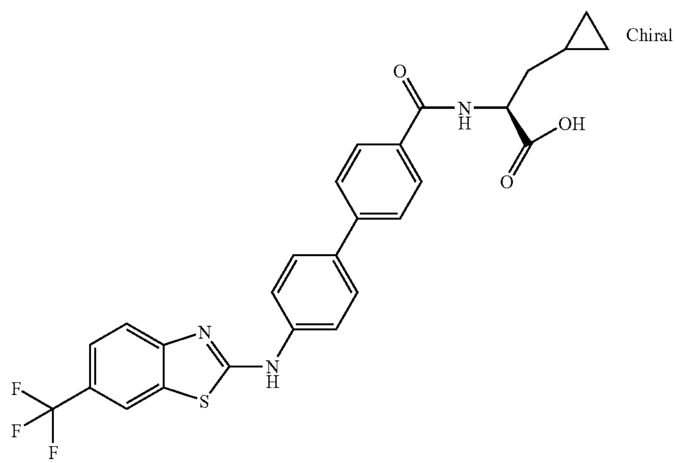 | Chiral | 3.68 | 526.2 | A |
| 177 | 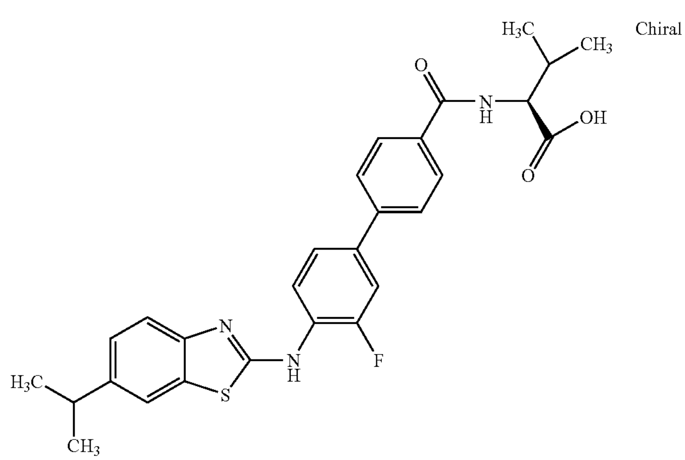 | Chiral | 3.74 | 506.2 | A |

TABLE 7a-continued
Examples of Compounds
| Example No. | Structure | | LC-MS Ret. Time (min) | LC-MS [M + H]+ | Method |
|---|---|---|---|---|---|
| 178 | 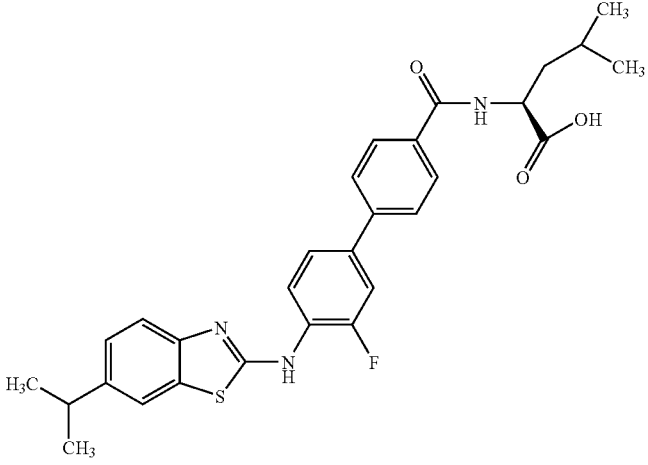 | Chiral | 3.88 | 520.2 | A |
| 179 | 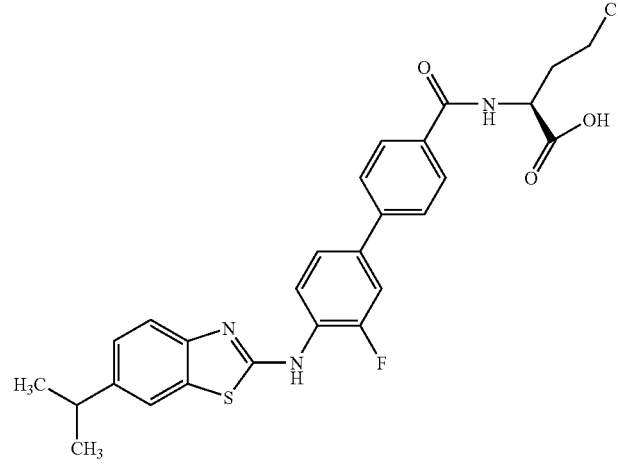 | Chiral | 3.75 | 506.2 | A |
| 180 | 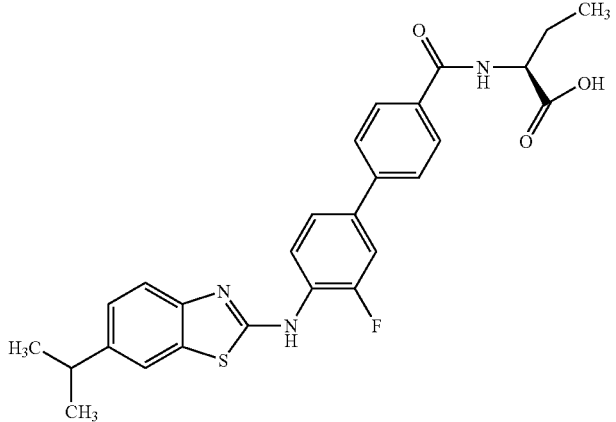 | Chiral | 3.62 | 492.2 | A |

TABLE 7a-continued

Examples of Compounds

| Example No. | Structure | | LC-MS Ret. Time (min) | LC-MS [M + H]+ | Method |
|---|---|---|---|---|---|
| 181 | 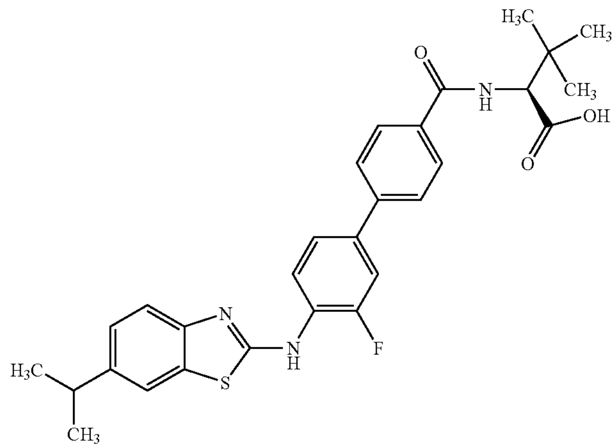 | Chiral | 3.87 | 520.2 | A |
| 182 | 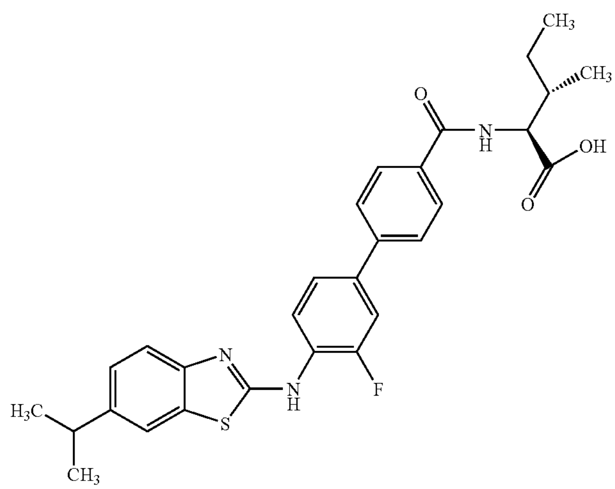 | Chiral | 3.87 | 520.2 | A |
| 183 | 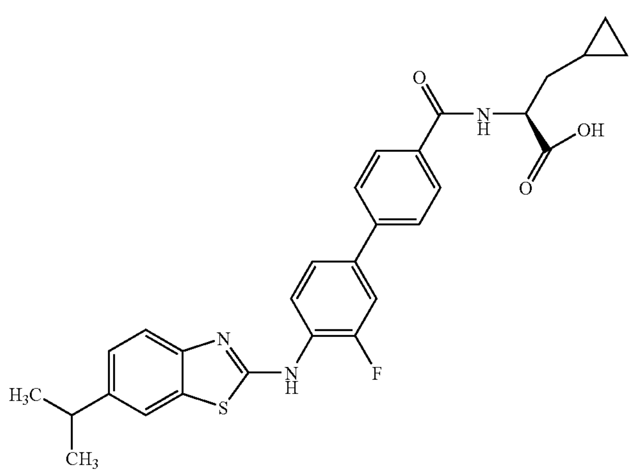 | Chiral | 3.77 | 518.2 | A |

TABLE 7a-continued

Examples of Compounds

| Example No. | Structure | | LC-MS Ret. Time (min) | LC-MS [M + H]+ | Method |
|---|---|---|---|---|---|
| 184 | (structure) | Chiral | 3.37 | 529.2 | A |
| 185 | (structure) | Chiral | 3.23 | 515.2 | A |

TABLE 7a-continued
Examples of Compounds
| Example No. | Structure | | LC-MS Ret. Time (min) | LC-MS [M + H]+ | Method |
|---|---|---|---|---|---|
| 186 | 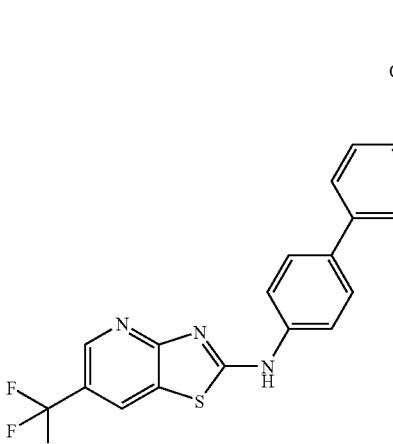 | Chiral | 3.35 | 529.2 | A |
| 187 | 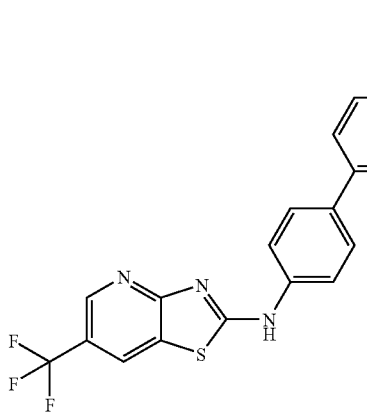 | Chiral | 3.11 | 501.2 | A |

TABLE 7a-continued

Examples of Compounds

| Example No. | Structure | | LC-MS Ret. Time (min) | LC-MS [M + H]+ | Method |
|---|---|---|---|---|---|
| 188 | 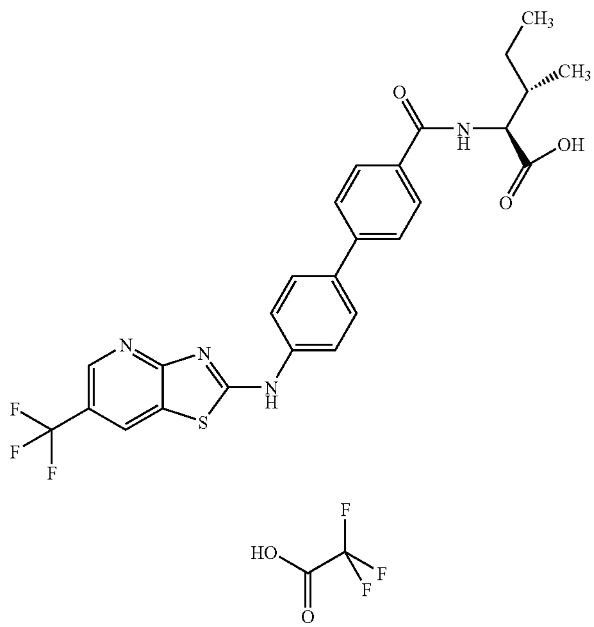 | Chiral | 3.35 | 529.2 | A |
| 189 | 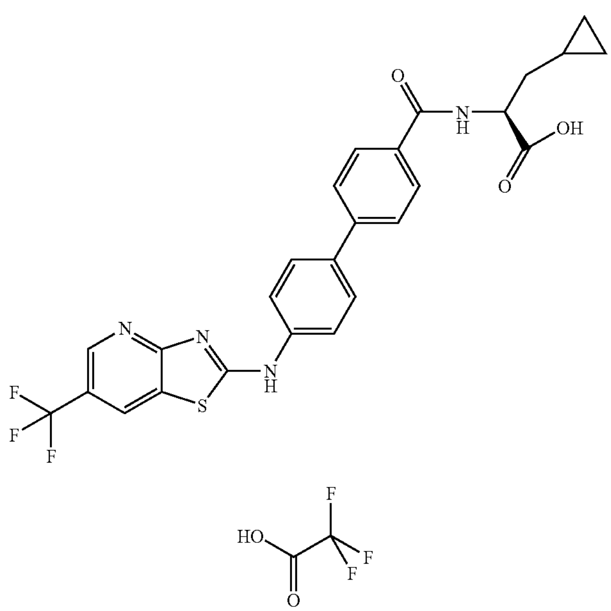 | Chiral | 3.25 | 527.2 | A |

TABLE 7a-continued
Examples of Compounds
| Example No. | Structure | | LC-MS Ret. Time (min) | LC-MS [M + H]+ | Method |
|---|---|---|---|---|---|
| 190 | 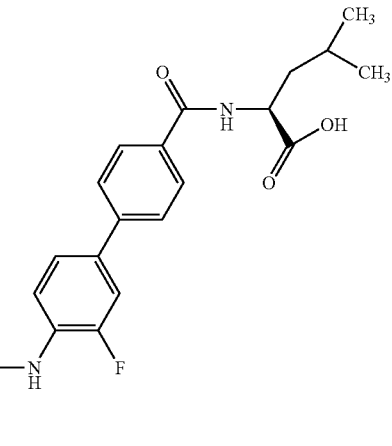 | Chiral | 3.43 | 547.2 | A |
| 191 | 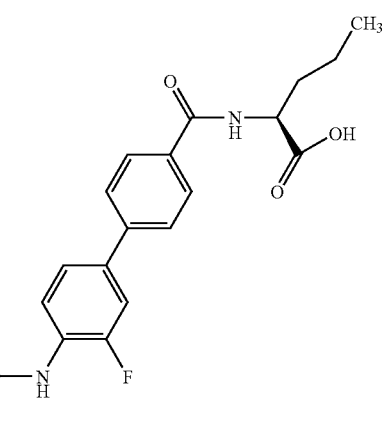 | Chiral | 3.3 | 533.2 | A |

TABLE 7a-continued
Examples of Compounds
| Example No. | Structure | | LC-MS Ret. Time (min) | LC-MS [M + H]+ | Method |
|---|---|---|---|---|---|
| 192 | 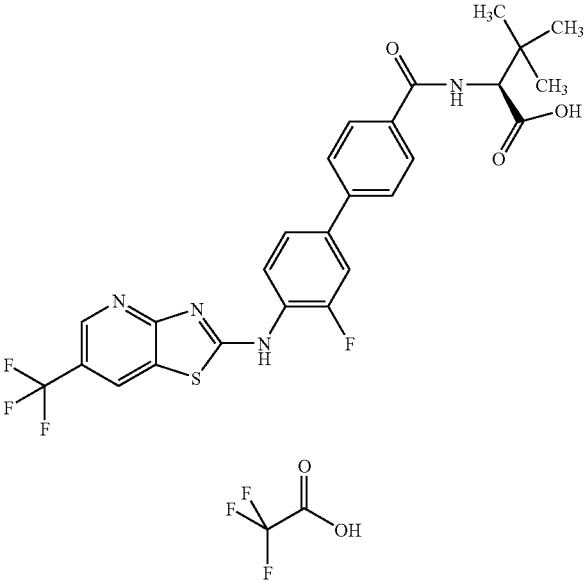 | Chiral | 3.4 | 547.2 | A |
| 193 | 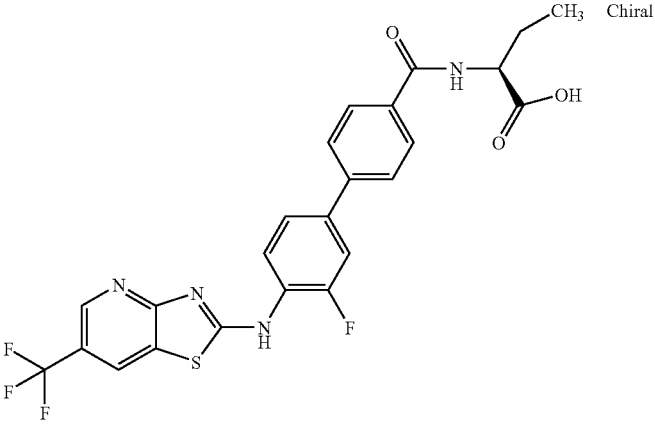 | Chiral | 3.17 | 519.2 | A |

TABLE 7a-continued

Examples of Compounds

| Example No. | Structure | | LC-MS Ret. Time (min) | LC-MS [M + H]+ | Method |
|---|---|---|---|---|---|
| 194 | [structure] | Chiral | 3.42 | 547.2 | A |
| 195 | [structure] | Chiral | 2.7 | 499.1 | C |

TABLE 7b

IUPAC Names of Compounds in Table 7a

| Example No. | IUPAC Name |
|---|---|
| 100 | N-({4'-[(6-Fluoro-1,3-benzothiazol-2-yl)amino]biphenyl-4-yl}carbonyl)-L-allothreonine |
| 101 | N-({3'-Fluoro-4'-[(6-fluoro-1,3-benzothiazol-2-yl)amino]biphenyl-4-yl}carbonyl)-L-allothreonine |
| 102 | N-({3'-Fluoro-4'-[(6-fluoro-1,3-benzothiazol-2-yl)amino]biphenyl-4-yl}carbonyl)-L-threonine |
| 103 | N-({4'-[(6-Fluoro-1,3-benzothiazol-2-yl)amino]biphenyl-4-yl}carbonyl)-L-threonine |
| 104 | N-({4'-[(6-Fluoro-1,3-benzothiazol-2-yl)amino]biphenyl-4-yl}carbonyl)-L-serine |
| 105 | N-({3'-Fluoro-4'-[(6-fluoro-1,3-benzothiazol-2-yl)amino]biphenyl-4-yl}carbonyl)-O-methyl-L-serine |

TABLE 7b-continued

IUPAC Names of Compounds in Table 7a

| Example No. | IUPAC Name |
|---|---|
| 106 | 3-Cyclopropyl-N-({3'-fluoro-4'-[(6-fluoro-1,3-benzothiazol-2-yl)amino]biphenyl-4-yl}carbonyl)-L-alanine |
| 107 | N-({4'-[(6-Fluoro-1,3-benzothiazol-2-yl)amino]biphenyl-4-yl}carbonyl)-O-methyl-L-serine |
| 108 | 3-Cyclopropyl-N-({4'-[(6-fluoro-1,3-benzothiazol-2-yl)amino]biphenyl-4-yl}carbonyl)-L-alanine |
| 109 | N-({3'-Fluoro-4'-[(6-fluoro-1,3-benzothiazol-2-yl)amino]biphenyl-4-yl}carbonyl)-N-methyl-L-valine |
| 110 | N-({4'-[(6-Fluoro-1,3-benzothiazol-2-yl)amino]biphenyl-4-yl}carbonyl)-N-methyl-L-valine |
| 111 | N-({3-Fluoro-4'-[(6-fluoro-1,3-benzothiazol-2-yl)amino]biphenyl-4-yl}carbonyl)-L-valine |
| 112 | N-({3-Fluoro-4'-[(6-fluoro-1,3-benzothiazol-2-yl)amino]biphenyl-4-yl}carbonyl)-L-leucine |
| 113 | N-({3-Fluoro-4'-[(6-fluoro-1,3-benzothiazol-2-yl)amino]biphenyl-4-yl}carbonyl)-3-methyl-L-valine |
| 114 | N-({3-Fluoro-4'-[(6-fluoro-1,3-benzothiazol-2-yl)amino]biphenyl-4-yl}carbonyl)-L-isoleucine |
| 115 | N-({3-Fluoro-4'-[(6-fluoro-1,3-benzothiazol-2-yl)amino]biphenyl-4-yl}carbonyl)-L-norvaline |
| 116 | (2S)-2-[({3-Fluoro-4'-[(6-fluoro-1,3-benzothiazol-2-yl)amino]biphenyl-4-yl}carbonyl)amino]butanoic acid |
| 117 | 3-Cyclopropyl-N-({3-fluoro-4'-[(6-fluoro-1,3-benzothiazol-2-yl)amino]biphenyl-4-yl}carbonyl)-L-alanine |
| 118 | N-({3,3'-Difluoro-4'-[(6-fluoro-1,3-benzothiazol-2-yl)amino]biphenyl-4-yl}carbonyl)-L-valine |
| 119 | N-({3,3'-Difluoro-4'-[(6-fluoro-1,3-benzothiazol-2-yl)amino]biphenyl-4-yl}carbonyl)-L-leucine |
| 120 | N-({3,3'-Difluoro-4'-[(6-fluoro-1,3-benzothiazol-2-yl)amino]biphenyl-4-yl}carbonyl)-3-methyl-L-valine |
| 121 | N-({3,3'-Difluoro-4'-[(6-fluoro-1,3-benzothiazol-2-yl)amino]biphenyl-4-yl}carbonyl)-L-norvaline |
| 122 | (2S)-2-[({3,3'-Difluoro-4'-[(6-fluoro-1,3-benzothiazol-2-yl)amino]biphenyl-4-yl}carbonyl)amino]butanoic acid |
| 123 | 3-Cyclopropyl-N-({3,3'-difluoro-4'-[(6-fluoro-1,3-benzothiazol-2-yl)amino]biphenyl-4-yl}carbonyl)-L-alanine |
| 124 | N-[(3'-Fluoro-4'-{[6-(trifluoromethoxy)-1,3-benzothiazol-2-yl]amino}biphenyl-4-yl)carbonyl]-L-valine |
| 125 | N-[(3'-Fluoro-4'-{[6-(trifluoromethoxy)-1,3-benzothiazol-2-yl]amino}biphenyl-4-yl)carbonyl]-L-leucine |
| 126 | N-[(3'-Fluoro-4'-{[6-(trifluoromethoxy)-1,3-benzothiazol-2-yl]amino}biphenyl-4-yl)carbonyl]-L-norvaline |
| 127 | N-[(3'-Fluoro-4'-{[6-(trifluoromethoxy)-1,3-benzothiazol-2-yl]amino}biphenyl-4-yl)carbonyl]-L-isoleucine |
| 128 | N-[(3'-Fluoro-4'-{[6-(trifluoromethoxy)-1,3-benzothiazol-2-yl]amino}biphenyl-4-yl)carbonyl]-3-methyl-L-valine |
| 129 | 3-Cyclopropyl-N-[(3'-fluoro-4'-{[6-(trifluoromethoxy)-1,3-benzothiazol-2-yl]amino}biphenyl-4-yl)carbonyl]-L-alanine |
| 130 | (2S)-2-{[(3'-Fluoro-4'-{[6-(trifluoromethoxy)-1,3-benzothiazol-2-yl]amino}biphenyl-4-yl)carbonyl]amino}butanoic acid |
| 131 | N-({4'-[(6-Chloro-1,3-benzothiazol-2-yl)amino]-3'-fluorobiphenyl-4-yl}carbonyl)-L-leucine |
| 132 | N-({4'-[(6-Chloro-1,3-benzothiazol-2-yl)amino]biphenyl-4-yl}carbonyl)-L-valine |
| 133 | N-({4'-[(6-Chloro-1,3-benzothiazol-2-yl)amino]biphenyl-4-yl}carbonyl)-L-leucine |
| 134 | N-({4'-[(6-Chloro-1,3-benzothiazol-2-yl)amino]biphenyl-4-yl}carbonyl)-L-norvaline |
| 135 | N-({4'-[(6-Chloro-1,3-benzothiazol-2-yl)amino]biphenyl-4-yl}carbonyl)-L-isoleucine |
| 136 | N-({4'-[(6-Chloro-1,3-benzothiazol-2-yl)amino]biphenyl-4-yl}carbonyl)-3-methyl-L-valine |
| 137 | N-({4'-[(6-Chloro-1,3-benzothiazol-2-yl)amino]-3'-fluorobiphenyl-4-yl}carbonyl)-L-valine |
| 138 | N-({4'-[(6-Chloro-1,3-benzothiazol-2-yl)amino]-3'-fluorobiphenyl-4-yl}carbonyl)-L-norvaline |
| 139 | (2S)-2-[({4'-[(6-Chloro-1,3-benzothiazol-2-yl)amino]-3'-fluorobiphenyl-4-yl}carbonyl)amino]butanoic acid |
| 140 | N-({4'-[(6-Chloro-1,3-benzothiazol-2-yl)amino]biphenyl-4-yl}carbonyl)-3-cyclopropyl-L-alanine |
| 141 | N-({4'-[(6-Chloro-1,3-benzothiazol-2-yl)amino]-3'-fluorobiphenyl-4-yl}carbonyl)-3-methyl-L-valine |
| 142 | (2S)-2-[({4'-[(6-Chloro-1,3-benzothiazol-2-yl)amino]biphenyl-4-yl}carbonyl)amino]butanoic acid |

TABLE 7b-continued

IUPAC Names of Compounds in Table 7a

| Example No. | IUPAC Name |
|---|---|
| 143 | N-{[4'-([1,3]Thiazolo[5,4-b]pyridin-2-ylamino)biphenyl-4-yl]carbonyl}-L-valine trifluoroacetate |
| 144 | N-{[4'-([1,3]Thiazolo[4,5-c]pyridin-2-ylamino)biphenyl-4-yl]carbonyl}-L-valine trifluoroacetate |
| 145 | N-{[4'-([1,3]Thiazolo[4,5-b]pyridin-2-ylamino)biphenyl-4-yl]carbonyl}-L-valine trifluoroacetate |
| 146 | N-[(3'-Fluoro-4'-{[6-(trifluoromethyl)[1,3]thiazolo[4,5-b]pyridin-2-yl]amino}biphenyl-4-yl)carbonyl]-L-valine trifluoroacetate |
| 147 | N-{[3'-Fluoro-4'-([1,3]thiazolo[4,5-c]pyridin-2-ylamino)biphenyl-4-yl]carbonyl}-L-valine trifluoroacetate |
| 148 | N-{[3'-Fluoro-4'-([1,3]thiazolo[4,5-b]pyridin-2-ylamino)biphenyl-4-yl]carbonyl}-L-valine trifluoroacetate |
| 149 | N-({3'-Fluoro-4'-[(6-fluoro-1,3-benzothiazol-2-yl)amino]biphenyl-4-yl}carbonyl)-O-methyl-L-allothreonine |
| 150 | N-({3'-Fluoro-4'-[(6-fluoro-1,3-benzothiazol-2-yl)amino]biphenyl-4-yl}carbonyl)-N-methyl-L-norvaline |
| 151 | 4,4,4-Trifluoro-2-[({3'-fluoro-4'-[(6-fluoro-1,3-benzothiazol-2-yl)amino]biphenyl-4-yl}carbonyl)amino]butanoic acid |
| 152 | N-({3'-Fluoro-4'-[(6-fluoro-1,3-benzothiazol-2-yl)amino]biphenyl-4-yl}carbonyl)-4-methylene-L-norvaline |
| 153 | 3-Cyclobutyl-N-({3'-fluoro-4'-[(6-fluoro-1,3-benzothiazol-2-yl)amino]biphenyl-4-yl}carbonyl)-L-alanine |
| 154 | (2S)-[({3'-Fluoro-4'-[(6-fluoro-1,3-benzothiazol-2-yl)amino]biphenyl-4-yl}carbonyl)amino](phenyl)acetic acid |
| 155 | N-({4'-[(6-Fluoro-1,3-benzothiazol-2-yl)amino]biphenyl-4-yl}carbonyl)-O-methyl-L-allothreonine |
| 156 | N-({4'-[(6-Fluoro-1,3-benzothiazol-2-yl)amino]biphenyl-4-yl}carbonyl)-N-methyl-L-norvaline |
| 157 | 1-[({4'-[(6-Fluoro-1,3-benzothiazol-2-yl)amino]biphenyl-4-yl}carbonyl)(methyl)amino]cyclopropanecarboxylic acid |
| 158 | (4R)-3-({4'-[(6-Fluoro-1,3-benzothiazol-2-yl)amino]biphenyl-4-yl}carbonyl)-5,5-dimethyl-1,3-thiazolidine-4-carboxylic acid |
| 159 | 4,4,4-Trifluoro-2-[({4'-[(6-fluoro-1,3-benzothiazol-2-yl)amino]biphenyl-4-yl}carbonyl)amino]butanoic acid |
| 160 | N-({4'-[(6-Fluoro-1,3-benzothiazol-2-yl)amino]biphenyl-4-yl}carbonyl)-4-methylene-L-norvaline |
| 161 | 3-Cyclobutyl-N-({4'-[(6-fluoro-1,3-benzothiazol-2-yl)amino]biphenyl-4-yl}carbonyl)-L-alanine |
| 162 | (2S)-[({4'-[(6-Fluoro-1,3-benzothiazol-2-yl)amino]biphenyl-4-yl}carbonyl)amino](phenyl)acetic acid |
| 163 | N-[(3'-Fluoro-4'-{[6-(trifluoromethyl)-1,3-benzothiazol-2-yl]amino}biphenyl-4-yl)carbonyl]-L-valine |
| 164 | N-[(3'-Fluoro-4'-{[6-(trifluoromethyl)-1,3-benzothiazol-2-yl]amino}biphenyl-4-yl)carbonyl]-L-leucine |
| 165 | N-[(3'-Fluoro-4'-{[6-(trifluoromethyl)-1,3-benzothiazol-2-yl]amino}biphenyl-4-yl)carbonyl]-L-norvaline |
| 166 | N-[(3'-Fluoro-4'-{[6-(trifluoromethyl)-1,3-benzothiazol-2-yl]amino}biphenyl-4-yl)carbonyl]-3-methyl-L-valine |
| 167 | (2S)-2-{[(3'-Fluoro-4'-{[6-(trifluoromethyl)-1,3-benzothiazol-2-yl]amino}biphenyl-4-yl)carbonyl]amino}butanoic acid |
| 168 | N-[(3'-Fluoro-4'-{[6-(trifluoromethyl)-1,3-benzothiazol-2-yl]amino}biphenyl-4-yl)carbonyl]-L-isoleucine |
| 169 | 3-Cyclopropyl-N-[(3'-fluoro-4'-{[6-(trifluoromethyl)-1,3-benzothiazol-2-yl]amino}biphenyl-4-yl)carbonyl]-L-alanine |
| 170 | N-[(4'-{[6-(Trifluoromethyl)-1,3-benzothiazol-2-yl]amino}biphenyl-4-yl)carbonyl]-L-valine |
| 171 | N-[(4'-{[6-(Trifluoromethyl)-1,3-benzothiazol-2-yl]amino}biphenyl-4-yl)carbonyl]-L-leucine |
| 172 | N-[(4'-{[6-(Trifluoromethyl)-1,3-benzothiazol-2-yl]amino}biphenyl-4-yl)carbonyl]-L-norvaline |
| 173 | 3-Methyl-N-[(4'-{[6-(trifluoromethyl)-1,3-benzothiazol-2-yl]amino}biphenyl-4-yl)carbonyl]-L-valine |
| 174 | (2S)-2-{[(4'-{[6-(Trifluoromethyl)-1,3-benzothiazol-2-yl]amino}biphenyl-4-yl)carbonyl]amino}butanoic acid |
| 175 | N-[(4'-{[6-(Trifluoromethyl)-1,3-benzothiazol-2-yl]amino}biphenyl-4-yl)carbonyl]-L-isoleucine |
| 176 | 3-Cyclopropyl-N-[(4'-{[6-(trifluoromethyl)-1,3-benzothiazol-2-yl]amino}biphenyl-4-yl)carbonyl]-L-alanine |
| 177 | N-({3'-Fluoro-4'-[(6-isopropyl-1,3-benzothiazol-2-yl)amino]biphenyl-4-yl}carbonyl)-L-valine |
| 178 | N-({3'-Fluoro-4'-[(6-isopropyl-1,3-benzothiazol-2-yl)amino]biphenyl-4-yl}carbonyl)-L-leucine |
| 179 | N-({3'-Fluoro-4'-[(6-isopropyl-1,3-benzothiazol-2-yl)amino]biphenyl-4-yl}carbonyl)-L-norvaline |

TABLE 7b-continued

IUPAC Names of Compounds in Table 7a

| Example No. | IUPAC Name |
|---|---|
| 180 | (2S)-2-[({3'-Fluoro-4'-[(6-isopropyl-1,3-benzothiazol-2-yl)amino]biphenyl-4-yl}carbonyl)amino]butanoic acid |
| 181 | N-({3'-Fluoro-4'-[(6-isopropyl-1,3-benzothiazol-2-yl)amino]biphenyl-4-yl}carbonyl)-3-methyl-L-valine |
| 182 | N-({3'-Fluoro-4'-[(6-isopropyl-1,3-benzothiazol-2-yl)amino]biphenyl-4-yl}carbonyl)-L-isoleucine |
| 183 | 3-Cyclopropyl-N-({3'-fluoro-4'-[(6-isopropyl-1,3-benzothiazol-2-yl)amino]biphenyl-4-yl}carbonyl)-L-alanine |
| 184 | N-[(4'-{[6-(Trifluoromethyl)[1,3]thiazolo[4,5-b]pyridin-2-yl]amino}biphenyl-4-yl)carbonyl]-L-leucine trifluoroacetate |
| 185 | N-[(4'-{[6-(Trifluoromethyl)[1,3]thiazolo[4,5-b]pyridin-2-yl]amino}biphenyl-4-yl)carbonyl]-L-norvaline trifluoroacetate |
| 186 | 3-Methyl-N-[(4'-{[6-(trifluoromethyl)[1,3]thiazolo[4,5-b]pyridin-2-yl]amino}biphenyl-4-yl)carbonyl]-L-valine trifluoroacetate |
| 187 | (2S)-2-{[(4'-{[6-(Trifluoromethyl)[1,3]thiazolo[4,5-b]pyridin-2-yl]amino}biphenyl-4-yl)carbonyl]amino}butanoic acid trifluoroacetate |
| 188 | N-[(4'-{[6-(Trifluoromethyl)[1,3]thiazolo[4,5-b]pyridin-2-yl]amino}biphenyl-4-yl)carbonyl]-L-isoleucine trifluoroacetate |
| 189 | 3-Cyclopropyl-N-[(4'-{[6-(trifluoromethyl)[1,3]thiazolo[4,5-b]pyridin-2-yl]amino}biphenyl-4-yl)carbonyl]-L-alanine trifluoroacetate |
| 190 | N-[(3'-Fluoro-4'-{[6-(trifluoromethyl)[1,3]thiazolo[4,5-b]pyridin-2-yl]amino}biphenyl-4-yl)carbonyl]-L-leucine trifluoroacetate |
| 191 | N-[(3'-Fluoro-4'-{[6-(trifluoromethyl)[1,3]thiazolo[4,5-b]pyridin-2-yl]amino}biphenyl-4-yl)carbonyl]-L-norvaline trifluoroacetate |
| 192 | N-[(3'-Fluoro-4'-{[6-(trifluoromethyl)[1,3]thiazolo[4,5-b]pyridin-2-yl]amino}biphenyl-4-yl)carbonyl]-3-methyl-L-valine trifluoroacetate |
| 193 | (2S)-2-{[(3'-Fluoro-4'-{[6-(trifluoromethyl)[1,3]thiazolo[4,5-b]pyridin-2-yl]amino}biphenyl-4-yl)carbonyl]amino}butanoic acid trifluoroacetate |
| 194 | N-[(3'-Fluoro-4'-{[6-(trifluoromethyl)[1,3]thiazolo[4,5-b]pyridin-2-yl]amino}biphenyl-4-yl)carbonyl]-L-isoleucine trifluoroacetate |
| 195 | N-({4'-[(7-Chloro[1,3]thiazolo[5,4-c]pyridin-2-yl)amino]-3'-fluorobiphenyl-4-yl}carbonyl)-L-valine trifluoroacetate |

Methods of Use

As used herein, various terms are defined below.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "subject" as used herein includes mammals (e.g., humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The term "combination therapy" or "co-therapy" means the administration of two or more therapeutic agents to treat a disease, condition, and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The phrase "therapeutically effective" means the amount of each agent administered that will achieve the goal of improvement in a disease, condition, and/or disorder severity, while avoiding or minimizing adverse side effects associated with the given therapeutic treatment.

The term "pharmaceutically acceptable" means that the subject item is appropriate for use in a pharmaceutical product.

The compounds of Formula (I) of this invention are expected to be valuable as therapeutic agents. Accordingly, an embodiment of this invention includes a method of treating the various conditions in a patient (including mammals) which comprises administering to said patient a composition containing an amount of the compound of Formula (I) that is effective in treating the target condition.

This invention relates to compounds that may be useful for the regulation of food intake (e.g., stimulation and suppression). For example, an object of this invention is to provide methods for treating obesity and inducing weight loss in an individual by administration of a compound of the invention. The method of the invention comprises administering to an individual a therapeutically effective amount of at least one compound of the invention, or a prodrug thereof, which is sufficient to induce weight loss. The invention further comprises a method of preventing weight gain in an individual by administering an amount of at least one compound of the invention, or a prodrug thereof, which is sufficient to prevent weight gain.

The present invention also relates to the use of the compounds of this invention for the treatment of obesity-related diseases including associated dyslipidemia and other obesity- and overweight-related complications such as, for example, cholesterol gallstones, gallbladder disease, gout, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, Syndrome X, type 2 diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease such as stroke, and peripheral vessel disease. The compounds of this invention may also be useful for treating physiological disorders related to, for example, regulation of insulin sensitivity, inflammatory response, plasma triglycerides, HDL, LDL and cholesterol levels and the like.

Compounds of Formula (I) may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

Where separate dosage formulations are used, a compound of Formula (I) and one or more additional therapeutic agents may be administered at essentially the same time (e.g., concurrently) or at separately staggered times (e.g., sequentially).

For example, a compound of Formula (I) may be used in combination with other therapies and drugs useful for the treatment of obesity. For example, anti-obesity drugs include β-3 adrenergic receptor agonists such as CL 316,243; cannabinoid (e.g., CB-1) antagonists such as Rimonabant; neuropeptide-Y receptor antagonists; neuropeptide Y5 inhibitors; apo-B/MTP inhibitors; 11β-hydroxy steroid dehydrogenase-1 inhibitors; peptide $YY_{3-36}$ or analogs thereof; MCR4 agonists; CCK-A agonists; monoamine reuptake inhibitors; sympathomimetic agents; dopamine agonists; melanocyte-stimulating hormone receptor analogs; melanin concentrating hormone antagonists; leptin; leptin analogs; leptin receptor agonists; galanin antagonists; lipase inhibitors; bombesin agonists; thyromimetic agents; dehydroepiandrosterone or analogs thereof; glucocorticoid receptor antagonists; orexin receptor antagonists; ciliary neurotrophic factor; ghrelin receptor antagonists; histamine-3 receptor antagonists; neuromedin U receptor agonists; appetite suppressants, such as, for example, sibutramine (Meridia); and lipase inhibitors, such as, for example, orlistat (Xenical). The compounds of the present invention may also be administered in combination with a drug compound that modulates digestion and/or metabolism such as drugs that modulate thermogenesis, lipolysis, gut motility, fat absorption, and satiety.

In addition, a compound of Formula (J) may be administered in combination with one or more of the following agents for the treatment of diabetes or diabetes-related disorders including PPAR ligands (agonists, antagonists), insulin secretagogues, for example, sulfonylurea drugs and non-sulfonylurea secretagogues, α-glucosidase inhibitors, insulin sensitizers, hepatic glucose output lowering compounds, and insulin and insulin derivatives. Such therapies may be administered prior to, concurrently with, or following administration of the compounds of the invention. Insulin and insulin derivatives include both long and short acting forms and formulations of insulin. PPAR ligands may include agonists and/or antagonists of any of the PPAR receptors or combinations thereof. For example, PPAR ligands may include ligands of PPAR-α, PPAR-γ, PPAR-δ or any combination of two or three of the receptors of PPAR. PPAR ligands include, for example, rosiglitazone, troglitazone, and pioglitazone.

Sulfonylurea drugs include, for example, glyburide, glimepiride, chlorpropamide, tolbutamide, and glipizide. α-glucosidase inhibitors that may be useful in treating diabetes when administered with a compound of the invention include acarbose, miglitol, and voglibose. Insulin sensitizers that may be useful in treating diabetes include PPAR-γ agonists such as the glitazones (e.g., troglitazone, pioglitazone, englitazone, MCC-555, rosiglitazone, and the like) and other thiazolidinedione and non-thiazolidinedione compounds; biguanides such as metformin and phenformin; protein tyrosine phosphatase-1B (PTP-1B) inhibitors; dipeptidyl peptidase IV (DPP-IV) inhibitors, and 11beta-HSD inhibitors. Hepatic glucose output lowering compounds that may be useful in treating diabetes when administered with a compound of the invention include glucagon anatgonists and metformin, such as Glucophage and Glucophage XR. Insulin secretagogues that may be useful in treating diabetes when administered with a compound of the invention include sulfonylurea and non-sulfonylurea drugs: GLP-1, GIP, PACAP, secretin, and derivatives thereof; nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin.

Compounds of the invention may also be used in methods of the invention in combination with drugs commonly used to treat lipid disorders in patients. Such drugs include, but are not limited to, HM4G-CoA reductase inhibitors, nicotinic acid, fatty acid lowering compounds (e.g., acipimox); lipid lowering drugs (e.g., stanol esters, sterol glycosides such as tiqueside, and azetidinones such as ezetimibe), ACAT inhibitors (such as avasimibe), bile acid sequestrants, bile acid reuptake inhibitors, microsomal triglyceride transport inhibitors, and fibric acid derivatives. HMG-CoA reductase inhibitors include, for example, lovastatin, simvastatin, pravastatin, fluvastatin, atorvastatin, rivastatin, itavastatin, cerivastatin, and ZD-4522. Fibric acid derivatives include, for example, clofibrate, fenofibrate, bezafibrate, ciprofibrate, beclofibrate, etofibrate, and gemfibrozil. Sequestrants include, for example, cholestyramine, colestipol, and dialkylaminoalkyl derivatives of a cross-linked dextran.

Compounds of the invention may also be used in combination with anti-hypertensive drugs, such as, for example, β-blockers and ACE inhibitors. Examples of additional anti-hypertensive agents for use in combination with the compounds of the present invention include calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, neutral endopeptidase (NEP) inhibitors, vasopepsidase inhibitors (dual NEP-ACE inhibitors) (e.g., omapatrilat and gemopatrilat), and nitrates.

The compound of Formula (I) may also be utilized, in free base form or in compositions, as well as in research and diagnostics or as analytical reference standards, and the like, which are well known in the art. Therefore, the present invention includes compositions which are comprised of an inert carrier and an effective amount of a compound of Formula (I), or a salt, or ester thereof. An inert carrier is any material which does not interact with the compound to be carried and which lends support, means of conveyance, bulk, traceable material, and the like to the compound to be carried. An effective amount of the compound is that amount which produces a result or exerts an influence on the particular procedure being performed.

It is anticipated that prodrug forms of the compounds of this invention will prove useful in certain circumstances, and such compounds are also intended to fall within the scope of the invention. Prodrug forms may have advantages over the parent compounds exemplified herein, in that they are better absorbed, better distributed, more readily penetrate the central nervous system, are more slowly metabolized or cleared, etc. Prodrug forms may also have formulation advantages in terms of crystallinity or water solubility. For example, compounds of the invention having one or more hydroxyl groups may be converted to esters or carbonates bearing one or more carboxyl, hydroxyl or amino groups, which are hydrolyzed at physiological pH values or are cleaved by endogenous esterases or lipases in vivo (see, e.g., U.S. Pat. Nos. 4,942,184; 4,960,790; 5,817,840; and 5,824,701, all of which are incorporated herein by reference in their entirety, and references therein).

Pharmaceutical Compositions

Based on the above tests, or other well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range, for example, from about 0.001 mg/kg to about 200 mg/kg. A unit dosage may contain from, for example, about 0.05 mg to about 1500 mg of active ingredient, and may be administered one or more times per day. The daily dosage for administration by injection, including intravenous, intramuscular, subcutaneous, and parenteral injections, and use of infusion techniques may be from, for example, about 0.01 to about 200 mg/kg. The daily rectal dosage regimen may be from, for example, 0.01 to 200 mg/kg of total body weight. The transdermal concentration may be that required to maintain a daily dose of from, for example, 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention or a pharmaceutically acceptable salt thereof may be ascertained by those skilled in the art using conventional treatment tests.

The compounds of this invention may be utilized to achieve the desired pharmacological effect by administration to a subject in need thereof in an appropriately formulated pharmaceutical composition. A subject, for example, may be a mammal, including a human, in need of treatment for a particular condition or disease. Therefore, the present invention includes pharmaceutical compositions which are comprised of a pharmaceutically acceptable carrier and a pharmaceutically effective amount of a compound identified by the methods described herein, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound is that amount which produces a result or exerts an influence on the particular condition being treated. The compounds identified by the methods described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol; glycols; glycerol ketals; ethers; an oil; a fatty acid; a fatty acid ester or glyceride; or an acetylated fatty acid glyceride with or without the addition of a pharmaceutically acceptable surfactant; suspending agent; or emulsifying agent and other pharmaceutical adjuvants.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

The pharmaceutical compositions may be in the form of sterile injectable aqueous suspensions. Such suspensions may be formulated according to known methods using suitable dispersing or wetting agents and suspending agents, dispersing or wetting agents which may be a naturally occurring phosphatide, a condensation product of an alkylene oxide with a fatty acid, a condensation product of ethylene oxide with a long chain aliphatic alcohol, a condensation product of ethylene oxide with a partial ester derived form a fatty acid and a hexitol, or a condensation product of an ethylene oxide with a partial ester derived from a fatty acid and a hexitol anhydride.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

Another formulation employs the use of biodegradable microspheres that allow controlled, sustained release. Such formulations can be comprised of synthetic polymers or copolymers. Such formulations allow for injection, inhalation, nasal or oral administration. The construction and use of biodegradable microspheres for the delivery of pharmaceutical agents is well known in the art (e.g., U.S. Pat. No. 6,706,289, incorporated herein by reference).

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

The compounds identified by the methods described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds identified by the methods described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20' edition, 2000)

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Biological Activity of the Compounds

In order that this invention may be better understood, the following examples are set forth. These examples are for the purpose of illustration only, and are not to be construed as limiting the scope of the invention in any manner. All publications mentioned herein are incorporated by reference in their entirety.

Demonstration of the activity of the compounds of the present invention may be accomplished through in vitro, ex vivo, and in vivo assays that are well known in the art. For example, to demonstrate the efficacy of a pharmaceutical agent for the treatment of obesity and related disorders, the following assays may be used.

Evaluation of Compound Effect on the Inhibition of DGAT-1 Enzyme Activity

The human DGAT-1 gene (see, e.g., U.S. Pat. No. 6,100,077) was isolated from a human cDNA library by PCR. Recombinant AcNPV baculovirus was constructed in which the gene for occlusion body forming protein polyhedrin was replaced with the DGAT-1 gene. The DGAT-1 gene sequence was inserted into the AcNPV genome 3' to the polyhedrin promoter sequence placing DGAT-1 under the transcriptional control of the polyhedrin promoter. Spodoptera frugiperda-derived Sf9 insect cells were infected with DGAT-1-containing recombinant baculovirus at the multiplicity of infection of 5 and harvested 48 h post-infection. DGAT-1-expressing insect cells were homogenized in 10 mM Tris, 250 mM sucrose, pH 7.5 at the concentration of 100 mg of wet cell biomass per mL. The homogenate was centrifuged at 25,000 g for 30 min. The 25,000 g pellet was discarded and the supernatant was centrifuged at 100,000 g for 1 h. The 100,000 g supernatant was discarded and the 100,000 g DGAT-1-containing membrane pellet was re-suspended in 10 mM Tris, 50% (v/v) glycerol pH 7.5.

DGAT-1 enzyme activity was determined by a phase partitioning protocol. Specifically, DGAT-1 containing membranes were incubated in 20 mM didecanoyl glycerol, 5 mM $^{14}$C-decanoyl-CoA, 2 mM $MgCl_2$, 0.01% BSA, 50 mM HEPES, pH 7.5 buffer in the presence of varying concentrations of inhibitors. Assays were performed in 100 μL volumes in 96-well microtiter plates with 0.5 μg of total membrane protein per well. The assay was initiated by substrate and mixed gently for 1 h at ambient temperature. Activity was quenched by the addition of 25 μL of 0.1% phosphoric acid solution. Selective extraction of the hydrophobic tridecanoylglycerol product was accomplished by the addition of 150 μL phase partitioning scintillation fluid Microscint® (Packard, Inc.) and vigorous mixing for 30 min. Quantification of the product was accomplished by a MicroBeta® scintillation counter (Wallac, Inc.) after settling for approximately 16 h at ambient temperatures.

Evaluation of Compound Effect on the Inhibition of Cellular Triglyceride Deposition The cell-based assay for DGAT-1 was conducted with human colorectal adenocarcinoma cells HT-29 (HTB-38, ATCC). HT-29 cells were grown in 75 cm$^2$ plate until ~90% confluent in DMEM media with 10% FBS, PSF, glutamine, and 10 mM acetate. Cells were then re-plated in 24-well plates to give 1:1.2 dilution and grown approximately 16 h. Triacylglyceride formation was stimulated by the addition of lauric acid to 0.01% final concentration in the presence of varying concentrations of inhibitors. After 6 h, cells were released from the plate by trypsin, collected by centrifugation, re-suspended in water, transferred to glass HPLC, frozen at –70° C., and lyophilized. Freeze dried cell pellets were re-suspended in 150 μL HPLC grade tetrohydrofuran and sealed in the vials. Vials were sonnicated for 30 min with heating in a sonicating water bath (Fisher, Inc.). Cellular triacylglycerides were quantified by HPLC (HP1100, Agilent, Inc.) utilizing evaporative light-scattering detection (PL-ELS 1000, Polymer Labs, Inc.). Chromatographic separation was accomplished by 30 to 100% B buffer in 4 min followed by 3 min at 100% B buffer using a PLRP S 100 column (5 micron, 150×4.6 mm, Polymer Labs, Inc.) at 50° C. (A: 50% acetonitrile, 2.5% methanol, B: 100% tetrohydrofuran). Sample injections were 20 μL and the detector was set at 0.4 SLM, 40° C. nebulizer, and 80° C. evaporator. Non-polar fatty acids and glycerol lipids were identified and quantified by using commercially available standards.

Evaluation of Compound Efficacy on the Reduction of Body Weight in Diet-Induced Obese Mice.

The purpose of this protocol is to determine the effect of chronic administration of a compound on the body weight of mice made obese by exposure to a 45% kcal/g high fat diet for more than 10 weeks. The body weight of mice selected for these studies was higher than three standard deviations from the weight of a control group of mice fed standard low fat (5-6% fat) mouse chow. Diet-induced obese (DIO) animals have been used frequently in the determination of compound efficacy in the reduction of body weight (see, e.g., Brown, et al., Brit. J. Pharmacol. 132:1898-1904, 2001; Guerre-Millo, et al., J. Biol. Chem. 275(22):16638-42, 2000; Han, et al., Intl. J. Obesity and Related Metabolic Disorders 23(2): 174-79, 1999; Surwit, et al., Endocrinol. 141(10):3630-37, 2000).

This animal model has been successfully used in the identification and characterization of the efficacy profile of compounds that are or have been used in the management of body weight in obese humans (see, e.g., Brown, et al., 2001; Guerre-Millo, et al., 2000; Han, et al., 1999).

A typical study included 60-80 male C57b1/J6 mice (n=10/treatment group) with an average body weight of approximately 45 g. Mice are kept in standard animal rooms under controlled temperature and humidity and a 12 hour/12 hour light/dark cycle. Water and food are continuously available. Mice were individually housed. Animals are sham dosed with study vehicle for at least four days before the recording of two-day baseline measurements of body weight and 24-hour food and water consumption. Mice are assigned to one of 6-8 treatment groups based upon their body weight on baseline. The groups are set up so that the mean and standard error of the mean of body weight were similar.

Animals are orally gavaged (5 mL/kg) daily before the dark phase of the light/dark cycle for a pre-determined number of days (typically 8-14 days) with their assigned dose/compound. Body weight, and food and water consumption are measured. Data is analyzed using appropriate statistics following the research design. On the final day, animals are euthanized using $CO_2$ inhalation.

Compounds are typically dosed at 1 to 30 mg/kg p.o. q.d., and compounds are considered to be active if a statistically significant reduction in weight was observed for the treated animals, relative to vehicle-treated control animals.

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

The invention claimed is:
1. A compound of Formula (I)

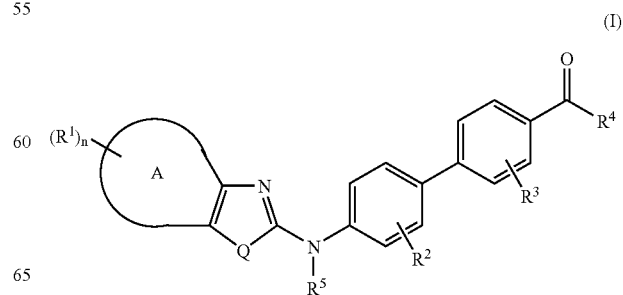

wherein
Q is O, NR$^{11}$, or S;

is a fused ring selected from
an aromatic 6-membered ring containing 0 or 1 N atoms;
R$^1$ is independently selected from
halo, (C$_1$-C$_6$)alkyl, (C$_1$-C$_6$)alkoxy, nitro, cyano, (C$_1$-C$_6$)haloalkyl, (C$_1$-C$_6$)haloalkoxy, aminocarbonyl, (C$_1$-C$_6$)alkylaminocarbonyl, bis[(C$_1$-C$_6$)alkyl]aminocarbonyl, aminosulfonyl, (C$_1$-C$_6$)alkylaminosulfonyl, bis[(C$_1$-C$_6$)alkyl]aminosulfonyl, (C$_1$-C$_6$)alkylcarbonylamino, (C$_1$-C$_6$)alkylsulfonyl, (C$_1$-C$_6$)alkylsulfonylamino, hydroxy-(C$_2$-C$_6$)alkylaminocarbonyl, 1-morpholinylcarbonyl, and 1-piperidinylcarbonyl, and
when two of said R$^1$ substituents are (C$_1$-C$_6$)alkyl and are attached to adjacent carbon atoms of the Ring A, they may be joined together to form a 5-7-membered carbocyclic ring;
n is 0, 1, or 2;
R$^2$ and R$^3$ are independently selected from hydrogen, halo, hydroxy, (C$_1$-C$_6$)alkyl, trifluoromethyl, (C$_1$-C$_6$)alkoxy, and trifluoromethoxy;
R$^4$ is selected from

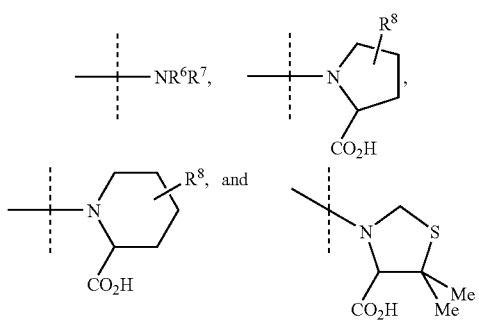

wherein
R$^6$ is H or CH$_3$;
and
R$^7$

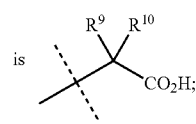

wherein
R$^9$ is selected from
(C$_1$-C$_6$)alkyl optionally substituted with one or two groups selected from vinyl, CF$_3$, OH, methoxy, SCH$_3$, NH$_2$, —CO$_2$H, and —CONH$_2$,
(CH$_2$)$_m$phenyl wherein m is 0 to 3, and
where the phenyl ring is optionally substituted with one or two groups selected from halo, (C$_1$-C$_6$)alkyl, (C$_1$-C$_6$)alkoxy, OH, nitro, and cyano,
piperidinyl optionally substituted on C with halo and optionally substituted on C or N with (C$_1$-C$_6$)alkyl, (C$_1$-C$_6$)alkoxy, nitro, or cyano, tetrahydropyran-4-yl;
R$^{10}$ is H or methyl;
or
R$^9$ and R$^{10}$ may form, together with the carbon to which they are attached, a 3- to 6-membered carbocyclic ring,
R$^8$ is hydrogen, (C$_1$-C$_4$)alkyl, hydroxy, or methoxy;
R$^5$ is selected from H, (C$_1$-C$_6$)alkyl, and hydroxy-(C$_2$-C$_6$)alkyl;
R$^{11}$ is selected from H, (C$_1$-C$_6$)alkyl, and hydroxy-(C$_2$-C$_6$)alkyl;
and the pharmaceutically acceptable salts and esters thereof.

2. The compound of claim 1, wherein
Q is O, NR$^{11}$, or S;

is a fused ring selected from
an aromatic 6-membered ring containing 0 or 1 N atoms;
R$^1$ is independently selected from
halo, (C$_1$-C$_6$)alkyl, (C$_1$-C$_6$)alkoxy, nitro, cyano, (C$_1$-C$_6$)haloalkyl, (C$_1$-C$_6$)haloalkoxy, aminocarbonyl, (C$_1$-C$_6$)alkylaminocarbonyl, bis[(C$_1$-C$_6$)alkyl]aminocarbonyl, aminosulfonyl, (C$_1$-C$_6$)alkylaminosulfonyl, bis[(C$_1$-C$_6$)alkyl]aminosulfonyl, (C$_1$-C$_6$)alkylcarbonylamino, (C$_1$-C$_6$)alkylsulfonyl, (C$_1$-C$_6$)alkylsulfonylamino, hydroxy-(C$_2$-C$_6$)alkylaminocarbonyl, 1-morpholinylcarbonyl, and 1-piperidinylcarbonyl;
n is 0, 1, or 2;
R$^2$ and R$^3$ are independently selected from hydrogen, halo, hydroxy, (C$_1$-C$_6$)alkyl, trifluoromethyl, (C$_1$-C$_6$)alkoxy, and trifluoromethoxy;
R$^4$ is selected from

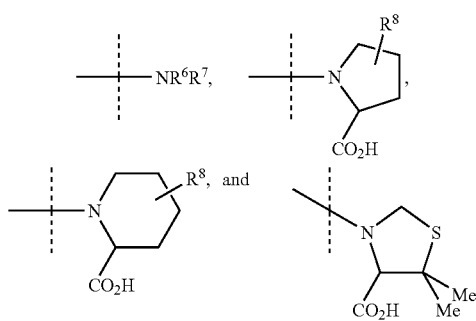

wherein
R$^6$ is H or CH$_3$;
and
R$^7$

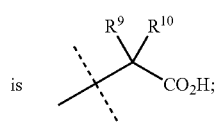

wherein
R$^9$ is selected from
(C$_1$-C$_6$)alkyl optionally substituted with one or two groups selected from vinyl, CF$_3$, OH, methoxy, SCH$_3$, NH$_2$, —CO$_2$H, and —CONH$_2$,
(CH$_2$)$_m$phenyl wherein m is 0 to 3, and
where the phenyl ring is optionally substituted with one or two groups selected from halo, (C$_1$-C$_6$)alkyl, (C$_1$-C$_6$)alkoxy, OH, nitro, and cyano,
piperidinyl optionally substituted on C with halo and optionally substituted on C or N with (C$_1$-C$_6$)alkyl, (C$_1$-C$_6$)alkoxy, nitro, or cyano,
tetrahydropyran-4-yl;
R$^{10}$ is H or methyl;
or
R$^9$ and R$^{10}$ may form, together with the carbon to which they are attached, a 3- to 6-membered carbocyclic ring,
R$^8$ is hydrogen, (C$_1$-C$_4$)alkyl, hydroxy, or methoxy;
R$^5$ is selected from H, (C$_1$-C$_6$)alkyl, and hydroxy-(C$_2$-C$_6$)alkyl; and
R$^{11}$ is selected from H, (C$_1$-C$_6$)alkyl, and hydroxy-(C$_2$-C$_6$)alkyl.

3. The compound of claim 1, wherein
Q is O, NR$^{11}$, or S;

is a fused ring selected from
an aromatic 6-membered ring containing 0 or 1 N atoms;
R$^1$ is independently selected from
halo, (C$_1$-C$_6$)alkyl, (C$_1$-C$_6$)alkoxy, nitro, cyano, (C$_1$-C$_6$)haloalkyl, (C$_1$-C$_6$)haloalkoxy, aminocarbonyl, (C$_1$-C$_6$)alkylaminocarbonyl, bis[(C$_1$-C$_6$)alkyl]aminocarbonyl, aminosulfonyl, (C$_1$-C$_6$)alkylaminosulfonyl, bis[(C$_1$-C$_6$)alkyl]aminosulfonyl, (C$_1$-C$_6$)alkylcarbonylamino, (C$_1$-C$_6$)alkylsulfonyl, (C$_1$-C$_6$)alkylsulfonylamino, hydroxy-(C$_2$-C$_6$)alkylaminocarbonyl, 1-morpholinylcarbonyl, and 1-piperidinylcarbonyl;
n is 0, 1, or 2;
R$^2$ and R$^3$ are independently selected from hydrogen, halo, hydroxy, (C$_1$-C$_6$)alkyl, trifluoromethyl, (C$_1$-C$_6$)alkoxy, and trifluoromethoxy;
R$^4$ is selected from

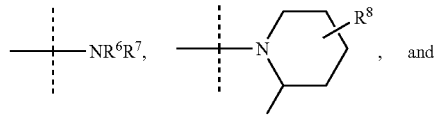

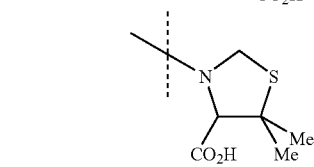

wherein
R$^6$ is H or CH$_3$;
and
R$^7$

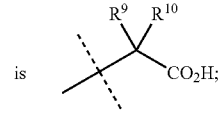

wherein
R$^9$ is selected from
(C$_1$-C$_6$)alkyl optionally substituted with one or two groups selected from vinyl, CF$_3$, OH, methoxy, SCH$_3$, NH$_2$, —CO$_2$H, and —CONH$_2$,
(CH$_2$)$_m$phenyl wherein m is 0 to 3, and
where the phenyl ring is optionally substituted with one or two groups selected from halo, (C$_1$-C$_6$)alkyl, (C$_1$-C$_6$)alkoxy, OH, nitro, and cyano,
piperidinyl optionally substituted on C with halo and optionally substituted on C or N with (C$_1$-C$_6$)alkyl, (C$_1$-C$_6$)alkoxy, nitro, or cyano,
tetrahydropyran-4-yl;
R$^{10}$ is H or methyl;
or
R$^9$ and R$^{10}$ may form, together with the carbon to which they are attached, a 3- to 6-membered carbocyclic ring,
R$^8$ is hydrogen, (C$_1$-C$_4$)alkyl, hydroxy, or methoxy;
R$^5$ is selected from H, (C$_1$-C$_6$)alkyl, and hydroxy-(C$_2$-C$_6$)alkyl; and
R$^{11}$ is selected from H, (C$_1$-C$_6$)alkyl, and hydroxy-(C$_2$-C$_6$)alkyl.

4. The compound of claim 1, wherein
Q is S;

is a fused ring selected from
an aromatic 6-membered ring containing 0 or 1 N atoms;
R$^1$ is independently selected from
halo, (C$_1$-C$_6$)alkyl, (C$_1$-C$_6$)alkoxy, nitro, cyano, (C$_1$-C$_6$)haloalkyl, (C$_1$-C$_6$)haloalkoxy, aminocarbonyl, (C$_1$-C$_6$)alkylaminocarbonyl, bis[(C$_1$-C$_6$)alkyl]aminocarbonyl, aminosulfonyl, (C$_1$-C$_6$)alkylaminosulfonyl, bis[(C$_1$-C$_6$)alkyl]aminosulfonyl, (C$_1$-C$_6$)alkylcarbonylamino, (C$_1$-C$_6$)alkylsulfonyl, (C$_1$-C$_6$)alkylsulfonylamino, hydroxy-(C$_2$-C$_6$)alkylaminocarbonyl, 1-morpholinylcarbonyl, and 1-piperidinylcarbonyl;
n is 0, 1, or 2;
R$^2$ and R$^3$ are independently selected from hydrogen, halo, hydroxy, (C$_1$-C$_6$)alkyl, trifluoromethyl, (C$_1$-C$_6$)alkoxy, and trifluoromethoxy;
R$^4$ is

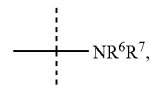

wherein
R$^6$ is H or CH$_3$;
and
R$^7$

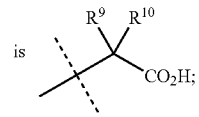

wherein
R⁹ is selected from
(C₁-C₆)alkyl optionally substituted with one or two groups selected from vinyl, CF₃, OH, methoxy, SCH₃, NH₂, —CO₂H, and —CONH₂,
(CH₂)ₘphenyl wherein m is 0 to 3, and
where the phenyl ring is optionally substituted with one or two groups selected from halo, (C₁-C₆)alkyl, (C₃-C₆)alkoxy, OH, nitro, and cyano,
piperidinyl optionally substituted on C with halo and optionally substituted on C or N with (C₁-C₆)alkyl, (C₁-C₆)alkoxy, nitro, or cyano,
tetrahydropyran-4-yl;
R¹⁰ is H or methyl;
Or
R⁹ and R¹⁰ may form, together with the carbon to which they are attached, a 3- to 6-membered carbocyclic ring,
R⁸ is hydrogen, (C₁-C₄)alkyl, hydroxy, or methoxy;
R⁵ is selected from H, (C₁-C₆)alkyl, and hydroxy-(C₂-C₆)alkyl; and
R¹¹ is selected from H, (C₁-C₆)alkyl, and hydroxy-(C₂-C₆)alkyl.

5. The compound of claim 1 selected from
N-({3'-fluoro-4'-[(6-fluoro-1,3-benzothiazol-2-yl)amino]biphenyl-4-yl}carbonyl)-L-valine,
N-({4'-[(6-fluoro-1,3-benzothiazol-2-yl)amino]biphenyl-4-yl}carbonyl)-L-alanine,
N-({3'-fluoro-4'-[(6-fluoro-1,3-benzothiazol-2-yl)amino]biphenyl-4-yl}carbonyl)-L-alanine,
N-({4'-[(6-fluoro-1,3-benzothiazol-2-yl)amino]biphenyl-4-yl}carbonyl)-L-valine,
N-({3-chloro-4'-[(6-fluoro-1,3-benzothiazol-2-yl)amino]biphenyl-4-yl}carbonyl)-L-valine,
N-({3'-fluoro-4'-[(6-fluoro-1,3-benzothiazol-2-yl)amino]-3-methylbiphenyl-4-yl}carbonyl)-L-valine,
N-({3'-fluoro-4'-[(6-fluoro-1,3-benzothiazol-2-yl)amino]-3-methoxybiphenyl-4-yl}carbonyl)-L-valine,
N-({4'-[(6-fluoro-1,3-benzothiazol-2-yl)amino]biphenyl-4-yl}carbonyl)-L-leucine,
N-({3'-fluoro-4'-[(6-fluoro-1,3-benzothiazol-2-yl)amino]biphenyl-4-yl}carbonyl)-L-leucine,
N-({4'-[(6-fluoro-1,3-benzothiazol-2-yl)amino]-3-methoxybiphenyl-4-yl}carbonyl)-L-leucine,
N-({3'-fluoro-4'-[(6-fluoro-1,3-benzothiazol-2-yl)amino]-3-methoxybiphenyl-4-yl}carbonyl)-L-leucine,
N-({3-chloro-4'-[(6-fluoro-1,3-benzothiazol-2-yl)amino]biphenyl-4-yl}carbonyl)-L-leucine,
N-({4'-[(6-fluoro-1,3-benzothiazol-2-yl)amino]-3-methylbiphenyl-4-yl}carbonyl)-L-leucine,
N-({3'-fluoro-4'-[(6-fluoro-1,3-benzothiazol-2-yl)amino]-3-methylbiphenyl-4-yl}carbonyl)-L-leucine,
N-({4'-[(6-fluoro-1,3-benzothiazol-2-yl)amino]biphenyl-4-yl}carbonyl)-D-leucine,
N-({3'-fluoro-4'-[(6-fluoro-1,3-benzothiazol-2-yl)amino]biphenyl-4-yl}carbonyl)-D-leucine,
N-({4'-[(6-fluoro-1,3-benzothiazol-2-yl)amino]biphenyl-4-yl}carbonyl)-L-isoleucine,
N-({3'-fluoro-4'-[(6-fluoro-1,3-benzothiazol-2-yl)amino]biphenyl-4-yl}carbonyl)-L-isoleucine,
N-([3'-fluoro-4'-[(6-fluoro-1,3-benzothiazol-2-yl)amino]-3-methoxybiphenyl-4-yl}carbonyl)-L-isoleucine,
N-({4'-[(6-fluoro-1,3-benzothiazol-2-yl)amino]biphenyl-4-yl}carbonyl)-L-phenylalanine,
N-({3'-fluoro-4'-[(6-fluoro-1,3-benzothiazol-2-yl)amino]biphenyl-4-yl}carbonyl)-L-phenylalanine,
N-({4'-[(6-fluoro-1,3-benzothiazol-2-yl)amino]-3-methoxybiphenyl-4-yl}carbonyl)-L-phenylalanine,
N-({4'-[(6-fluoro-1,3-benzothiazol-2-yl)amino]-3-methylbiphenyl-4-yl}carbonyl)-L-phenylalanine,
N-({3'-fluoro-4'-[(6-fluoro-1,3-benzothiazol-2-yl)amino]-3-methylbiphenyl-4-yl}carbonyl)-L-phenylalanine,
N-({3-chloro-4'-[(6-fluoro-1,3-benzothiazol-2-yl)amino]biphenyl-4-yl}carbonyl)-L-phenylalanine,
1-({4'-[(6-fluoro-1,3-benzothiazol-2-yl)amino]biphenyl-4-yl}carbonyl)-L-proline,
1-({3'-fluoro-4'-[(6-fluoro-1,3-benzothiazol-2-yl)amino]biphenyl-4-yl}carbonyl)-L-proline,
1-({4'-[(6-fluoro-1,3-benzothiazol-2-yl)amino]-3-methoxybiphenyl-4-yl}carbonyl)-L-proline,
1-({3-chloro-4'-[(6-fluoro-1,3-benzothiazol-2-yl)amino]biphenyl-4-yl}carbonyl)-L-proline,
1-({4'-[(6-fluoro-1,3-benzothiazol-2-yl)amino]-3-methylbiphenyl-4-yl}carbonyl)-L-proline,
1-({3'-fluoro-4'-[(6-fluoro-1,3-benzothiazol-2-yl)amino]-3-methylbiphenyl-4-yl}carbonyl)-L-proline,
N-({4'-[(6-fluoro-1,3-benzothiazol-2-yl)amino]biphenyl-4-yl}carbonyl)-2-methylalanine,
N-({3'-fluoro-4'-[(6-fluoro-1,3-benzothiazol-2-yl)amino]biphenyl-4-yl}carbonyl)-2-methylalanine,
N-({4'-[(6-fluoro-1,3-benzothiazol-2-yl)amino]-3-methoxybiphenyl-4-yl}carbonyl)-2-methylalanine,
N-({3-chloro-4'-[(6-fluoro-1,3-benzothiazol-2-yl)amino]biphenyl-4-yl}carbonyl)-2-methylalanine,
N-({4'-[(6-fluoro-1,3-benzothiazol-2-yl)amino]-3-methylbiphenyl-4-yl}carbonyl)-2-methylalanine,
N-({3'-fluoro-4'-[(6-fluoro-1,3-benzothiazol-2-yl)amino]-3-methylbiphenyl-4-yl}carbonyl)-2-methylalanine,
1-[({4'-[(6-fluoro-1,3-benzothiazol-2-yl)amino]biphenyl-4-yl}carbonyl)amino]cyclopropanecarboxylic acid,
1-[({3'-fluoro-4'-[(6-fluoro-1,3-benzothiazol-2-yl)amino]biphenyl-4-yl}carbonyl)amino]cyclopropanecarboxylic acid,
1-[({3'-fluoro-4'-[(6-fluoro-1,3-benzothiazol-2-yl)amino]-3-methoxybiphenyl-4-yl}carbonyl)amino]cyclopropanecarboxylic acid,
1-[({4'-[(6-fluoro-1,3-benzothiazol-2-yl)amino]biphenyl-4-yl}carbonyl)amino]cyclopentanecarboxylic acid,
1-[({3'-fluoro-4'-[(6-fluoro-1,3-benzothiazol-2-yl)amino]biphenyl-4-yl}carbonyl)amino]cyclopentanecarboxylic acid,
1-[({4'-[(6-fluoro-1,3-benzothiazol-2-yl)amino]biphenyl-4-yl}carbonyl)amino]cyclohexanecarboxylic acid,
(2S)-2-[({4'-[(6-fluoro-1,3-benzothiazol-2-yl)amino]biphenyl-4-yl}carbonyl)amino]butanoic acid,
(2S)-2-[({3'-fluoro-4'-[(6-fluoro-1,3-benzothiazol-2-yl)amino]biphenyl-4-yl}carbonyl)amino]butanoic acid,
(2S)-2-[({3'-fluoro-4'-[(6-fluoro-1,3-benzothiazol-2-yl)amino]-3-methoxybiphenyl-4-yl}carbonyl)amino]butanoic acid,
N-({4'-[(6-fluoro-1,3-benzothiazol-2-yl)amino]biphenyl-4-yl}carbonyl)-L-norvaline,
N-({3'-fluoro-4'-[(6-fluoro-1,3-benzothiazol-2-yl)amino]biphenyl-4-yl}carbonyl)-L-norvaline,
N-({3'-fluoro-4'-[(6-fluoro-1,3-benzothiazolyl)amino]-3-methoxybiphenyl-4-yl}carbonyl)-L-norvaline,
N-({4'-[(6-fluoro-1,3-benzothiazol-2-yl)amino]biphenyl-4-yl}carbonyl)-3-methyl-L-valine,
N-({3'-fluoro-4'-[(6-fluoro-1,3-benzothiazol-2-yl)amino]biphenyl-4-yl}carbonyl)-3-methyl-L-valine, N-({3'-fluoro-4'-[(6-fluoro-1,3-benzothiazol-2-yl)amino]-3-methoxybiphenyl-4-yl}carbonyl)-3-methyl-L-valine,
4-chloro-N-({4'-[(6-fluoro-1,3-benzothiazol-2-yl)amino]biphenyl-4-yl}carbonyl)phenylalanine,
(2S)-cyclohexyl[({4'-[(6-fluoro-1,3-benzothiazol-2-yl)amino]biphenyl-4-yl}carbonyl)amino]acetic acid,
[({4'-[(6-fluoro-1,3-benzothiazol-2-yl)amino]biphenyl-4-yl}carbonyl)amino](tetrahydro-2H-pyran-4-yl)acetic acid,
[1-(tert-butoxycarbonyl)piperidin-4-yl][({4'-[(6-fluoro-1,3-benzothiazol-2-yl)amino]biphenyl-4-yl}carbonyl)amino]acetic acid,
[1-(tert-butoxycarbonyl)piperidin-3-yl][({4'-[(6-fluoro-1,3-benzothiazol-2-yl)amino]biphenyl-4-yl}carbonyl)amino]acetic acid,
[({4'-[(6-fluoro-1,3-benzothiazol-2-yl)amino] biphenyl-4-yl}carbonyl)amino](piperidin-3-yl)acetic acid,
1-({3'-fluoro-4'-[(6-fluoro-1,3-benzothiazol-2-yl)amino]biphenyl-4-yl}carbonyl)piperidine-2-carboxylic acid,
N-({4'-[(6-fluoro-1,3-benzothiazol-2-yl)amino]-3-methoxybiphenyl-4-yl}carbonyl)-L-valine,
N-({4'-[(6-fluoro-1,3-benzothiazol-2-yl)amino]-3-methylbiphenyl-4-yl}carbonyl)-L-valine,
N-({4'-[(6-methoxy-1,3-benzothiazol-2-yl)amino]-3-methylbiphenyl-4-yl}carbonyl)-L-valine,
N-({4'-(1,3-benzothiazol-2-ylamino)-3-methylbiphenyl-4-yl)carbonyl}-L-valine,
N-({4'-[(6-isopropyl-1,3-benzothiazol-2-yl)amino]-3-methylbiphenyl-4-yl}carbonyl)-L-valine,
N-({4'-[(6-chloro-1,3-benzothiazol-2-yl)amino]-3-methylbiphenyl-4-yl}carbonyl)-L-valine,
N-({4'-[(7-fluoro-1,3-benzothiazol-2-yl)amino]-3-methylbiphenyl-4-yl}carbonyl)-L-valine,
N-({4'4-[(7-chloro-1,3-benzothiazol-2-yl)amino]-3-methylbiphenyl-4-yl}carbonyl)-L-valine,
N-{[4'-(1,3-benzothiazol-2-ylamino)-3-methoxybiphenyl-4-yl}carbonyl)-L-valine,
N-{[4'-(1,3-benzothiazol-2-ylamino)biphenyl-4-yl]carbonyl}-L-valine,
N-{4'-(1,3-benzothiazol-2-ylamino)biphenyl-4-yl]carbonyl}-D-valine,
N-({4'-[(6-chloro-1,3-benzothiazol-2-yl)amino]-3-methoxybiphenyl-4-yl}carbonyl)-L-valine,
N-({4'-[(7-fluoro-1,3-benzothiazol-2-yl)amino]-3-methoxybiphenyl-4-yl}carbonyl)-L-valine,
N-({4'-[(7-chloro-1,3-benzothiazol-2-yl)amino]-3-methoxybiphenyl-4-yl}carbonyl)-L-valine,
N-({4'-[(6-isopropyl-1,3-benzothiazol-2-yl)amino]-3-methoxybiphenyl-4-yl}carbonyl)-L-valine,
N-({4'-(1,3-benzothiazol-2-ylamino)-3-chlorobiphenyl-4-yl}carbonyl)-L-valine,
N-({3-chloro-4'-[(6-isopropyl-1,3-benzothiazol-2-yl)amino]biphenyl-4-yl}carbonyl)-L-valine,
N-({3-chloro-4'-[(6-chloro-1,3-benzothiazol-2-yl)amino]biphenyl-4-yl}carbonyl)-L-valine,
N-({3-chloro-4'-[(7-fluoro-1,3-benzothiazol-2-yl)amino]biphenyl-4-yl}carbonyl)-L-valine,
N-({3-chloro-4'-[(7-chloro-1,3-benzothiazol-2-yl)amino]biphenyl-4-yl}carbonyl)-L-valine,
N-{[4'-(1,3-benzothiazol-2-ylamino)-3-methoxybiphenyl-4-yl}carbonyl)-L-leucine,
N-({3-methoxy-4'-[(6-methoxy-1,3-benzothiazol-2-yl)amino]biphenyl-4-yl}carbonyl)-L-leucine,
N-({4'-[(6-chloro-1,3-benzothiazol-2-yl)amino]-3-methoxybiphenyl-4-yl}carbonyl)-L-leucine,
N-({4'-[(4-chloro-6-fluoro-1,3-benzothiazol-2-yl)amino]-3-methoxybiphenyl-4-yl}carbonyl)-L-leucine,
N-({3-methoxy-4'-[(6-nitro-1,3-benzothiazol-2-yl)amino]biphenyl-4-yl}carbonyl)-L-leucine,
N-[(3-methoxy-4'-{[6-(methylsulfonyl)-1,3-benzothiazol-2-yl]amino}biphenyl-4-yl)carbonyl]-L-leucine,
N-({4'-[(6-isopropyl-1,3-benzothiazol-2-yl)amino]-3-methoxybiphenyl-4-yl}carbonyl)-L-leucine,
N-({4'-[(6-methoxy-1,3-benzothiazol-2-yl)amino]biphenyl-4-yl}carbonyl)-2-methylalanine,
N-({4'-(1,3-benzothiazol-2-ylamino)biphenyl-4-yl}carbonyl)-2-methylalanine,
N-{4'-[(6-chloro-1,3-benzothiazol-2-yl)amino]biphenyl-4-yl}carbonyl)-2-methylalanine,
N-{[4'-(1,3-benzothiazol-2-ylamino)biphenyl-4-yl]carbonyl}-N-methyl-L-alanine,
N-{[4'-(1,3-benzothiazol-2-ylamino)biphenyl-4-yl]carbonyl}-N-methyl-L-valine,
N-({4'-[(6-fluoro-1,3-benzothiazol-2-yl)amino]biphenyl-4-yl}carbonyl)-L-allothreonine,
N-({3'-fluoro-4'-[(6-fluoro-1,3-benzothiazol-2-yl)amino]biphenyl-4-yl}carbonyl)-L-allothreonine,
N-({3'-fluoro-4'-[(6-fluoro-1,3-benzothiazol-2-yl)amino]biphenyl-4-yl}carbonyl)-L-threonine,
N-({4'-[(6-fluoro-1,3-benzothiazol-2-yl)amino]biphenyl-4-yl}carbonyl)-L-threonine,
N-({4'-[(6-fluoro-1,3-benzothiazol-2-yl)amino]biphenyl-4-yl}carbonyl)-L-serine,
N-({3'-fluoro-4'-[(6-fluoro-1,3-benzothiazol-2-yl)amino]biphenyl-4-yl}carbonyl)-O-methyl-L-serine,
3-cyclopropyl-N-({3'-fluoro-4'-[(6-fluoro-1,3-benzothiazol-2-yl)amino]biphenyl-4-yl}carbonyl)-L-alanine,
N-({4'-[(6-fluoro-1,3-benzothiazol-2-yl)amino]biphenyl-4-yl}carbonyl)-O-methyl-L-serine,
3-cyclopropyl-N-({4'-[(6-fluoro-1,3-benzothiazol-2-yl)amino]biphenyl-4-yl}carbonyl)-L-alanine,
N-({3'-fluoro-4'-[(6-fluoro-1,3-benzothiazol-2-yl)amino]biphenyl-4-yl}carbonyl)—N-methyl-L-valine,
N-({4'-[(6-fluoro-1,3-benzothiazol-2-yl)amino]biphenyl-4-yl}carbonyl)-N-methyl-L-valine,
N-({3-fluoro-4'-[(6-fluoro-1,3-benzothiazol-2-yl)amino]biphenyl-4-yl}carbonyl)-L-valine,
N-({3-fluoro-4'-[(6-fluoro-1,3-benzothiazol-2-yl)amino]biphenyl-4-yl}carbonyl)-L-leucine,
N-({3-fluoro-4'-[(6-fluoro-1,3-benzothiazol-2-yl)amino]biphenyl-4-yl}carbonyl)-3-methyl-L-valine,
N-({3-fluoro-4'-[(6-fluoro-1,3-benzothiazol-2-yl)amino]biphenyl-4-yl}carbonyl)-L-isoleucine,
N-({3-fluoro-4'-[(6-fluoro-1,3-benzothiazol-2-yl)amino]biphenyl-4-yl}carbonyl)-L-norvaline,
(2S)-2-[({3-fluoro-4'-[(6-fluoro-1,3-benzothiazol-2-yl)amino]biphenyl-4-yl}carbonyl)amino]butanoic acid,
3-cyclopropyl-N-({3-fluoro-4'-[(6-fluoro-1,3-benzothiazol-2-yl)amino]biphenyl-4-yl}carbonyl)-L-alanine,
N-({3,3'-difluoro-4'-[(6-fluoro-1,3-benzothiazol-2-yl)amino]biphenyl-4-yl}carbonyl)-L-valine,
N-({3,3'-difluoro-4'-[(6-fluoro-1,3-benzothiazol-2-yl)amino]biphenyl-4-yl}carbonyl)-L-leucine,
N-({3,3'-difluoro-4'-[(6-fluoro-1,3-benzothiazol-2-yl)amino]biphenyl-4-yl}carbonyl)-3-methyl-L-valine,
N-({3,3'-difluoro-4'-[(6-fluoro-1,3-benzothiazol-2-yl)amino]biphenyl-4-yl}carbonyl)-L-norvaline,
(2S)-2-[({3,3'-difluoro-4'-[(6-fluoro-1,3-benzothiazol-2-yl)amino]biphenyl-4-yl}carbonyl)amino]butanoic acid,
3-cyclopropyl-N-({3,3'-difluoro-4'-[(6-fluoro-1,3-benzothiazol-2-yl)amino]biphenyl-4-yl}carbonyl)-L-alanine, N-[(3'-fluoro-4'-{[6-(trifluoromethoxy)-1,3-benzothiazol-2-yl]amino}biphenyl-4-yl)carbonyl]-L-valine,
N-[(3'-fluoro-4'-{[6-(trifluoromethoxy)-1,3-benzothiazol-2-yl]amino}biphenyl-4-yl)carbonyl]-L-leucine,
N-[(3'-fluoro-4'-{[6-(trifluoromethoxy)-1,3-benzothiazol-2-yl]amino}biphenyl-4-yl)carbonyl]-L-norvaline,
N-[(3'-fluoro-4'-{[6-(trifluoromethoxy)-1,3-benzothiazol-2-yl]amino}biphenyl-4-yl)carbonyl]-L-isoleucine,
N-[(3'-fluoro-4'-{[6-(trifluoromethoxy)-1,3-benzothiazol-2-yl]amino}biphenyl-4-yl)carbonyl]-3-methyl-L-valine,
3-cyclopropyl-N-[(3'-fluoro-4'-{[6-(trifluoromethoxy)-1,3-benzothiazol-2-yl]amino}biphenyl-4-yl)carbonyl]-L-alanine,
(2S)-2-{[(3'-fluoro-4'-{[6-(trifluoromethoxy)-1,3-benzothiazol-2-yl]amino}biphenyl-4-yl)carbonyl]amino}butanoic acid,
N-({4'-[(6-chloro-1,3-benzothiazol-2-yl)amino]-3'-fluorobiphenyl-4-yl}carbonyl)-L-leucine,
N-({4'-[(6-chloro-1,3-benzothiazol-2-yl)amino]biphenyl-4-yl}carbonyl)-L-valine,
N-({4'-[(6-chloro-1,3-benzothiazol-2-yl)amino]biphenyl-4-yl}carbonyl)-L-leucine,
N-({4'-[(6-chloro-1,3-benzothiazol-2-yl)amino]biphenyl-4-yl}carbonyl)-L-norvaline,
N-({4'-[(6-chloro-1,3-benzothiazol-2-yl)amino]biphenyl-4-yl}carbonyl)-L-isoleucine,
N-({4'-[(6-chloro-1,3-benzothiazol-2-yl)amino]biphenyl-4-yl}carbonyl)-3-methyl-L-valine,
N-({4'-[(6-chloro-1,3-benzothiazol-2-yl)amino]-3'-fluorobiphenyl-4-yl}carbonyl)-L-valine,
N-({4'-[(6-chloro-1,3-benzothiazol-2-yl)amino]-3'-fluorobiphenyl-4-yl}carbonyl)-L-norvaline,
(2S)-2-[({4'-[(6-chloro-1,3-benzothiazol-2-yl)amino]-3'-fluorobiphenyl-4-yl}carbonyl)amino]butanoic acid,
N-({4'-[(6-chloro-1,3-benzothiazol-2-yl)amino]biphenyl-4-yl}carbonyl)-3-cyclopropyl-L-alanine,
N-({4'-[(6-chloro-1,3-benzothiazol-2-yl)amino]-3'-fluorobiphenyl-4-yl}carbonyl)-3-methyl-L-valine,
(2S)-2-[({4'-[(6-chloro-1,3-benzothiazol-2-yl)amino]biphenyl-4-yl}carbonyl)amino]butanoic acid,
N-{[4'-([1,3]thiazolo[5,4-b]pyridin-2-ylamino)biphenyl-4-yl]carbonyl}-L-valine,
N-{[4'-([1,3]thiazolo[4,5-c]pyridin-2-ylamino)biphenyl-4-yl]carbonyl}-L-valine,
N-{[4'-([1,3]thiazolo[4,5-b]pyridin-2-ylamino)biphenyl-4-yl]carbonyl}-L-valine,
N-[3'-fluoro-4'-{[6-(trifluoromethyl)[1,3]thiazolo[4,5-b]pyridin-2-yl]amino}biphenyl-4-yl)carbonyl]-L-valine,
N-{[3'-fluoro-4'-([1,3]thiazolo[4,5-c]pyridin-2-ylamino)biphenyl-4-yl]carbonyl}-L-valine,
N-({[3'-fluoro-4'-([1,3]thiazolo[4,5-b]pyridin-2-ylamino)biphenyl-4-yl]carbonyl}-L-valine,
N-({3'-fluoro-4'-[(6-fluoro-1,3-benzothiazol-2-yl)amino]biphenyl-4-yl}carbonyl)-O-methyl-L-allothreonine,
N-({3'-fluoro-4'-[(6-fluoro-1,3-benzothiazol-2-yl)amino]biphenyl-4-yl}carbonyl)—N-methyl-L-norvaline,
4,4,4-trifluoro-2-[({3'-fluoro-4'-[(6-fluoro-1,3-benzothiazol-2-yl)amino]biphenyl-4-yl}carbonyl)amino]butanoic acid,
N-({3'-fluoro-4'-[(6-fluoro-1,3-benzothiazol-2-yl)amino]biphenyl-4-yl}carbonyl)-4-methylene-L-norvaline,
3-cyclobutyl-N-({3'-fluoro-4'-[(6-fluoro-1,3-benzothiazol-2-yl)amino]biphenyl-4-yl}carbonyl)-L-alanine,
(2S)-[({3'-fluoro-4'-[(6-fluoro-1,3-benzothiazol-2-yl)amino]biphenyl-4-yl}carbonyl)amino](phenyl)acetic acid,
N-({4'-[(6-fluoro-1,3-benzothiazol-2-yl)amino]biphenyl-4-yl}carbonyl)-O-methyl-L-allothreonine,
N-({4'-[(6-fluoro-1,3-benzothiazol-2-yl)amino]biphenyl-4-yl}carbonyl)-N-methyl-L-norvaline,
1-[({4'-[(6-fluoro-1,3-benzothiazol-2-yl)amino]biphenyl-4-yl}carbonyl)(methyl)amino]cyclopropanecarboxylic acid,
(4R)-3-({4'-[(6-fluoro-1,3-benzothiazol-2-yl)amino]biphenyl-4-yl}carbonyl)-5,5-dimethyl-1,3-thiazolidine-4-carboxylic acid,
4,4,4-trifluoro-2-[({4'-[(6-fluoro-1,3-benzothiazol-2-yl)amino]biphenyl-4-yl}carbonyl)amino]butanoic acid,
N-({4'-[(6-fluoro-1,3-benzothiazol-2-yl)amino]biphenyl-4-yl}carbonyl)-4-methylene-L-norvaline,
3-cyclobutyl-N-({4'-[(6-fluoro-1,3-benzothiazol-2-yl)amino]biphenyl-4-yl}carbonyl)-L-alanine,
(2S)-[({4'-[(6-fluoro-1,3-benzothiazol-2-yl)amino]biphenyl-4-yl}carbonyl)amino](phenyl)acetic acid,
N-[(3'-fluoro-4'-{[6-(trifluoromethyl)-1,3-benzothiazol-2-yl]amino}biphenyl-4-yl)carbonyl]-L-valine,
N-[(3'-fluoro-4'-{[6-(trifluoromethyl)-1,3-benzothiazol-2-yl]amino}biphenyl-4-yl)carbonyl]-L-leucine,
N-[(3'-fluoro-4'-{[6-(trifluoromethyl)-1,3-benzothiazol-2-yl]amino}biphenyl-4-yl)carbonyl]-L-norvaline,
N-[(3'-fluoro-4'-{[6-(trifluoromethyl)-1,3-benzothiazol-2-yl]amino}biphenyl-4-yl)carbonyl]-3-methyl-L-valine,
(2S)-2-{[(3'-fluoro-4'-{[6-(trifluoromethyl)-1,3-benzothiazol-2-yl]amino} biphenyl-4-yl)carbonyl] amino}butanoic acid,
N-[(3'-fluoro-4'-{[6-(trifluoromethyl)-1,3-benzothiazol-2-yl]amino} biphenyl-4-yl)carbonyl]-L-isoleucine,
3-cyclopropyl-N-[(3'-fluoro-4'-{[6-(trifluoromethyl)-1,3-benzothiazol-2-yl]amino}biphenyl-4-yl)carbonyl]-L-alanine,
N-[(4'-{[6-(trifluoromethyl)-1,3-benzothiazol-2-yl]amino} biphenyl-4-yl)carbonyl]-L-valine,
N-[(4'-{[6-(trifluoromethyl)-1,3-benzothiazol-2-yl]amino} biphenyl-4-yl)carbonyl]-L-leucine,
N-[(4'-{[6-(trifluoromethyl)-1,3-benzothiazol-2-yl]amino}biphenyl-4-yl)carbonyl]-L-norvaline,
3-methyl-N-[(4'-{[6-(trifluoromethyl)-1,3-benzothiazol-2-yl]amino} biphenyl-4-yl)carbonyl]-L-valine,
(2S)-2-{[(4'-{[6-(trifluoromethyl)-1,3-benzothiazol-2-yl]amino}biphenyl-4-yl)carbonyl]amino}butanoic acid,
N-[(4'-{[6-(trifluoromethyl)-1,3-benzothiazol-2-yl]amino}biphenyl-4-yl)carbonyl]-L-isoleucine,
3-cyclopropyl-N-[(4'-{[6-(trifluoromethyl)-1,3-benzothiazol-2-yl]amino}biphenyl-4-yl)carbonyl]-L-alanine,
N-({3'-fluoro-4'-[(6-isopropyl-1,3-benzothiazol-2-yl)amino]biphenyl-4-yl}carbonyl)-L-valine,
N-({3'-fluoro-4'-[(6-isopropyl-1,3-benzothiazol-2-yl)amino]biphenyl-4-yl}carbonyl)-L-leucine,
N-({3'-fluoro-4'-[(6-isopropyl-1,3-benzothiazol-2-yl)amino]biphenyl-4-yl}carbonyl)-L-norvaline,
(2S)-2-[({3'-fluoro-4'-[(6-isopropyl-1,3-benzothiazol-2-yl)amino]biphenyl-4-yl}carbonyl)amino]butanoic acid,
N-({3'-fluoro-4'-[(6-isopropyl-1,3-benzothiazol-2-yl)amino]biphenyl-4-yl}carbonyl)-3-methyl-L-valine,
N-({3'-fluoro-4'-[(6-isopropyl-1,3-benzothiazol-2-yl)amino]biphenyl-4-yl}carbonyl)-L-isoleucine,
3-cyclopropyl-N-({3'-fluoro-4'-[(6-isopropyl-1,3-benzothiazol-2-yl)amino]biphenyl-4-yl}carbonyl)-L-alanine,
N-[(4'-{[6-(trifluoromethyl)[1,3]thiazolo[4,5-b]pyridin-2-yl]amino}biphenyl-4-yl)carbonyl]-L-leucine, N-{(4'-{[6-(trifluoromethyl)[1,3]thiazolo[4,5-b]pyridin-2-yl]amino}biphenyl-4-yl}carbonyl]-L-norvaline, 3-methyl-N-[(4'-{[6-(trifluoromethyl)[1,3]thiazolo[4,5-b]pyridin-2-yl]amino}biphenyl-4-yl)carbonyl]-L-valine, (2S)-2-{[(4'-{[6-(trifluoromethyl)[1,3]thiazolo[4,5-b]pyridin-2-yl]amino}biphenyl-4-yl)carbonyl]amino}butanoic acid, N-[(4'-{[6-(trifluoromethyl)[1,3]thiazolo[4,5-b]pyridin-2-yl]amino}biphenyl-4-yl)carbonyl]-L-isoleucine, 3-cyclopropyl-N-[(4'-{[6-(trifluoromethyl)[1,3]thiazolo[4,5-b]pyridin-2-yl]amino}biphenyl-4-yl)carbonyl]-L-alanine, N-[(3'-fluoro-4'-{[6-(trifluoromethyl)[1,3]thiazolo[4,5-b]pyridin-2-yl]amino}biphenyl-4-yl)carbonyl]-L-leucine, N-[(3'-fluoro-4'-{[6-(trifluoromethyl)[1,3]thiazolo[4,5-b]pyridin-2-yl]amino} biphenyl-4-yl)carbonyl]-L-norvaline, N-[(3'-fluoro-4'-{[6-(trifluoromethyl)[1,3]thiazolo[4,5-b]pyridin-2-yl]amino}biphenyl-4-yl)carbonyl]-3-methyl-L-valine, (2S)-2-{[(3'-fluoro-4'-{[6-(trifluoromethyl)[1,3]thiazolo[4,5-b]pyridin-2-yl]amino} biphenyl-4-yl)carbonyl]amino}butanoic acid, N-[(3'-fluoro-4'-{[6-(trifluoromethyl)[1,3]thiazolo[4,5-b]pyridin-2-yl]amino}biphenyl-4-yl)carbonyl]-L-isoleucine, and N-({4'-[(7-chloro[1,3]thiazolo[5,4-c]pyridin-2-yl)amino]-3'-fluorobiphenyl-4-yl}carbonyl)-L-valine.

6. A pharmaceutical composition comprising an effective amount of a compound of claim 1, or a pharmaceutically acceptable salt thereof, in combination with a pharmaceutically acceptable carrier.

7. A pharmaceutical composition comprising a therapeutically effective amount of a compound of claim 1, or a pharmaceutically acceptable salt thereof, in combination with a pharmaceutically acceptable carrier and one or more pharmaceutical agents.

8. The pharmaceutical composition of claim 7 wherein said pharmaceutical agent is selected from the group consisting of PPAR ligands, insulin secretagogues, sulfonylurea drugs, α-glucosidase inhibitors, insulin sensitizers, hepatic glucose output lowering compounds, insulin and insulin derivatives, biguanides, protein tyrosine phosphatase-1B, dipeptidyl peptidase IV, 11beta-HSD inhibitors, anti-obesity drugs, HMG-CoA reductase inhibitors, nicotinic acid, lipid lowering drugs, ACAT inhibitors, bile acid sequestrants, bile acid reuptake inhibitors, microsomal triglyceride transport inhibitors, fabric acid derivatives, β-blockers, ACE inhibitors, calcium channel blockers, diuretics, renin inhibitors, AT-1 receptor antagonists, ET receptor antagonists, neutral endopeptidase inhibitors, vasopeptidase inhibitors, and nitrates.

9. The pharmaceutical composition of claim 7 wherein said pharmaceutical agent is selected from β-3 adrenergic receptor agonists, cannabinoid antagonists, neuropeptide-Y receptor antagonists, neuropeptide Y5 inhibitors, apo-B/MTP inhibitors, 11β-hydroxy steroid dehydrogenase-1 inhibitors, peptide $YY_{3-36}$ or analogs thereof, MCR4 agonists, CCK-A agonists, monoamine reuptake inhibitors, sympathomimetic agents, dopamine agonists, melanocyte-stimulating hormone receptor analogs, melanin concentrating hormone antagonists, leptin, leptin analogs, leptin receptor agonists, galanin antagonists, lipase inhibitors, bombesin agonists, thyromimetic agents, dehydroepiandrosterone or analogs thereof, glucocorticoid receptor antagonists, orexin receptor antagonists, ciliary neurotrophic factor, ghrelin receptor antagonists, histamine-3 receptor antagonists, neuromedin U receptor agonists, appetite suppressants, and compound that modulates digestion and/or metabolism.

* * * * *